US012668817B1

(12) United States Patent
Plasschaert et al.

(10) Patent No.: US 12,668,817 B1
(45) Date of Patent: Jun. 30, 2026

(54) RECOMBINANT ADENO-ASSOCIATED VIRAL VECTORS FOR DELIVERING A THERAPEUTIC GENE TO LUNGS

(71) Applicant: Telomere Therapeutics S.L., Barcelona (ES)

(72) Inventors: Lindsey Plasschaert, Barcelona (ES); Marta Gabasa-Ferrandez, Barcelona (ES)

(73) Assignee: Telomere Therapeutics S.L., Barcelona (ES)

( * ) Notice: Subject to any disclaimer, the term of this patent is extended or adjusted under 35 U.S.C. 154(b) by 0 days.

(21) Appl. No.: 19/265,031

(22) Filed: Jul. 10, 2025

(51) Int. Cl.
*C12N 15/86* (2006.01)
*C12N 9/12* (2006.01)
*A61K 48/00* (2006.01)

(52) U.S. Cl.
CPC ........... *C12N 15/86* (2013.01); *C12N 9/1276* (2013.01); *C12Y 207/07049* (2013.01); *A61K 48/00* (2013.01); *C12N 2750/14143* (2013.01); *C12N 2830/007* (2013.01); *C12N 2830/50* (2013.01)

(58) Field of Classification Search
None
See application file for complete search history.

(56) References Cited

U.S. PATENT DOCUMENTS 11,878,060 B2 * 1/2024 Dominy ............. C07K 16/2851
2025/0099618 A1 * 3/2025 Blasco ................... C12N 15/86

OTHER PUBLICATIONS

Kang, M.H., van Lieshout, L.P., Xu, L. et al. A lung tropic AAV vector improves survival in a mouse model of surfactant B deficiency. Nat Commun 11, 3929 (2020). https://doi.org/10.1038/s41467-020-17577-8 (Year: 2020).*
Vandenberghe et al. "UniProt." UniProt, 2025, www.uniprot.org/uniprotkb/B4Y875/entry. 2007. (Year: 2007).*

* cited by examiner

*Primary Examiner* — Anna Skibinsky
*Assistant Examiner* — Catherine L McCormick
(74) *Attorney, Agent, or Firm* — Wolf, Greenfield & Sacks, P.C.

(57) ABSTRACT

The present invention provides a recombinant adeno-associated virus (rAAV) particle of 6.2 serotype comprising a recombinant nucleic acid comprising a lung-specific SpB promoter and a therapeutic gene, wherein the lung-specific promoter comprises SEQ ID NO: 1, and wherein said promoter is operably linked to and regulates the expression of the therapeutic gene.

17 Claims, 13 Drawing Sheets

Specification includes a Sequence Listing.

Fig. 7
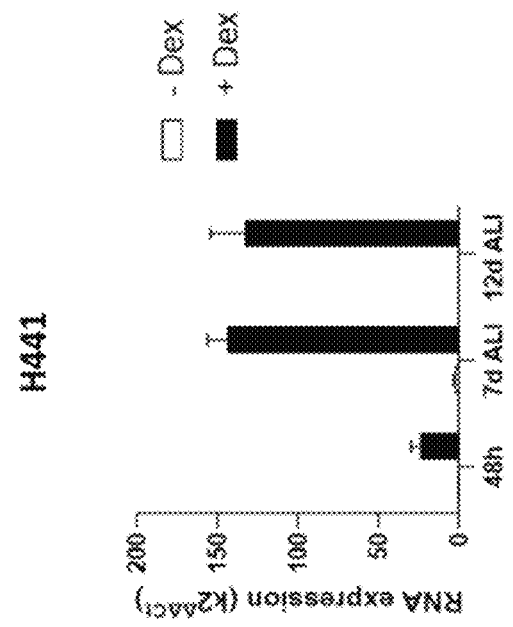
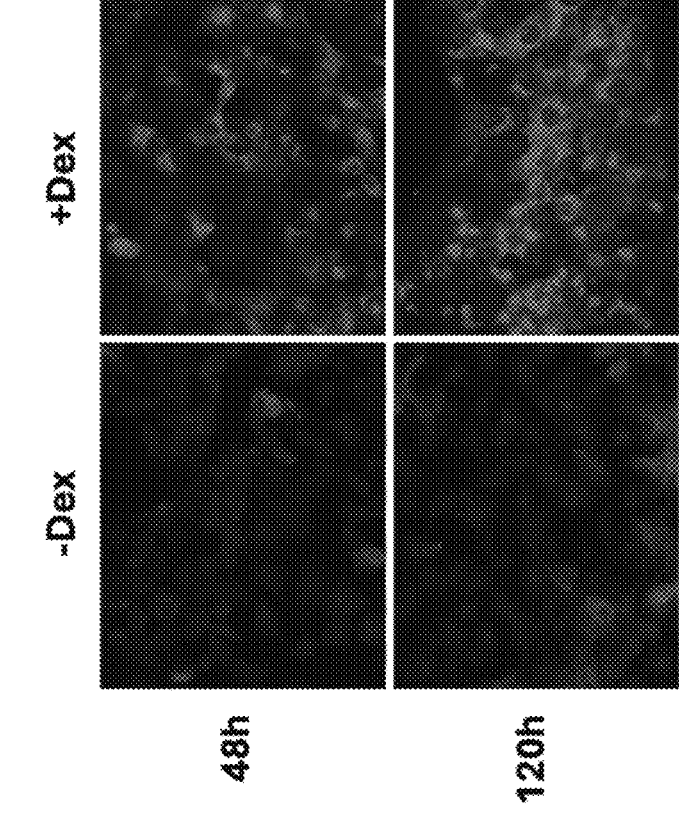

A

B

A

B

C

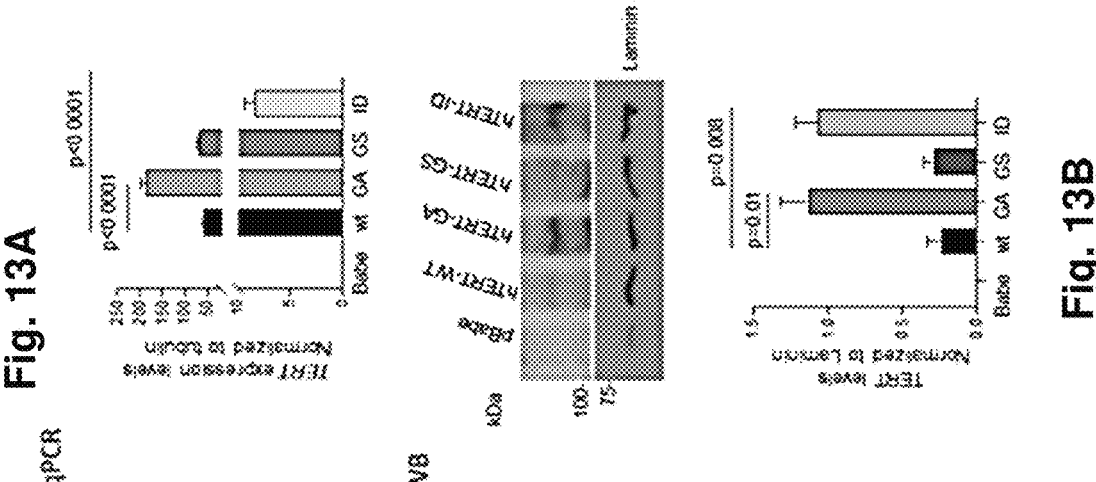

RECOMBINANT ADENO-ASSOCIATED VIRAL VECTORS FOR DELIVERING A THERAPEUTIC GENE TO LUNGS

REFERENCE TO AN ELECTRONIC SEQUENCE LISTING

The contents of the electronic sequence listing (T097670000US00-SEQ-JRV.xml; Size: 41,523 bytes; and Date of Creation: Jul. 9, 2025) is herein incorporated by reference in its entirety.

TECHNICAL FIELD

The present disclosure relates to the field of medicine, particularly gene therapy.

BACKGROUND ART

Gene therapy is a rapidly advancing field that involves the delivery of therapeutic genetic material into a patient's cells to treat or prevent disease. It holds particular promise for monogenic disorders, cancers, and certain acquired conditions by enabling the correction, replacement, or regulation of defective or absent genes. Delivery of therapeutic genes to specific tissues remains a central challenge in gene therapy, necessitating the development of effective and targeted delivery vehicles.

Adeno-associated virus (AAV) vectors have emerged as one of the most promising tools for in vivo gene delivery due to their ability to infect dividing and non-dividing cells, relatively low immunogenicity, and stable expression in host cells. Recombinant AAVs (rAAVs), which are engineered to carry therapeutic transgenes in place of viral genes, are widely used in both preclinical and clinical gene therapy applications.

One of the critical advantages of AAV vectors is the existence of multiple natural and engineered serotypes, each with distinct tissue tropisms. These serotypes determine the efficiency and specificity with which the vector can transduce cells in target organs. Despite these advantages, several limitations remain in the field. Existing AAV vectors are associated with drawbacks which affect their effectiveness in gene therapy, such as low gene expression in target tissues, off-target gene expression in tissues other than the ones being treated and the occurrence of intermediate vector species containing truncated viral genomes.

Efforts are ongoing to improve vector design through capsid engineering, the use of synthetic or chimeric serotypes, directed evolution, and rational mutagenesis. Additionally, targeted gene expression is being improved through cell-specific promoters. Parallel advancements are being made in vector production, purification, and delivery strategies to enhance targeting efficiency, tissue specificity, and immune evasion. The field continues to seek improved AAV-based systems that are capable of achieving high-efficiency, tissue-specific, and durable gene expression with minimal immunogenicity and off-target effects. In view of the above, there is a need for the provision of improved recombinant viral genomes and vectors for gene therapy.

SUMMARY

The present disclosure provides a viral vector and promoter that efficiently targets and expresses a therapeutic gene in lung cells, while minimizing or eliminating expression in the liver.

According to one aspect, recombinant adeno-associated virus (rAAV) particles are provided. The rAAV particles include (a) a recombinant nucleic acid comprising a lung-specific SpB promoter and a therapeutic gene, wherein the lung-specific SpB promoter comprises SEQ ID NO: 1, and wherein the lung-specific SpB promoter is operably linked to the therapeutic gene, and (b) an AAV capsid of 6.2 serotype.

In some embodiments, the therapeutic gene encodes for human telomerase reverse transcriptase (TERT). In some embodiments, the therapeutic gene encodes a protein comprising SEQ ID NO: 2 or 3.

In some embodiments, the AAV capsid of 6.2 serotype comprises a VP1 protein comprising SEQ ID NO: 15.

In some embodiments, the therapeutic gene comprises SEQ ID NO: 8, 9, 11, 12, or 13. In some embodiments, the therapeutic gene comprises SEQ ID NO: 11.

In some embodiments, the recombinant nucleic acid of (a) further comprises a Kozak sequence upstream of the therapeutic gene. In some embodiments, the Kozak sequence comprises SEQ ID NO: 4.

In some embodiments, the recombinant nucleic acid of (a) further comprises a polyadenylation (Poly-A) signal, preferably the bovine growth hormone polyadenylation signal, placed downstream the therapeutic gene. In some embodiments, the Poly-A signal is a bovine growth hormone polyadenylation signal.

In some embodiments, the recombinant nucleic acid of (a) further comprises a 5'-end and 3'-end inverted terminal repeat (ITR) sequences from AAV serotype 2 (AAV2). In some embodiments, the 5'-end and 3'-end AAV2 ITR sequences comprise SEQ ID NO: 6 and 7, respectively.

In some embodiments, the recombinant nucleic acid of (a) comprises SEQ ID NO: 10.

According to another aspect, methods of treating or preventing a lung disease are provided. The methods include administering the rAAV particle described herein to a subject in need thereof. In some embodiments, the recombinant nucleic acid of (a) comprises SEQ ID NO: 10. In some embodiments, the lung disease is pulmonary fibrosis. In some embodiments, the pulmonary fibrosis is idiopathic pulmonary fibrosis.

BRIEF DESCRIPTION OF DRAWINGS

FIGS. 5A-5B. Purity check: FIG. 5A. Lane 1: Prestained Protein Marker, Lane 2: AAV6.2-SpB-hTERT, FIG. 5B.

Lane 1: Prestained Protein Marker, Lane 2: AAV6.2-SpB-GFP. Load: $5.0\times10^{10}$ vg/Lane.

Figures 6A, 6B:
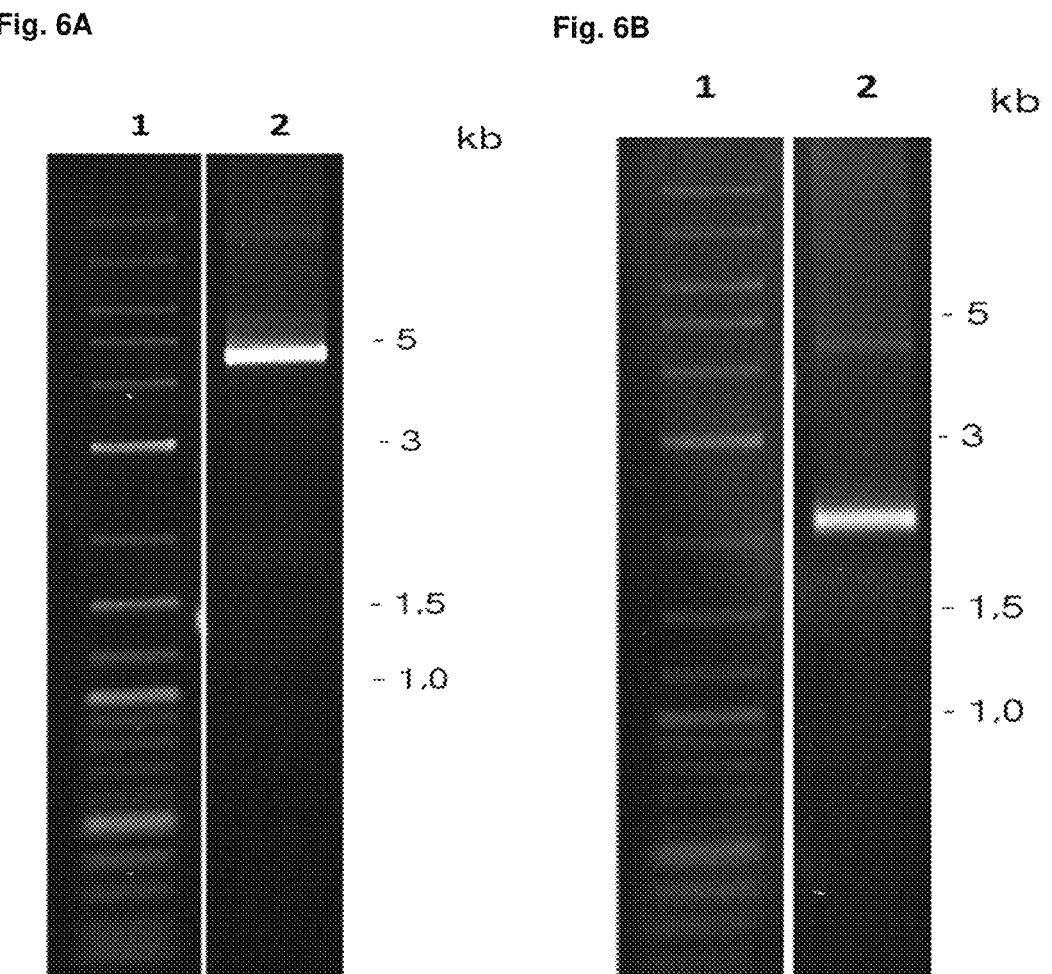

FIGS. 6A-6B. Integrity check of packaged vector genomes: FIG. 6A. Lane 1: DNA Ladder, Lane 2: AAV6.2-SpB-hTERT, FIG. 6B. Lane 1: DNA Ladder, Lane 2: AAV6.2-SpB-GFP. Load: $4.0\times10^{10}$ vg/Lane.

FIG. 7. H441 cells treated with Dexamethasone (Dex) turn on SpB expression as shown by immunostaining for SpB protein (red) or measuring SpB RNA by RT-qPCR.

Figure 8:
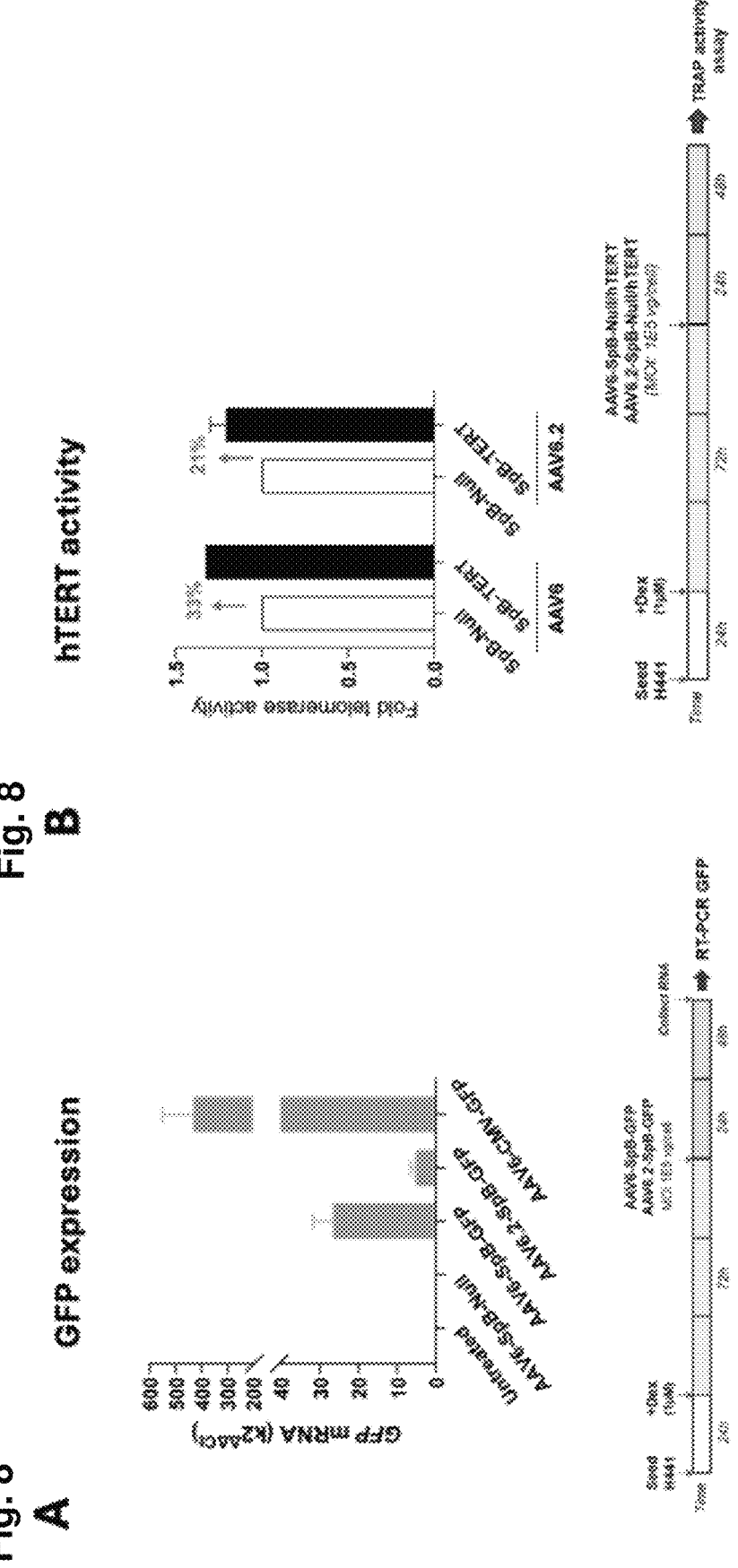

FIGS. 8A-8B. AAV vectors transduce H441 cells and drive expression with SpB and CMV promoters.

FIGS. 9A-9B. AAV6.2-SpB combination restricts trans-gene expression in liver cell lines. Liver epithelial cells (HepG2; hepatocytes), liver endothelial cells (SK-HEP-1), and lung epithelial cells (H441) were transduced with AAV6 or 6.2 expressing GFP transgene driven by the SpB or CMV promoter at a dose of $7.5\times10^4$. 72 hours after transduction, flow cytometry was performed for GFP. Quantification of GFP+ cells (FIG. 9A) and representative gating of GFP for several conditions (FIG. 9B) is shown. N=3 independent experiments. p-values determined by student's t-test.

FIGS. 10A-10C. Lung fibroblasts transduced with AAVs demonstrate specificity of SpB promoter. Human lung fibroblasts were transduced with ascending doses of AAV6 expressing a GFP transgene driven by SpB or CMV or a null cargo. 72 hours after transduction, cells were harvested for RT-qPCR for GFP expression (FIG. 10A) or flow cytometry for GFP protein (FIG. 10B). Representative gating for GFP is shown for each condition (FIG. 10C). N=1 experiment for each dose/condition.

Figure 11:
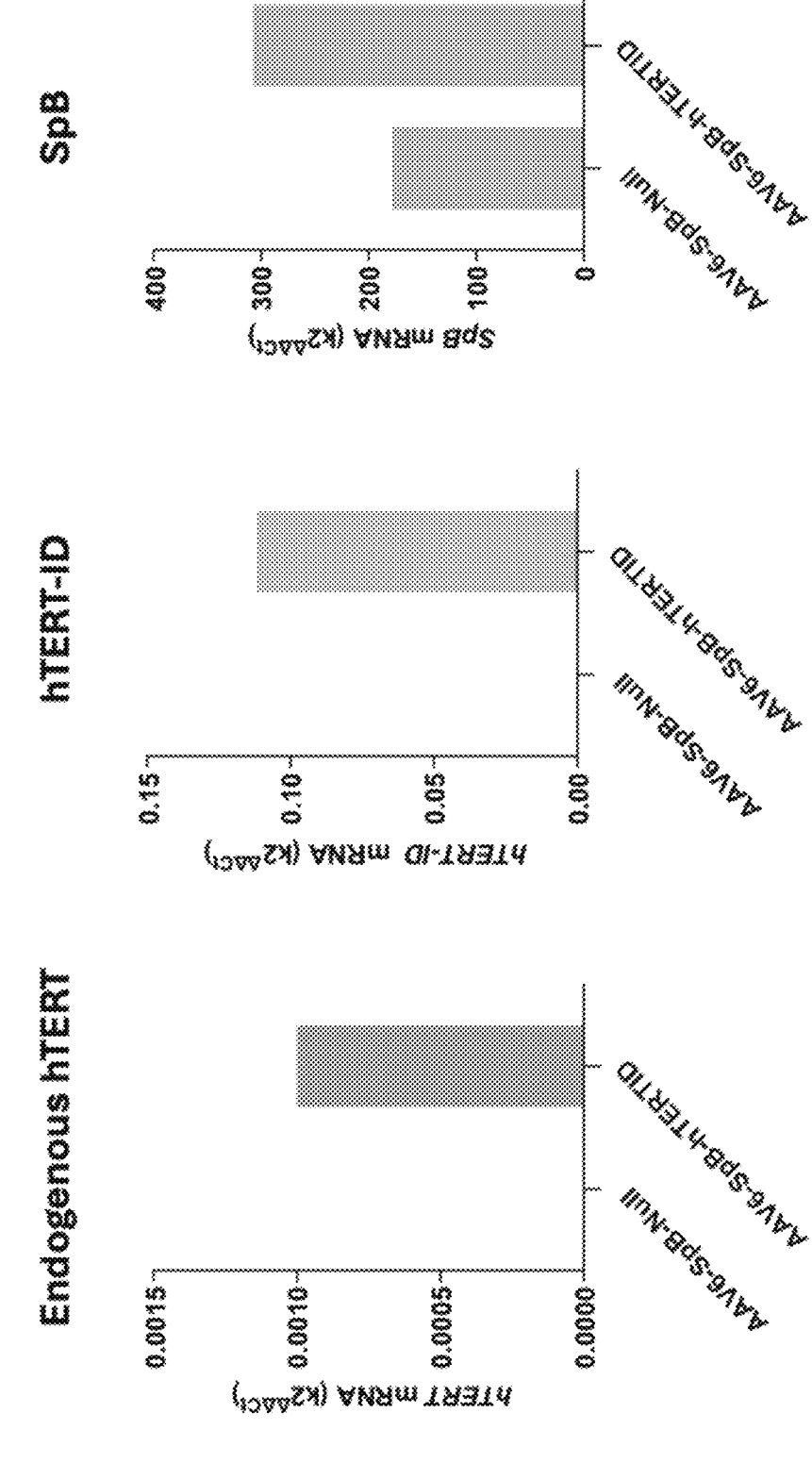

FIG. 11. Human lung-derived AT2 cell organoids were passaged and transduced with AAVs at passage 3. Five days following AAV treatment, RNA was isolated and endogenous SpB and hTERT as well as exogenous hTERTID were measured by RT-qPCR.

Figures 12A, 12B, 12C:
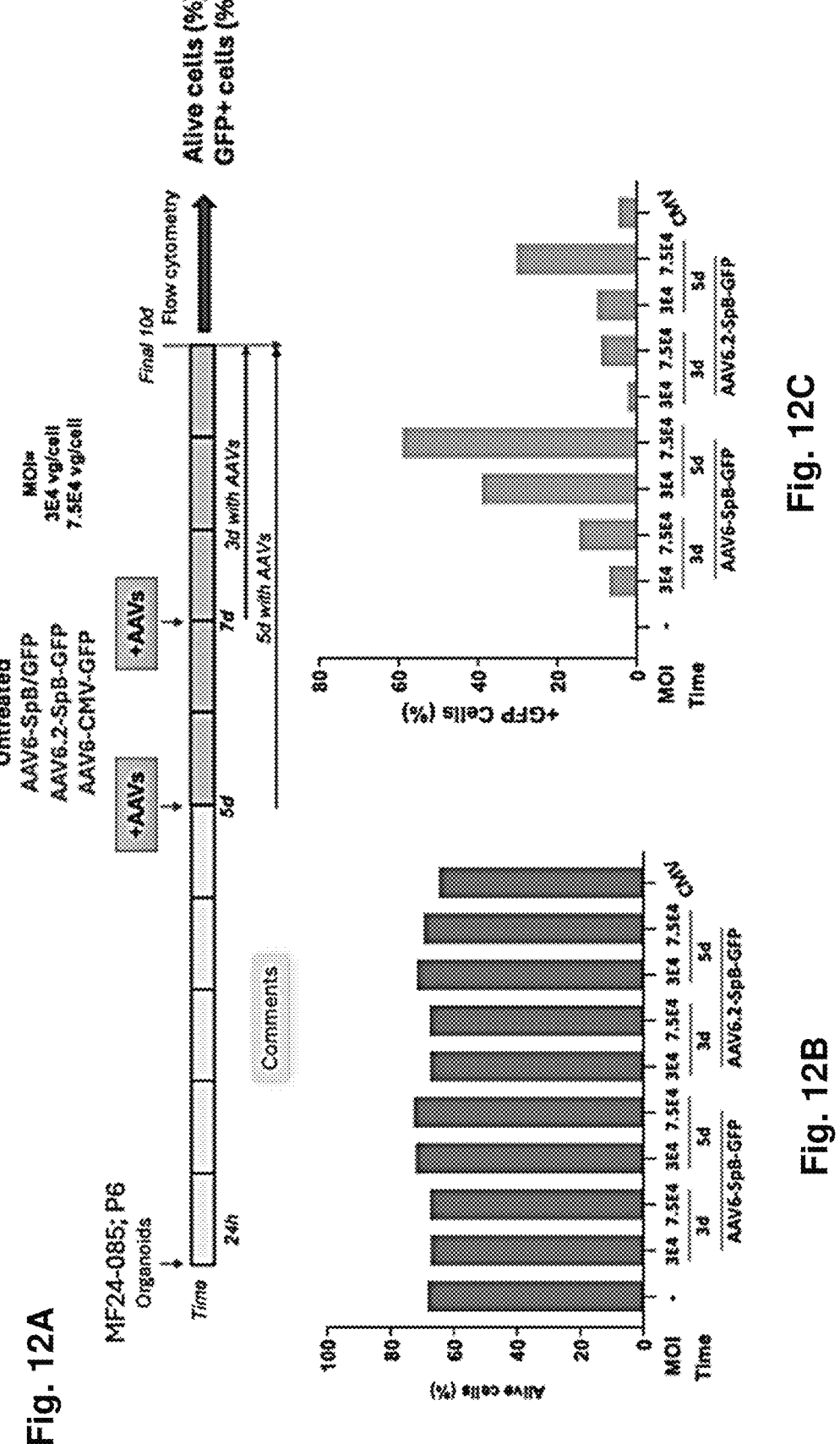

FIGS. 12A-12C. Primary human lung AT2 cells isolate and passaged in 3D organoids were transduced with AAVs and harvested for flow cytometry 3 days or 5 days later (FIG. 12A). Culture conditions and AAV transduction did not affect cell viability (FIG. 12B). Dose dependent response of SpB-driven GFP protein can be seen with transduction after 3 and 5 days (FIG. 12C).

FIGS. 13A-13C. Three different codon optimizations of hTERT were generated (hTERT-GA, hTERT-GS, and hTERT-ID) and cloned into pBabe retroviral vector. BJ human fibroblasts were transduced with pBabe-hTERT-WT, pBabe-hTERT-GA, pBabe-hTERT-GS, and pBabe-hTERT-ID. Telomerase transcription level was analyzed by qPCR using specific primers for each allele (FIG. 13A). Telomerase protein levels were analyzed by Western blot (WB; FIG. 13B) and telomerase activity was analyzed by TRAP (FIG. 13C).

GENERAL DEFINITIONS

It must be noted that, as used herein, the singular forms "a", "an", and "the", include plural references unless the context clearly indicates otherwise. Further, unless otherwise indicated, the term "at least" preceding a series of elements is to be understood to refer to every element in the series. Those skilled in the art will recognize or be able to ascertain using no more than routine experimentation, many equivalents to the specific embodiments described herein. Such equivalents are intended to be encompassed by the present disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, words of approximation such as, without limitation, "about", "around", "approximately" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by +1, 2, 3, 4, 5, 6, 7, 8, 9, 10, 11, 12, 13, 14 or 15%. Preferably the term "about" means exactly the indicated value (+0%).

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having". Any of the aforementioned terms (comprising, containing, including, having), whenever used herein in the context of an aspect or embodiment of the present disclosure may be substituted with the term "consisting of", though less preferred.

When used herein "consisting of" excludes any element, step, or ingredient not specified in the claim element. When used herein, "consisting essentially of does not exclude materials or steps that do not materially affect the basic and novel characteristics of the claim.

"Genome" as used herein encompasses not only chromosomal DNA present in the nucleus, but also organelle DNA present in the subcellular components (e.g., mitochondria, plastids) of the cell.

"Polynucleotide", "nucleic acid sequence", "nucleotide sequence", or "nucleic acid fragment" are used interchangeably to refer to a polymer of RNA or DNA or both that is single- or double-stranded.

"Polypeptide", "peptide", and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, sulfation, gamma-carboxylation of glutamic acid residues, hydroxylation and ADP-ribosylation.

The terms "sequence identity" or "percent identity" in the context of two or more nucleotide sequences, polypeptide sequences or proteins sequences refers to two or more sequences or subsequences that are the same ("identical") or have a specified percentage of nucleotide or amino acid residues that are identical ("percent identity") when compared and aligned for maximum correspondence with a second molecule, as measured using a sequence comparison algorithm, preferably BLAST alignment tool, or alternatively, by visual inspection. The "sequence identity" or "percent identity" can be determined by calculating the number of identical nucleotides or amino acids at the same positions in a nucleic acid, polypeptide or protein. Calculation of percent identity includes determination of the optimal alignment between two or more sequences. Alignment can take into account insertions and deletions (i.e. "gaps") in each of the sequences to be tested, such as, without limitation, in the non-coding regions of nucleic acids and truncations or extensions of polypeptide sequences. Computer programs and algorithms such as the Basic Local Alignment Search Tool (BLAST) may be used to determine the percent identity. BLAST is one of the many resources provided by the U.S. National Center for Biotechnology Information. Because the genetic code is degenerate, and more than one codon can encode a given amino acid, coding regions of nucleic acids are considered identical if the nucleic acids encode identical polypeptides. Thus, percent identity could also be calculated based on the polypeptide encoded by the nucleic acid.

The term "encoding" refers to the inherent property of specific sequences of polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system.

DESCRIPTION

AAV vectors with optimized tropism for specific tissues are highly desired in gene therapy to ensure efficient and targeted delivery of therapeutic genes. However, a major limitation of many AAV serotypes is their tendency to accumulate in the liver, leading to unwanted hepatic expression and potential off-target effects. Therefore, there is a critical need for vectors that not only exhibit strong tropism and transgene expression in the intended target tissue but also avoid expression in the liver.

As shown in the Examples, the present disclosure addresses this need by providing a viral vector and promoter that satisfies both criteria: it efficiently targets and expresses the therapeutic gene in the desired tissue, which is AT2 lung cells, while minimizing or eliminating expression in the liver. This can be observed especially in FIG. 9, where different AAV vectors are combined with different promoters. The only vector/promoter combination capable of 1) not having liver expression and 2) having lung specific expression is that which combines the AAV6.2 capsid with SpB promoter (a short lung-specific promoter). This vector design thus offers a great therapeutic opportunity for the treatment of specific lung diseases.

Additionally, this vector/promoter design offers specific expression in AT2 cells, as other lung cells that appear in scarring tissue, such as fibroblasts, do not express AAV6.2-SpB transgene, indicating that this vector/promoter combination has special and unique tropism for alveolar epithelial cells. These data demonstrate that use of the SpB promoter in combination with AAV6.2 capsid will silence or restrict expression in non-target cells, even those permissive to AAV transduction. Lastly, to demonstrate this effect regardless of the therapeutic gene expressed, hTERT expression was studied in primary AT2 cells using the vector AAV6.2-SpB-hTERT. As shown in FIG. 11, AT2 express therapeutic hTERT (hTERT-ID) after 5 days with AAV treatment.

In view of the above results, a first aspect of the present disclosure provides a recombinant adeno-associated virus particle (rAAV), also called herein the "rAAV particle of the invention", characterized in that:

a) it comprises a recombinant nucleic acid comprising a lung-specific SpB promoter comprising or consisting of SEQ ID NO: 1 and a therapeutic gene, wherein the lung-specific SpB promoter is operably linked to and regulates the expression of the therapeutic gene, and b) the AAV capsid is AAV6.2 serotype.

A "viral particle" or "virus particle" as used herein, means a small particle of about ten nanometers to about one micrometer, comprising a structural viral protein (such as a viral core protein), around which one or a plurality of nucleic acid molecules are contained. Viral particles comprise a group of particles called lipoparticles which include enveloped virus-like particles. In some preferred embodiments the enveloped virus-like particles comprise an enveloped viral core protein, a lipid bilayer, and an additional polypeptide on its surface. The viral particle may be about ten nm to about 500 nm, about 100 to about 500 nm, about 200 to about 400 nm, about 300 to about 399 nm, about 500 nm to about 1000 nm, about 600 to about 900 nm, or about 700 to about 800 nm. In some embodiments, the lipoparticle is dense, spherical, and/or homogeneous in size.

The virus particle Is a recombinant virus particle. As used herein, the term "recombinant virus particle" refers to a virus particle that has been genetically engineered to contain nucleic acid sequences (DNA or RNA or both) that do not naturally occur in that virus. In this case, the recombinant virus particle is an adeno-associated virus particle.

As used herein, an "adeno-associated virus particle" or "AAV particle" refers to a non-enveloped virus particle comprising a protein capsid that encapsidates nucleic acid sequences (DNA or RNA or both), typically approximately 4.7 kilobases in length, and is derived from or based on members of the Dependoparvovirus genus of the Parvoviridae family. It refers to a complete virus particle, such as for example a wild type AAV virion particle, which preferably comprises single stranded genome DNA packaged into AAV capsid proteins. The single stranded nucleic acid molecule is either sense strand or antisense strand, as both strands are equally infectious. The terms "adeno-associated virus", "AAV virus", "AAV virion", "AAV viral particle" and "AAV particle", are used as synonyms herein.

The disclosure provides an AAV virus particle comprising a recombinant nucleic acid sequence that does not naturally occur in that virus, so it is a recombinant AAV virus particle (rAAV particle of the invention).

The rAAV particle of the invention is composed of AAV proteins forming the capsid and a rAAV genome comprising a recombinant nucleic acid. The capsid proteins are from serotype 6.2, but the genome may be of a different serotype. Both elements are explained below.

The Capsid of the rAAV Particle of the Invention

The rAAV particle of the invention is composed of a protein shell, i.e. the icosahedral capsid, which comprises capsid viral proteins (viral proteins 1, 2, and/or 3, also called VP1, VP2, and/or VP3, respectively) of AAV serotype 6.2, whereas the rAAV genome contained in that AAV6.2 virion may be any of the rAAV vectors known in the art, including a rAAV6.2 vector. The rAAV particle of the invention comprises capsid proteins of AAV serotype 6.2, so it is also called the "rAAV6.2 particle of the invention".

"Subtype" or "serotype" as used herein, interchangeably, and in reference to AAV, means genetic variants of an AAV. As explained above, the rAAV particle of the invention is from serotype 6.2. In some embodiments the rAAV particle of the invention comprises a polypeptide comprising VP1, VP2 and VP3 from AAV serotype 6.2, or polypeptides that are at least 60%, 65%, 70%, 75%, 80%, 85%, 90%, 95%, 96%, 97%, 98% or 99% identical over the VPI, VP2, and/or VP3 polypeptides from AAV6.2.

The F129L mutation in VP1 protein in AAV6 creates a variant called AAV6.2. This mutation is a single nucleotide substitution where phenylalanine (F) at position 129 is replaced with leucine (L). This residue is part of the VP1 structural protein of the capsid. (Wu Z, Asokan A, Grieger J C, Govindasamy L, Agbandje-McKenna M, Samulski R J. Single amino acid changes can influence titer, heparin binding, and tissue tropism in different adeno-associated virus serotypes. J Virol. 2006 November; 80(22):11393-7. doi: 10.1128/JVI.01288-06. Epub 2006 Aug. 30. PMID: 16943302; PMCID: PMC1642158). Hence, the rAAV6.2 particle of the invention comprises a capsid proteins VP1, VP2, and VP3, wherein the VP1 protein comprises an F129L mutation. It is noted that here, and throughout the whole document, the positions or locations of the amino acid residues of a protein or a polypeptide sequence are numbered sequentially starting from the first amino acid residue which would then be located at position 1. For example, a protein of 450 amino acids will have those residues numbered 1 (first amino acid residue) until 450 (the last amino acid residue). Preferably, the first position or position number 1 corresponds to the first amino acid residue located at the 5-prime (5') end of the polypeptide chain that has a nitrogen atom or a free amino group. Thus, the numbering preferably starts from the first amino acid residue at the N terminal or 5' end of the protein or polypeptide and ends at the 3' end or C terminal end of the protein or polypeptide.

Preferably, the VP1 protein comprised in the rAAV6.2 particle of the invention comprises or consists of SEQ ID NO: 15, or a sequence with at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 15, with the proviso that the amino acid in position 129 is not a F, preferably with the proviso that the amino acid in position 129 is a L (F129L mutation). Preferably, the VP1 protein comprised in the rAAV6.2 particle of the invention is encoded by SEQ ID NO: 14 or a sequence with at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 14, with the proviso that the amino acid in position 129 is not a F, preferably with the proviso that the amino acid in position 129 is a L.

The Genome of the rAAV Particle of the Invention

As explained above, the rAAV6.2 particle of the invention comprises a genome that comprises a recombinant nucleic acid sequence. Said recombinant nucleic acid sequence is formed by at least a promoter and a therapeutic gene whose expression is driven by said promoter.

"Promoter" as used herein means a synthetic nucleotide sequence that is capable of conferring, activating or enhancing expression of a therapeutic gene in a cell. It comprises transcriptional regulatory sequences to drive the expression and/or to alter the spatial expression and/or temporal expression of said therapeutic gene.

In the rAAV6.2 particle of the invention, the promoter is a lung-specific promoter. A "lung-specific promoter" is a promoter that is capable of initiating transcription in the lung and/or a lung tissue and/or a lung cell. Said promoter may or may not still allow leaky expression in other organs and parts of the body. "Lung-specific" also encompasses promoters that drive the preferential or predominant expression of a nucleotide sequence in the lung and/or a lung tissue and/or a lung cell as compared to other organs, tissues or cells as described later herein. Transcription in the lung can be detected in relevant areas, such as the trachea, bronchi, pleura, diaphragm, bronchioles, alveoli or epithelium. Promoters that are capable of initiating transcription in cells of the lung epithelium are advantageous. A lung-specific promoter may be a promoter that is capable of driving the preferential or predominant expression of a nucleotide sequence in the lungs as compared to one or more tissues and/or organs selected from the brain, adipose tissue (white and/or brown), heart and/or liver, preferably brain, brown adipose tissue and/or heart. Preferably, the promoter is capable of initiating transcription in alveolar type II epithelial cells (ATII or AT2 cells). Accordingly, the lung-specific promoter may be an alveolar type II epithelial cell specific (ATII-cell specific) promoter.

The promoter comprised in the recombinant nucleic acid sequence is a lung-specific SpB promoter, more specifically the promoter comprising or consisting of SEQ ID NO: 1, or a functional equivalent thereof. A "functional equivalent promoter" refers to any promoter sequence that, although not identical in sequence to SEQ ID NO: 1, is capable of driving transcription of a gene or nucleic acid sequence in a manner comparable to the referenced promoter, either in strength, regulation, or tissue specificity. As used in this context, "a manner comparable to" means that the functional equivalent promoter is capable of driving transcription of a gene or nucleic acid sequence about, around, or approximately the same in strength, regulation, and/or tissue specificity as SEQ ID NO: 1.

As explained above, the recombinant nucleic acid sequence comprised in the genome of the rAAV6.2 particle of the invention also comprises a therapeutic gene encoding for a therapeutic protein. The term "therapeutic" is used in a generic sense and includes treating agents, prophylactic agents, replacement agents and diagnostic agents. A therapeutic agent such as a therapeutic protein may be considered therapeutic if it improves or prevents at least one symptom of a disease or medical condition. Hence, lung diseases may be treated with the rAAV6.2 particle of the invention, as will be explained below.

In the recombinant nucleic acid, the therapeutic gene is operably linked to and regulated by the lung-specific SpB promoter comprising or consisting of SEQ ID NO: 1. "Operably linked", as used herein, means that expression of the therapeutic gene is under the control of the promoter of SEQ ID NO: 1, with which it is spatially connected. It refers to a linkage of polynucleotide elements in a functional relationship. For instance, a transcription regulatory sequence is operably linked to a coding sequence if it affects the transcription of the coding sequence. The promoter of SEQ ID NO: 1 may be positioned 5' (upstream) or 3' (downstream) of the therapeutic gene under its control. As is known in the art, variation in this distance may be accommodated without loss of promoter function. The phrases "operably linked," "under control," and "under transcriptional control" thus mean that the promoter of SEQ ID NO:

1 is in a correct functional location and/or orientation in relation to the therapeutic gene, to control transcriptional initiation and/or expression of that gene.

In an embodiment, the therapeutic gene encodes for the telomerase reverse transcriptase (TERT). A "telomerase reverse transcriptase" or "TERT", alternatively known as TP2, TRT, EST2, or TCS1 (EC 2.7.7.49) is a catalytic component of the telomerase holoenzyme complex, whose main activity is the elongation of telomeres by its acting as a reverse transcriptase that adds simple sequence repeats to chromosome ends by copying a template sequence within the ncRNA component of the enzyme (Terc, telomerase RNA component). TERT catalyzes the RNA-dependent extension of 3'-chromosomal termini with the 6-nucleotide telomeric repeat unit 5'-TTAGGG-3'. The skilled person understands that the term also encompasses modified versions of TERT, such as but not limited to TERT fragments, as long as said modified versions remain functional. In this context, functionality refers to the modified protein exhibiting at least 20%, at least 30%, at least 40%, at least 50%, at least 60%, at least 70%, at least 80%, at least 90%, or at least 95%, of the catalytic activity as compared to the unmodified protein. A modified version of TERT may also exhibit increased functionality as compared to the unmodified protein. In this context, increased functionality refers to the modified protein exhibiting at least 105%, at least 110%, at least 120%, at least 130%, at least 140%, at least 150%, at least 160%, at least 170%, at least 180%, at least 190%, or at least 200% of the catalytic activity as compared to the unmodified protein.

In some embodiments, the therapeutic gene encodes a TERT of mammalian origin. In some embodiments, the therapeutic gene encodes a TERT of murine, leporid, swine, equine, sheep, bovine, feline, canine, or human origin. In humans, two TERT isoforms exist which differ in length; a long isoform (NCBI CCDS ID: 3861.2) and a short isoform (NCBI CCDS ID: 54831.1). In some embodiments, the therapeutic gene encoding a TERT is of murine (such as mouse or rat) or human origin, preferably of human origin, more preferably it is the long or short isoform of human TERT or a modified version thereof.

Preferably, the human TERT (hTERT) comprises or consists of SEQ ID NO: 2 or 3, or a sequence with at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 2 or 3, respectively. Most preferably, the therapeutic protein comprises or consists of SEQ ID NO: 2.

Preferably, the therapeutic gene comprises or consists of SEQ ID NO: 8 (wildtype long hTERT), 9 (wildtype short hTERT), 11 (hTERT-ID), 12 (hTERT-GA), or 13 (hTERT_GS), or a sequence with at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 8, 9, 11, 12, or 13, respectively. Most preferably, the therapeutic protein comprises or consists of SEQ ID NO: 11.

Thus, in a preferred embodiment, the rAAV6.2 particle of the invention comprises a recombinant nucleic acid sequence comprising a promoter and a therapeutic gene encoding for a therapeutic protein, wherein the promoter comprises or consists of SEQ ID NO: 1, wherein the therapeutic protein is hTERT protein, and wherein the promoter is operably linked to and regulates the expression of said hTERT protein. Even more preferably, the rAAV6.2 particle of the invention comprises a recombinant nucleic acid sequence comprising a promoter and a therapeutic gene, wherein the promoter comprises or consists of SEQ ID NO: 1, wherein the therapeutic gene comprises SEQ ID NO: 11, and wherein the promoter is operably linked to and regulates the expression of said therapeutic gene.

The genome of the rAAV6.2 particle of the invention comprising the recombinant nucleic acid may have other elements that participate, directly or indirectly, in the expression of the therapeutic gene. Thus, the genome of the rAAV6.2 particle of the invention may further comprise additional nucleotide sequences that are operably linked to the nucleotide sequence encoding the therapeutic gene, such as, but not limited to, signal sequences, nuclear localization signals, expression enhancers, polyadenylation signals, Kozak sequences and the like. Said sequences may or may not correspond to sequences that are native to a cell wherein the recombinant viral genome comprising said promoter is to be introduced in.

For example, the efficiency of expression may be enhanced by the inclusion of appropriate transcription enhancer elements. "Enhancer" refers to a cis-acting regulatory sequence involved in the transcriptional activation of a nucleic acid sequence.

Internal ribosome entry sites (IRES) elements may also be included in the genome of the rAAV6.2 particle of the invention to create multigene, or polycistronic, constructs. Multiple cloning site (MCS), which is a nucleic acid region that contains multiple restriction enzyme sites, can also be included in the genome of the rAAV6.2 particle of the invention to digest the recombinant nucleic acid. Transcriptional termination sites can also be included in the genome of the rAAV6.2 particle of the invention to enhance message levels and/or to minimize read through from the cassette into other sequences.

At least a polyadenylation signal or polyA sequence may also be included in the genome of the rAAV6.2 particle of the invention. A "polyadenylation sequence", alternatively referred to herein as a "polyA sequence" or "polyA tail", is a nucleotide sequence consisting of a stretch of multiple adenosine monophosphates that can enhance the expression of nucleotide sequences it is operably linked to by enhancing nuclear export, translation and/or stability of mRNA sequences. The polyA sequence enhances mRNA stability, nuclear export, and translation efficiency. It is preferably placed downstream the therapeutic gene. Thus, in some embodiments, the genome of the rAAV6.2 particle of the invention comprises a polyA sequence operably linked to the therapeutic gene, preferably to the gene encoding TERT. The nature of the polyadenylation signal is not believed to be crucial to the successful practice of the invention, and/or any such sequence may be employed. Preferred polyA sequences include the SV40 polyadenylation signal and/or the bovine growth hormone polyadenylation signal. Preferably, the polyA sequence is the bovine growth hormone polyadenylation signal. Preferably, the polyA sequence comprises or consists of SEQ ID NO: 5, or a sequence with at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 5.

A Kozak may also be included in the genome of the rAAV6.2 particle of the invention. A "Kozak sequence", alternatively referred to herein as a Kozak consensus sequence, is a nucleic acid motif that functions as the protein translation initiation site and can enhance the expression of nucleotide sequences it is operably linked to. The Kozak sequence comprises a consensus sequence surrounding the start codon (typically AUG) and is recognized by the ribosomal machinery to facilitate efficient translation initiation.

In some embodiments, the genome of the rAAV6.2 particle of the invention comprises a Kozak consensus sequence operably linked to the therapeutic gene, preferably to the gene encoding TERT. It is preferably placed upstream the therapeutic gene. Preferably, the Kozak sequence comprises or consists of SEQ ID NO: 4, or a sequence with at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 4.

The rAAV genome of the rAAV6.2 particle of the invention may have one or more wild type AAV genes deleted, but still comprise functional ITR nucleic acid sequences. Functional ITR sequences are necessary for the replication, rescue and packaging of AAV virions. The ITR sequences may be wild type sequences or substantially identical sequences or may be altered by for example in insertion, mutation, deletion or substitution of nucleotides, as long as they remain functional. The recombinant nucleic acid can be inserted between the AAV ITR sequences. Inverted terminal repeats may be included at the 5' and the 3' flanks (5' ITR and 3' ITR, respectively) of the recombinant nucleic acid. Suitable inverted terminal repeat sequences may be derived from any adeno-associated virus serotype, such as but not limited to AAV1, preferably AAV2, AAV3, AAV4, AAV5, AAV6, and others. Preferably, the ITRs are those of AAV2 which are represented by sequences comprising or consisting of SEQ ID NO: 6 (5' ITR) and SEQ ID NO: 7 (3' ITR), or a sequence with at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 6 or 7, respectively.

The rAAV genome of the rAAV6.2 particle of the invention may further comprise a marker or reporter gene, such as a gene for example encoding an antibiotic resistance gene, a fluorescent protein (e.g. GFP) or a gene encoding a chemically, enzymatically or otherwise detectable and/or selectable product known in the art.

Preferably, the recombinant nucleic acid comprised in the rAAV6.2 particle of the invention comprises or consist of SEQ ID NO: 10, or a sequence with at least 50%, 60%, 70%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 10.

Preferred rAAV6.2 Particle of the Invention

In view of the above, preferred rAAV6.2 particles of the invention are:

In an embodiment, the rAAV particle of the invention has a capsid of 6.2 serotype, and a genome comprising a recombinant nucleic acid comprising a promoter and a therapeutic gene, wherein the promoter comprises or consists of SEQ ID NO: 1, and wherein the promoter is operably linked to and regulates the expression of the therapeutic gene.

In an embodiment, the rAAV particle of the invention has a capsid of 6.2 serotype, and a genome comprising a recombinant nucleic acid comprising a promoter and a therapeutic gene, wherein the promoter consists of SEQ ID NO: 1, wherein the therapeutic gene encodes for human TERT protein, and wherein the promoter is operably linked to and regulates the expression of the therapeutic gene.

In an embodiment, the rAAV particle of the invention has a capsid of 6.2 serotype, and a genome comprising a recombinant nucleic acid comprising a promoter and a therapeutic gene, wherein the promoter consists of SEQ ID NO: 1, wherein the therapeutic gene encodes for human TERT protein comprising SEQ ID NO: 2 or 3, and wherein the promoter is operably linked to and regulates the expression of the therapeutic gene.

In an embodiment, the rAAV particle of the invention has a capsid of 6.2 serotype, and a genome comprising a recombinant nucleic acid comprising a promoter and a therapeutic gene, wherein the promoter consists of SEQ ID NO: 1, wherein the therapeutic gene encodes for human TERT protein comprising or consisting of SEQ ID NO: 2, and wherein the promoter is operably linked to and regulates the expression of the therapeutic gene.

In an embodiment, the rAAV particle of the invention has a capsid of 6.2 serotype comprising a VP1 comprising SEQ ID NO: 14, and a genome comprising a recombinant nucleic acid comprising a promoter and a therapeutic gene, wherein the promoter consists of SEQ ID NO: 1, wherein the therapeutic gene encodes for human TERT protein, and wherein the promoter is operably linked to and regulates the expression of the therapeutic gene.

In an embodiment, the rAAV particle of the invention has a capsid of 6.2 serotype comprising a VP1 comprising SEQ ID NO: 14, and a genome comprising a recombinant nucleic acid comprising a promoter and a therapeutic gene, wherein the promoter consists of SEQ ID NO: 1, wherein the therapeutic gene comprises SEQ ID NO: 8, 9, 11, 12, or 13, and wherein the promoter is operably linked to and regulates the expression of the therapeutic gene.

In an embodiment, the rAAV particle of the invention has a capsid of 6.2 serotype comprising a VP1 comprising SEQ ID NO: 14, and a genome comprising a recombinant nucleic acid comprising a promoter and a therapeutic gene, wherein the promoter consists of SEQ ID NO: 1, wherein the therapeutic gene comprises SEQ ID NO: 11, and wherein the promoter is operably linked to and regulates the expression of the therapeutic gene.

In an embodiment, the rAAV particle of the invention has a capsid of 6.2 serotype, and a genome comprising a recombinant nucleic acid comprising or consisting of SEQ ID NO: 10.

Methods to Produce the rAAV6.2 Particle of the Invention

Method for producing the rAAV6.2 particle of the invention are also provided herein. Methods for the production of rAAV particles of serotype 6.2 are known in the art. These protocols can be used or adapted to generate an rAAV6.2 particle of the invention.

In short, the methods generally involve (a) the introduction of the AAV6.2 genome comprising the recombinant nucleic acid sequence as defined above, (b) the presence or introduction of an AAV helper construct in the cell, wherein the helper construct comprises the viral functions missing from the recombinant AAV genome and, optionally, (c) the introduction of a helper virus and/or helper virus plasmid into the host cell. All components for AAV6.2 vector replication and packaging need to be present, to achieve replication and packaging of the genome into AAV6.2 vectors. These typically include AAV6.2 cap proteins, AAV6.2 rep proteins and, optionally, viral proteins upon which AAV6.2 is dependent for replication. Rep and cap regions are well known in the art. The viral proteins upon which AAV6.2 is dependent for replication may derive from any virus, such as a herpes simplex viruses (such as HSV types 1 and 2), a vaccinia virus, an adeno-associated virus or an adenovirus, preferably from an adenovirus.

In some embodiments, the producer cell line is transfected transiently with a AAV6.2 genome comprising the recombinant nucleic acid sequence as defined above and with construct(s) that encode(s) rep and cap proteins and provide (s) helper functions (helper construct(s)). In some embodiments, the cell line supplies stably one or more of said elements, so that a transient transfection is not needed for said element. For example, the cell may stably express the helper functions and is transfected transiently with the recombinant AAV6.2 genome comprising the recombinant nucleic acid sequence as defined above and with construct(s) that encode(s) rep and cap proteins. Methods of making and using these and other AAV production systems have been described in the art. The introduction into a producer cell can be carried out using standard virological techniques, such as transformation, transduction and transfection.

The rAAV6.2 particle of the invention may then require co-infection with a helper virus (such as adenovirus or herpesvirus) for productive replication in host cells. "AAV helper functions" generally refers to the corresponding AAV functions required for rAAV replication and packaging supplied to the rAAV virion or rAAV vector in trans. AAV helper functions complement the AAV functions which are missing in the rAAV virus particle, but they lack AAV ITRs (which are provided by the rAAV virus particle). AAV helper functions include the two major ORFs of AAV, namely the rep coding region and the cap coding region or functional substantially identical sequences thereof. Rep and Cap regions are well known in the art. The AAV helper functions can be supplied on a AAV helper construct. Introduction of the helper construct by into the host cell can occur e.g. by transformation or transduction prior to or concurrently with the introduction of the rAAV vector.

The Cell of the Invention

In a second aspect, the present invention provides a cell comprising the rAAV6.2 particle of the invention, or its genome according to the first aspect or any of its embodiments. Said cell, also called herein the "cell of the invention", may be a mammalian cell, preferably a human cell. In some embodiments, the cell is transduced with the rAAV6.2 particle of the invention, or its viral genome, and is a lung cell, such as a lung cell of a vertebrate, preferably a lung cell of a mammal. Preferably, the cell is human cell found in the interstitial space of the lungs. Preferably, the cell is an alveolar cell, preferably Type I or Type II alveolar cells, or a progenitor thereof. Preferably, the cell comprising the rAAV6.2 particle of the invention or its genome is a Type II alveolar cell, also called type II pneumocytes, which are specialized epithelial cells found in the alveoli of the lungs.

The Composition of the Invention

In a third aspect, the present invention provides a composition, preferably a pharmaceutical composition, comprising the rAAV6.2 particle of the invention as defined in the first aspect, or the cell of the invention as defined in the second aspect, or any of their embodiments. The composition is algo called herein the "composition of the invention", and it may include pharmaceutically acceptable excipients or carriers.

Pharmaceutically acceptable excipients include, but are not limited to a carrier or diluent, such as a gum, a starch (e.g. corn starch, pregelatinized starch), a sugar (e.g. lactose, mannitol, sucrose, dextrose), a cellulosic material (e.g. microcrystalline cellulose), an acrylate (e.g. polymethylacrylate), calcium carbonate, magnesium oxide, talc, or mixtures thereof; a binder (e.g. acacia, cornstarch, gelatin, carbomer, ethyl cellulose, guar gum, hydroxypropyl cellulose, hydroxypropyl methyl cellulose, povidone); a disintegrating agent (e.g. cornstarch, potato starch, alginic acid, silicon dioxide, croscarmellose sodium, crospovidone, guar gum, sodium starch glycolate), a buffer (e.g. Tris-HCl, acetate, phosphate, bicarbonate) of various pH and ionic strength; and additive such as albumin or gelatin to prevent absorption to surfaces; a detergent (e.g. Tween 20, Tween 80, Pluronic F68, bile acid salts); a protease inhibitor; a surfactant (e.g. sodium lauryl sulfate); a permeation enhancer; a solubilizing agent (e.g. glycerol, polyethylene glycerol); an antioxidants (e.g. ascorbic acid, sodium metabisulfite, butylated hydroxyanisole); a stabilizer (e.g. hydroxypropyl cellulose, hydroxypropylmethyl cellulose); a viscosity increasing agent (e.g. carbomer, colloidal silicon dioxide, ethyl cellulose, guar gum); a sweetener (e.g. aspartame, citric acid); a preservative (e.g. thimerosal, benzyl alcohol, parabens); a lubricant (e.g. stearic acid, magnesium stearate, polyethylene glycol, sodium lauryl sulfate); a flow-aid (e.g. colloidal silicon dioxide), a plasticizer (e.g. diethyl phthalate, triethyl citrate); an emulsifier (e.g. carbomer, hydroxypropyl cellulose, sodium lauryl sulfate); a polymer coating (e.g. poloxamers or poloxamines); a coating and film forming agent (e.g. ethyl cellulose, acrylates, polymethacrylates); a pharmaceutically acceptable carrier for liquid formulations, such as an aqueous (water, alcoholic/aqueous solution, emulsion or suspension, including saline and buffered media) or non-aqueous (e.g., propylene glycol, polyethylene glycol, and injectable organic esters, such as ethyl oleate) solution, suspension, emulsion or oil; and a parenteral vehicle (e.g., for subcutaneous, intravenous, intraarterial, or intramuscular injection), including but not limited to, water, oils, saline solution, Ringer's dextrose, aqueous dextrose and other sugar solutions. A pharmaceutically acceptable excipient also includes excipients for nanoencapsulation purposes, such as a cationic polyelectrolyte (e.g. gelatin and an anionic polyelectrolyte (e.g. arabic gum).

In some embodiments, the pharmaceutical composition further comprises other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, composition is administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The Kit of the Invention

In a fourth aspect, the present invention refers to a kit, also called hereinafter "the kit of the invention", comprising the rAAV6.2 particle of the invention as defined in the first aspect, the cell of the invention as defined in the second aspect, the composition of the invention as defined in the third aspect, or any of their embodiments. The kit may comprise the rAAV6.2 particle of the invention and also include one or more reagents for introducing it into a cell, preferably into the cell of the invention.

The kit may further instructions for making the cells of the invention, or therapeutic applications of them, such as information as to dosage, dosing schedule, and route of administration for the intended treatment.

The kits provided herein are in suitable packaging. Suitable packaging includes, but is not limited to, vials, bottles, jars, flexible packaging, and the like. Also contemplated are packages for use in combination with a specific device, such as an infusion device for administration of the elements of the invention, or to produce the rAAV6.2 particle or the cells of the invention. A kit may have a sterile access port (for example, the container may be an intravenous solution bag or a vial having a stopper pierceable by a hypodermic injection needle). The container may also have a sterile access port.

Therapeutic Uses of the Invention

In a fifth aspect, the present invention provides therapeutic uses of the rAAV6.2 particle of the invention as defined in the first aspect, the cell of the invention as defined in the second aspect, the composition of the invention as defined in the third aspect, the kit of the invention as defined in the fourth aspect, or any of their embodiments. Said uses may be in medicine, or as a medicament, or in methods for treatment a subject in need thereof. The term "medicament" describes a drug or combination of drugs that have the ability to treat diseases, disorders or conditions in subjects or that they can be used in subjects with the aim of restoring, correcting or modifying the physiological functions performing a pharmacological, immunological or metabolic function. The terms "medicament" and "medication" are used herein interchangeably. The term "subject" as used herein refers to a mammalian subject, preferably a human.

Preferably, the use of the fifth aspect is in the treatment of a subject having a lung disease, since the promoter of SEQ ID NO: 1 is a lung-specific promoter, so that the therapeutic gene will be specifically expressed in lung cells adjacent to the interstitial space, preferably AT2 cells. Hence, the rAAV6.2 particle, the cell, the kit and the composition of the invention are useful in treating lung diseases, preferably interstitial lung diseases that result in scarring and inflammation in the interstitial space, more preferably diseases involving AT2 cells. Preferably, the lung disease is a disease affecting the interstitial part of the lungs, the region surrounding the alveoli (also called Interstitial lung diseases (ILDs)). The "interstitial part of the lung," or "pulmonary interstitium," refers to the complex, connective tissue network located between and around the alveoli, bronchioles, blood vessels, and lymphatics. This compartment comprises extracellular matrix components (e.g., collagen, elastin, proteoglycans), interstitial fluid, fibroblasts, resident immune cells, and structural cells that provide mechanical support, elasticity, and mediate biochemical signalling. It also facilitates gas exchange indirectly by maintaining the architecture and function of alveolar-capillary units.

Preferably, the lung disease is a disease affecting Type II alveolar cells (AT2 cells), particularly their regenerative capacity. Preferably, the lung disease is pulmonary fibrosis, more preferably idiopathic pulmonary fibrosis (IPF). Pulmonary fibrosis refers to a condition characterised by scarring of the lung tissue. Pulmonary fibrosis can be caused by many factors, including, but not limited to, lung cell telomere shortening, chronic inflammatory processes, infections, environmental compounds, ionizing radiation (for example radiation therapy to treat tumours of the chest), genetic predisposition, or chronic medical conditions (lupus, rheumatoid arthritis and others). Pulmonary fibrosis includes idiopathic pulmonary fibrosis (IPF), which refers to pulmonary fibrosis without an identifiable cause. Symptoms of pulmonary fibrosis include, but are not limited to, lung scarring, development of fibrotic volume, loss of lung volume, shortness of breath, dry cough, fatigue, weight loss, and nail clubbing. Conditions associated with pulmonary fibrosis include, but are not limited to, pulmonary hypertension, respiratory failure, pneumothorax, and lung cancer. In some embodiments, a treatment or a therapy or a use or the administration of a medicament for the treatment of a pulmonary fibrosis or a condition associated therewith alleviates, removes and/or prevents a symptom and/or improves a parameter associated therewith selected from the group consisting of lung scarring, development of fibrotic volume, loss of lung volume, shortness of breath, dry cough, fatigue, weight loss, and nail clubbing, preferably development of fibrotic volume and/or loss of lung volume.

Thus, the subject to be treated by the elements of the invention (rAAV6.2 particle, the cell, the composition, or the kit of the invention) may preferably be a human subject having a lung disease, preferably a disease affecting the pulmonary interstitium, more preferably a disease affecting Type II alveolar cells. Preferably, the subject has been diagnosed with pulmonary fibrosis, more preferably idiopathic pulmonary fibrosis (IPF).

In an embodiment, the rAAV6.2 particle of the invention comprises a nucleic acid encoding for TERT, and it is used in treating and/or preventing conditions associated with shortened telomere length, preferably conditions associated with shortened telomere length that affects the lungs. "Shortened telomeres" or "short telomeres" generally refers to telomeres below a certain length, e.g. 8 kb, 7 kb, 6 kb, 5 kb, or shorter. Typically, shortened telomeres have a length that is below the 20th or 10th percentile of the telomere length of a population of healthy individuals belonging to a certain age group, which indicates the telomere length below which 20% or 10% of the telomeres fall. Conversely, long telomeres typically have a length that is above the 80th or 90th percentile of the telomere length of a population of healthy individuals belonging to a certain age group. Telomere length may be assessed in samples taken directed from a treated individual, or a cell, tissue, and/or organ of a treated individual, according to generally known methods in the art. For example, standard hybridization techniques, such as fluorescence in situ hybridization (FISH), quantitative fluorescent in situ hybridization (Q-FISH), or high throughput quantitative fluorescent in situ hybridization (HT Q-FISH). Telomere length may also be inferred by monitoring the deterioration of or the improvement in a symptom and/or a parameter of a condition associated with shortened telomere length as discussed elsewhere herein using standard procedures in the art.

Samples may be taken throughout the course of the treatment so that both absolute telomere length and the rate of telomere lengthening or shortening over the course of treatment can be determined. Samples may be taken every day during the course of treatment, or at longer intervals. In some embodiments, samples are taken once a week, once every two weeks, once every three weeks, once every four weeks, once every five weeks, once every six weeks or at longer intervals. Comparisons of telomere length can be made by comparing the proportion of shortened telomeres in the taken samples. The proportion of shortened telomeres may be assessed by measuring the fraction of telomeres presenting an intensity below the mean intensity of the sample as measured by an in situ hybridization technique, such as FISH or Q-FISH. In some embodiments, the proportion of shortened telomeres is the fraction of telomeres presenting an intensity 75%, 70%, 65%, 60%, 55%, 50%, 45%, 40% or lower as compared to the mean intensity of the sample. In some embodiments, the proportion of shortened telomeres in a sample taken directed from a treated individual, or a cell, tissue, and/or organ of a treated individual, is decreased by 10%, 20%, 30%, 40%, 50%, 60%, 70%, or greater as compared to a control sample. A control sample may be taken from the individual to be treated, or a cell, tissue, and/or organ of an individual to be treated prior to commencement of the treatment and/or from an untreated individual suffering from the same condition, or a cell, tissue, and/or organ of an untreated individual suffering from the same condition.

Most preferably, the rAAV6.2 particle, the cell, the composition, or the kit of the invention as defined in any of the aspects above or any of their embodiments are used to treat a lung disease, preferably pulmonary fibrosis, more preferably idiopathic pulmonary fibrosis (IPF), wherein the rAAV6.2 particle comprises a recombinant nucleic acid comprising a promoter as set forth in SEQ ID NO: 1, that is operably linked and regulates the expression of a therapeutic gene encoding for human TERT.

In some embodiments, there is provided a method of treatment and/or prevention of a lung condition associated with shortened telomere length, preferably of pulmonary fibrosis, more preferably IPF, the method comprising administering to a subject in need thereof a therapeutically effective amount of the rAAV particle of the invention encoding for TERT as defined in the first aspect or any of its embodiments. An "effective amount" refers to the amount the elements of the invention needed to treat or alleviate at least one or more signs or symptoms of a medical condition (e.g., pulmonary fibrosis), and relates to a sufficient amount to provide the desired effect, e.g., to treat a subject having a medical condition.

Hence, the rAAV6.2 particle, cell, composition or kit of the invention can be administrated to the subject for therapeutic purposes, i.e., preferably for the treatment of pulmonary diseases.

The use may include administering any of the elements of the invention (the rAAV6.2 particle, the cell, the composition, and the kit) in a subject in need thereof. The step of administering can be performed by any appropriate route that results in delivery of the elements of the invention to a desired location in the subject. In an embodiment, an effective amount of said elements of the invention is administrated to the subject. The period of viability of the elements of the invention after administration to a subject can be as short as a few hours, e.g., twenty-four hours, to a few days, to as long as several years, or even the lifetime of the subject, i.e., long-term engraftment. For example, in some embodiments described herein, an effective amount of the rAAV particle or cells can be administered via a systemic route of administration, such as an intraperitoneal or intravenous route.

In some embodiments, the elements of the invention are administered systemically, which refers to the administration other than directly into a target site, tissue, or organ, such that it enters, instead, the subject's circulatory system and, thus, is subject to metabolism and other like processes. Suitable modes of administration include injection, infusion, instillation, or ingestion. Injection includes, without limitation, intravenous, intramuscular, intra-arterial, intrathecal, intraventricular, intracapsular, intraorbital, intracardiac, intradermal, intraperitoneal, transtracheal, subcutaneous, subcuticular, intraarticular, subcapsular, subarachnoid, intraspinal, intracerebrospinal, and intrasternal injection and infusion. In some embodiments, the route is intravenous.

Lastly, additional uses are also encompassed within the scope of this invention, depending on the nature of the therapeutic protein encoded by the therapeutic gene. As noted above, the term "therapeutic" is used in a broad sense and includes agents for treatment, prophylaxis, replacement, and diagnosis. Accordingly, the rAAV6.2 particle, the cell, the composition, and the kit described herein may serve as therapeutic, prophylactic, replacement, or diagnostic agents, provided that the therapeutic gene encodes a protein relevant to such applications.

The present invention also comprises the following items:
1. A recombinant adeno-associated virus (rAAV) particle characterized in that:
   a) it comprises a recombinant nucleic acid comprising a lung-specific SpB promoter and a therapeutic gene, wherein the lung-specific promoter comprises SEQ ID NO: 1, and wherein said promoter is operably linked to and regulates the expression of the therapeutic gene, and
   b) it comprises an AAV capsid of 6.2 serotype.
2. The rAAV particle of item 1, wherein the therapeutic gene encodes for human telomerase reverse transcriptase (TERT).
3. The rAAV particle of item 1 or 2, wherein the therapeutic gene encodes a protein comprising SEQ ID NO: 2 or 3.
4. The rAAV particle of items 1 to 3, wherein the AAV capsid of 6.2 serotype comprises a VP1 protein comprising SEQ ID NO: 15.
5. The rAAV particle of item 1 to 4, wherein the therapeutic gene comprises SEQ ID NO: 8, 9, 11, 12, or 13, preferably SEQ ID NO: 11.
6. The rAAV particle of any one of items 1 to 5, wherein the recombinant nucleic acid of a) further comprises a Kozak sequence upstream of the therapeutic gene.
7. The rAAV particle of item 6, wherein the Kozak sequence comprises SEQ ID NO: 4.
8. The rAAV particle of any one of items 1 to 7, wherein the recombinant nucleic acid of a) further comprises a polyadenylation (Poly-A) signal, preferably the bovine growth hormone polyadenylation signal, placed downstream the therapeutic gene.
9. The rAAV particle of any one of items 1 to 8, wherein the recombinant nucleic acid of a) further comprises a 5' and 3'-end inverted terminal repeat (ITR) sequences from AAV serotype 2 (AAV2).
10. The rAAV particle of item 9, wherein the 5' and 3'-end AAV2 ITR sequences comprise SEQ ID NO: 6 and 7, respectively.
11. The rAAV particle of any one of items 1 to 10, wherein the recombinant nucleic acid of a) comprises or consists of SEQ ID NO: 10.
12. The rAAV particle of any one of items 1 to 11, for use in medicine.
13. The rAAV particle of any one of items 1 to 11, for use in the treatment or prevention of lung diseases.
14. The rAAV particle of any one of items 2 to 11, for use in the treatment or prevention of pulmonary fibrosis.
15. The rAAV particle for use according to item 14, wherein the pulmonary fibrosis is idiopathic pulmonary fibrosis.

SEQUENCE LISTING
SEQ ID NO: 1: SpB short promoter
ATAGGGCTGTCTGGGAGCCACTCCAGGGCCACAGAAATCTTGTCTCTGACTCAGGGTATTTT

GTTTTCTGTTTTGTGTAAATGCTCTTCTGACTAATGCAAACCATGTGTCCATAGAACCAGAAG

ATTTTTCCAGGGGAAAAGGTAAGGAGGTGGTGAGAGTGTCCTGGGTCTGCCCTTCCAGGGC

TTGCCCTGGGTTAAGAGCCAGGCAGGAAGCTCTCAAGAGCATTGCTCAAGAGTAGAGGGGG

-continued

CCTGGGAGGCCCAGGGAGGGGATGGGAGGGGAACACCCAGGCTGCCCCCAACCAGATGC

CCTCCACCCTCCTCAACCTCCCTCCCACGGCCTGGAGAGGTGGGACCAGGTATGGAGGCTT

GAGAGCCCCTGGTTGGAGGAAGCCACAAGTCCAGGAACATGGGAGTCTGGGCAGGGGGCA

AAGGAGGCAGGAACAGGCCATCAGCCAGGACAGGTGGTAAGGCAGGCAGGAGTGTTCCTG

CTGGGAAAAGGTGGGATCAAGCACCTGGAGGGCTCTTCAGAGCAAAGACAAACACTGAGGT

CGCTGCCACTCCTACAGAGCCCCCACGCCCCGCCCAGCTATAAGGGGCCATGCACCAAGC

AGGGTACCCAGGCTGCAGAGGTGC

SEQ ID NO: 2 human TERT long isoform protein sequence
MPRAPRCRAVRSLLRSHYREVLPLATFVRRLGPQGWRLVQRGDPAAFRALVAQCLVCVPWDA

RPPPAAPSFRQVSCLKELVARVLQRLCERGAKNVLAFGFALLDGARGGPPEAFTTSVRSYLPNT

VTDALRGSGAWGLLLRRVGDDVLVHLLARCALFVLVAPSCAYQVCGPPLYQLGAATQARPPPH

ASGPRRRLGCERAWNHSVREAGVPLGLPAPGARRRGGSASRSLPLPKRPRRGAAPEPERTPV

GQGSWAHPGRTRGPSDRGFCVVSPARPAEEATSLEGALSGTRHSHPSVGRQHHAGPPSTSRP

PRPWDTPCPPVYAETKHFLYSSGDKEQLRPSFLLSSLRPSLTGARRLVETIFLGSRPWMPGTPR

RLPRLPQRYWQMRPLFLELLGNHAQCPYGVLLKTHCPLRAAVTPAAGVCAREKPQGSVAAPEE

EDTDPRRLVQLLRQHSSPWQVYGFVRACLRRLVPPGLWGSRHNERRFLRNTKKFISLGKHAKL

SLQELTWKMSVRDCAWLRRSPGVGCVPAAEHRLREEILAKFLHWLMSVYVVELLRSFFYVTETT

FQKNRLFFYRKSVWSKLQSIGIRQHLKRVQLRELSEAEVRQHREARPALLTSRLRFIPKPDGLRPI

VNMDYVVGARTFRREKRAERLTSRVKALFSVLNYERARRPGLLGASVLGLDDIHRAWRTFVLRV

RAQDPPPELYFVKVDVTGAYDTIPQDRLTEVIASIIKPQNTYCVRRYAVVQKAAHGHVRKAFKSH

VSTLTDLQPYMRQFVAHLQETSPLRDAVVIEQSSSLNEASSGLFDVFLRFMCHHAVRIRGKSYVQ

CQGIPQGSILSTLLCSLCYGDMENKLFAGIRRDGLLLRLVDDFLLVTPHLTHAKTFLRTLVRGVPE

YGCVVNLRKTVVNFPVEDEALGGTAFVQMPAHGLFPWCGLLLDTRTLEVQSDYSSYARTSIRAS

LTFNRGFKAGRNMRRKLFGVLRLKCHSLFLDLQVNSLQTVCTNIYKILLLQAYRFHACVLQLPFH

QQVWKNPTFFLRVISDTASLCYSILKAKNAGMSLGAKGAAGPLPSEAVQWLCHQAFLLKLTRHR

VTYVPLLGSLRTAQTQLSRKLPGTTLTALEAAANPALPSDFKTILD

SEQ ID NO: 3 human TERT short isoform protein sequence
MPRAPRCRAVRSLLRSHYREVLPLATFVRRLGPQGWRLVQRGDPAAFRALVAQCLVCVPWDA

RPPPAAPSFRQVSCLKELVARVLQRLCERGAKNVLAFGFALLDGARGGPPEAFTTSVRSYLPNT

VTDALRGSGAWGLLLRRVGDDVLVHLLARCALFVLVAPSCAYQVCGPPLYQLGAATQARPPPH

ASGPRRRLGCERAWNHSVREAGVPLGLPAPGARRRGGSASRSLPLPKRPRRGAAPEPERTPV

GQGSWAHPGRTRGPSDRGFCVVSPARPAEEATSLEGALSGTRHSHPSVGRQHHAGPPSTSRP

PRPWDTPCPPVYAETKHFLYSSGDKEQLRPSFLLSSLRPSLTGARRLVETIFLGSRPWMPGTPR

RLPRLPQRYWQMRPLFLELLGNHAQCPYGVLLKTHCPLRAAVTPAAGVCAREKPQGSVAAPEE

EDTDPRRLVQLLRQHSSPWQVYGFVRACLRRLVPPGLWGSRHNERRFLRNTKKFISLGKHAKL

SLQELTWKMSVRDCAWLRRSPGVGCVPAAEHRLREEILAKFLHWLMSVYVVELLRSFFYVTETT

FQKNRLFFYRKSVWSKLQSIGIRQHLKRVQLRELSEAEVRQHREARPALLTSRLRFIPKPDGLRPI

VNMDYVVGARTFRREKRAERLTSRVKALFSVLNYERARRPGLLGASVLGLDDIHRAWRTFVLRV

RAQDPPPELYFVKVDVTGAYDTIPQDRLTEVIASIIKPQNTYCVRRYAVVQKAAHGHVRKAFKSH

VSTLTDLQPYMRQFVAHLQETSPLRDAVVIEQSSSLNEASSGLFDVFLRFMCHHAVRIRGKSYVQ

CQGIPQGSILSTLLCSLCYGDMENKLFAGIRRDGLLLRLVDDFLLVTPHLTHAKTFLSYARTSIRAS

-continued
LTFNRGFKAGRNMRRKLFGVLRLKCHSLFLDLQVNSLQTVCTNIYKILLLQAYRFHACVLQLPFH

QQVWKNPTFFLRVISDTASLCYSILKAKNAGMSLGAKGAAGPLPSEAVQWLCHQAFLLKLTRHR

VTYVPLLGSLRTAQTQLSRKLPGTTLTALEAAANPALPSDFKTILD

SEQ ID NO: 4 Kozak sequence
GCCACCATG

SEQ ID NO: 5 bovine growth hormone PolyA signal
CTGTGCCTTCTAGTTGCCAGCCATCTGTTGTTTGCCCCTCCCCCGTGCCTTCCTTGACCCTG

GAAGGTGCCACTCCCACTGTCCTTTCCTAATAAAATGAGGAAATTGCATCGCATTGTCTGAG

TAGGTGTCATTCTATTCTGGGGGGTGGGGTGGGGCAGGACAGCAAGGGGGAGGATTGGGA

AGACAATAGCAGGCATGCTGGGGATGCGGTGGGCTCTATGG

SEQ ID NO: 6 AAV2 5' ITR sequence
CCTGCAGGCAGCTGCGCGCTCGCTCGCTCACTGAGGCCGCCCGGGCGTCGGGCGACCTTT

GGTCGCCCGGCCTCAGTGAGCGAGCGAGCGCGCAGAGAGGGAGTGGCCAACTCCATCACT

AGGGGTTCCT

SEQ ID NO: 7 AAV2 3' ITR sequence
AGGAACCCCTAGTGATGGAGTTGGCCACTCCCTCTCTGCGCGCTCGCTCGCTCACTGAGGC

CGGGCGACCAAAGGTCGCCCGACGCCCGGGCTTTGCCCGGGGGGCCTCAGTGAGCGAGC

GAGCGCGCAGCTGCCTGCAGG

SEQ ID NO: 8 wild type human long isoform TERT nucleic acid
sequence (hTERT WT)
ATGCCGCGCGCTCCCCGCTGCCGAGCCGTGCGCTCCCTGCTGCGCAGCCACTACCGCGAG

GTGCTGCCGCTGGCCACGTTCGTGCGGCGCGCCTGGGGCCCCAGGGCTGGCGGCTGGTGCA

GCGCGGGGACCCGGCGGCTTTCCGCGCGCTGGTGGCCCAGTGCCTGGTGTGCGTGCCCT

GGGACGCACGGCCGCCCCCCGCCGCCCCCTCCTTCCGCCAGGTGTCCTGCCTGAAGGAGC

TGGTGGCCCGAGTGCTGCAGAGGCTGTGCGAGCGCGGCGCGAAGAACGTGCTGGCCTTCG

GCTTCGCGCTGCTGGACGGGGCCCGCGGGGGGCCCCCCCGAGGCCTTCACCACCAGCGTG

CGCAGCTACCTGCCCAACACGGTGACCGACGCACTGCGGGGGAGCGGGGCGTGGGGGCT

GCTGCTGCGCCGCGTGGGCGACGACGTGCTGGTTCACCTGCTGGCACGCTGCGCGCTCTT

TGTGCTGGTGGCTCCCAGCTGCGCCTACCAGGTGTGCGGGCCGCCGCTGTACCAGCTCGG

CGCTGCCACTCAGGCCCGGCCCCCGCCACACGCTAGTGGACCCCGAAGGCGTCTGGGATG

CGAACGGGCCTGGAACCATAGCGTCAGGGAGGCCGGGGTCCCCCTGGGCCTGCCAGCCC

CGGGTGCGAGGAGGCGCGGGGGCAGTGCCAGCCGAAGTCTGCCGTTGCCCAAGAGGCCC

AGGCGTGGCGCTGCCCCTGAGCCGGAGCGGACGCCCGTTGGGCAGGGGTCCTGGGCCCA

CCCGGGCAGGACGCGTGGACCGAGTGACCGTGGTTTCTGTGTGGTGTCACCTGCCAGACC

CGCCGAAGAAGCCACCTCTTTGGAGGGTGCGCTCTCTGGCACGCGCCACTCCCACCCATCC

GTGGGCCGCCAGCACCACGCGGGCCCCCCATCCACATCGCGGCCACCACGTCCCTGGGAC

ACGCCTTGTCCCCCGGTGTACGCCGAGACCAAGCACTTCCTCTACTCCTCAGGCGACAAGG

AGCAGCTGCGGCCCTCCTTCCTACTCAGCTCTCTGAGGCCCAGCCTGACTGGCGCTCGGAG

GCTCGTGGAGACCATCTTTCTGGGTTCCAGGCCCTGGATGCCAGGGACTCCCCGCAGGTTG

CCCCGCCTGCCCCAGCGCTACTGGCAAATGCGGCCCCTGTTTCTGGAGCTGCTTGGGAACC

ACGCGCAGTGCCCCTACGGGGTGCTCCTCAAGACGCACTGCCCGCTGCGAGCTGCGGTCA

CCCCAGCAGCCGGTGTCTGTGCCCGGGAGAAGCCCCAGGGCTCTGTGGCGGCCCCCGAG

GAGGAGGACACAGACCCCCGTCGCCTGGTGCAGCTGCTCCGCCAGCACAGCAGCCCCTGG

CAGGTGTACGGCTTCGTGCGGGCCTGCCTGCGCCGGCTGGTGCCCCCAGGCCTCTGGGG

-continued

CTCCAGGCACAACGAACGCCGCTTCCTCAGGAACACCAAGAAGTTCATCTCCCTGGGGAAG

CATGCCAAGCTCTCGCTGCAGGAGCTGACGTGGAAGATGAGCGTGCGGGACTGCGCTTGG

CTGCGCAGGAGCCCAGGGGTTGGCTGTGTTCCGGCCGCAGAGCACCGTCTGCGTGAGGAG

ATCCTGGCCAAGTTCCTGCACTGGCTGATGAGTGTGTACGTCGTCGAGCTGCTCAGGTCTTT

CTTTTATGTCACGGAGACCACGTTTCAAAAGAACAGGCTCTTTTTCTACCGGAAGAGTGTCT

GGAGCAAGTTGCAAAGCATTGGAATCAGACAGCACTTGAAGAGGGTGCAGCTGCGGGAGCT

GTCGGAAGCAGAGGTCAGGCAGCATCGGGAAGCCAGGCCCGCCCTGCTGACGTCCAGACT

CCGCTTCATCCCCAAGCCTGACGGGCTGCGGCCGATTGTGAACATGGACTACGTCGTGGGA

GCCAGAACGTTCCGCAGAGAAAGAGGGCCGAGCGTCTCACCTCGAGGGTGAAGGCACTG

TTCAGCGTGCTCAACTACGAGCGGGCGCGGCGCCCCGGCCTCCTGGGCGCCTCTGTGCTG

GGCCTGGACGATATCCACAGGGCCTGGCGCACCTTCGTGCTGCGTGTGCGGGCCCAGGAC

CCGCCGCCTGAGCTGTACTTTGTCAAGGTGGATGTGACGGGCGCGTACGACACCATCCCCC

AGGACAGGCTCACGGAGGTCATCGCCAGCATCATCAAACCCCAGAACACGTACTGCGTGCG

TCGGTATGCCGTGGTCCAGAAGGCCGCCCATGGGCACGTCCGCAAGGCCTTCAAGAGCCA

CGTCTCTACCTTGACAGACCTCCAGCCGTACATGCGACAGTTCGTGGCTCACCTGCAGGAG

ACCAGCCCGCTGAGGGATGCCGTCGTCATCGAGCAGAGCTCCTCCCTGAATGAGGCCAGC

AGTGGCCTCTTCGACGTCTTCCTACGCTTCATGTGCCACCACGCCGTGCGCATCAGGGGCA

AGTCCTACGTCCAGTGCCAGGGGATCCCGCAGGGCTCCATCCTCTCCACGCTGCTCTGCAG

CCTGTGCTACGGCGACATGGAGAACAAGCTGTTTGCGGGGATTCGGCGGGACGGGCTGCT

CCTGCGTTTGGTGGATGATTTCTTGTTGGTGACACCTCACCTCACCCACGCGAAAACCTTCC

TCAGGACCCTGGTCCGAGGTGTCCCTGAGTATGGCTGCGTGGTGAACTTGCGGAAGACAGT

GGTGAACTTCCCTGTAGAAGACGAGGCCCTGGGTGGCACGGCTTTTGTTCAGATGCCGGCC

CACGGCCTATTCCCCTGGTGCGGCCTGCTGCTGGATACCCGGACCCTGGAGGTGCAGAGC

GACTACTCCAGCTATGCCCGGACCTCCATCAGAGCCAGTCTCACCTTCAACCGCGGCTTCA

AGGCTGGGAGGAACATGCGTCGCAAACTCTTTGGGGTCTTGCGGCTGAAGTGTCACAGCCT

GTTTCTGGATTTGCAGGTGAACAGCCTCCAGACGGTGTGCACCAACATCTACAAGATCCTCC

TGCTGCAGGCGTACAGGTTTCACGCATGTGTGCTGCAGCTCCCATTTCATCAGCAAGTTTGG

AAGAACCCCACATTTTTCCTGCGCGTCATCTCTGACACGGCCTCCCTCTGCTACTCCATCCT

GAAAGCCAAGAACGCAGGGATGTCGCTGGGGGGCCAAGGGCGCCGCCGGCCCTCTGCCCT

CCGAGGCCGTGCAGTGGCTGTGCCACCAAGCATTCCTGCTCAAGCTGACTCGACACCGTGT

CACCTACGTGCCACTCCTGGGGTCACTCAGGACAGCCCAGACGCAGCTGAGTCGGAAGCT

CCCGGGGACGACGCTGACTGCCCTGGAGGCCGCAGCCAACCCGGCACTGCCCTCAGACTT

CAAGACCATCCTGGACTGA

SEQ ID NO: 9 human short isoform TERT nucleic acid sequence
ATGCCGCGCGCTCCCCGCTGCCGAGCCGTGCGCTCCCTGCTGCGCAGCCACTACCGC

GAGGTGCTGCCGCTGGCCACGTTCGTGCGGCGCCTGGGGCCCCAGGGCTGGCGGCT

GGTGCAGCGCGGGGACCCGGCGGCTTTCCGCGCGCTGGTGGCCCAGTGCCTGGTGT

GCGTGCCCTGGGACGCACGGCCGCCCCCCGCCGCCCCCTCCTTCCGCCAGGTGTCCT

GCCTGAAGGAGCTGGTGGCCCGAGTGCTGCAGAGGCTGTGCGAGCGCGGCGCGAAGA

ACGTGCTGGCCTTCGGCTTCGCGCTGCTGGACGGGGCCCGCGGGGGGCCCCCCGAG

GCCTTCACCACCAGCGTGCGCAGCTACCTGCCCAACACGGTGACCGACGCACTGCGG

-continued

```
GGGAGCGGGGCGTGGGGGCTGCTGCTGCGCCGCGTGGGCGACGACGTGCTGGTTCA

CCTGCTGGCACGCTGCGCGCTCTTTGTGCTGGTGGCTCCCAGCTGCGCCTACCAGGTG

TGCGGGCCGCCGCTGTACCAGCTCGGCGCTGCCACTCAGGCCCGGCCCCCGCCACAC

GCTAGTGGACCCCGAAGGCGTCTGGGATGCGAACGGGCCTGGAACCATAGCGTCAGG

GAGGCCGGGGTCCCCCTGGGCCTGCCAGCCCCGGGTGCGAGGAGGCGCGGGGGCAG

TGCCAGCCGAAGTCTGCCGTTGCCCAAGAGGCCCAGGCGTGGCGCTGCCCCTGAGCC

GGAGCGGACGCCCGTTGGGCAGGGGTCCTGGGCCCACCCGGGCAGGACGCGTGGAC

CGAGTGACCGTGGTTTCTGTGTGGTGTCACCTGCCAGACCCGCCGAAGAAGCCACCTC

TTTGGAGGGTGCGCTCTCTGGCACGCGCCACTCCCACCCATCCGTGGGCCGCCAGCA

CCACGCGGGCCCCCCATCCACATCGCGGCCACCACGTCCCTGGGACACGCCTTGTCC

CCCGGTGTACGCCGAGACCAAGCACTTCCTCTACTCCTCAGGCGACAAGGAGCAGCTG

CGGCCCTCCTTCCTACTCAGCTCTCTGAGGCCCAGCCTGACTGGCGCTCGGAGGCTCG

TGGAGACCATCTTTCTGGGTTCCAGGCCCTGGATGCCAGGGACTCCCCGCAGGTTGCC

CCGCCTGCCCCAGCGCTACTGGCAAATGCGGCCCCTGTTTCTGGAGCTGCTTGGGAAC

CACGCGCAGTGCCCCTACGGGGTGCTCCTCAAGACGCACTGCCCGCTGCGAGCTGCG

GTCACCCCAGCAGCCGGTGTCTGTGCCCGGGAGAAGCCCCAGGGCTCTGTGGCGGCC

CCCGAGGAGGAGGACACAGACCCCCGTCGCCTGGTGCAGCTGCTCCGCCAGCACAGC

AGCCCCTGGCAGGTGTACGGCTTCGTGCGGGCCTGCCTGCGCCGGCTGGTGCCCCCA

GGCCTCTGGGGCTCCAGGCACAACGAACGCCGCTTCCTCAGGAACACCAAGAAGTTCA

TCTCCCTGGGGAAGCATGCCAAGCTCTCGCTGCAGGAGCTGACGTGGAAGATGAGCGT

GCGGGACTGCGCTTGGCTGCGCAGGAGCCCAGGGGTTGGCTGTGTTCCGGCCGCAGA

GCACCGTCTGCGTGAGGAGATCCTGGCCAAGTTCCTGCACTGGCTGATGAGTGTGTAC

GTCGTCGAGCTGCTCAGGTCTTTCTTTTATGTCACGGAGACCACGTTTCAAAAGAACAG

GCTCTTTTTCTACCGGAAGAGTGTCTGGAGCAAGTTGCAAAGCATTGGAATCAGACAGC

ACTTGAAGAGGGTGCAGCTGCGGGAGCTGTCGGAAGCAGAGGTCAGGCAGCATCGGG

AAGCCAGGCCCGCCCTGCTGACGTCCAGACTCCGCTTCATCCCCAAGCCTGACGGGCT

GCGGCCGATTGTGAACATGGACTACGTCGTGGGAGCCAGAACGTTCCGCAGAGAAAAG

AGGGCCGAGCGTCTCACCTCGAGGGTGAAGGCACTGTTCAGCGTGCTCAACTACGAGC

GGGCGCGGCGCCCCGGCCTCCTGGGCGCCTCTGTGCTGGGCCTGGACGATATCCACA

GGGCCTGGCGCACCTTCGTGCTGCGTGTGCGGGCCCAGGACCCGCCGCCTGAGCTGT

ACTTTGTCAAGGTGGATGTGACGGGCGCGTACGACACCATCCCCCAGGACAGGCTCAC

GGAGGTCATCGCCAGCATCATCAAACCCCAGAACACGTACTGCGTGCGTCGGTATGCC

GTGGTCCAGAAGGCCGCCCATGGGCACGTCCGCAAGGCCTTCAAGAGCCACGTCTCTA

CCTTGACAGACCTCCAGCCGTACATGCGACAGTTCGTGGCTCACCTGCAGGAGACCAG

CCCGCTGAGGGATGCCGTCGTCATCGAGCAGAGCTCCTCCCTGAATGAGGCCAGCAGT

GGCCTCTTCGACGTCTTCCTACGCTTCATGTGCCACCACGCCGTGCGCATCAGGGGCA

AGTCCTACGTCCAGTGCCAGGGGATCCCGCAGGGCTCCATCCTCTCCACGCTGCTCTG

CAGCCTGTGCTACGGCGACATGGAGAACAAGCTGTTTGCGGGGATTCGGCGGGACGG

GCTGCTCCTGCGTTTGGTGGATGATTTCTTGTTGGTGACACCTCACCTCACCCACGCGA

AAACCTTCCTCAGCTATGCCCGGACCTCCATCAGAGCCAGTCTCACCTTCAACCGCGGC
```

-continued

```
TTCAAGGCTGGGAGGAACATGCGTCGCAAACTCTTTGGGGTCTTGCGGCTGAAGTGTC

ACAGCCTGTTTCTGGATTTGCAGGTGAACAGCCTCCAGACGGTGTGCACCAACATCTAC

AAGATCCTCCTGCTGCAGGCGTACAGGTTTCACGCATGTGTGCTGCAGCTCCCATTTCA

TCAGCAAGTTTGGAAGAACCCCACATTTTTCCTGCGCGTCATCTCTGACACGGCCTCCC

TCTGCTACTCCATCCTGAAAGCCAAGAACGCAGGGATGTCGCTGGGGGCCAAGGGCGC

CGCCGGCCCTCTGCCCTCCGAGGCCGTGCAGTGGCTGTGCCACCAAGCATTCCTGCTC

AAGCTGACTCGACACCGTGTCACCTACGTGCCACTCCTGGGGTCACTCAGGACAGCCC

AGACGCAGCTGAGTCGGAAGCTCCCGGGGACGACGCTGACTGCCCTGGAGGCCGCAG

CCAACCCGGCACTGCCCTCAGACTTCAAGACCATCCTGGACTGA

SEQ ID NO: 10 recombinant nucleic acid of a) (AAV2 5' ITR +
SpB promoter + Kozak + hTERT(-ID) + AAV2 3' ITR)
CCTGCAGGCAGCTGCGCGCTCGCTCGCTCACTGAGGCCGCCCGGGCGTCGGGCGACC

TTTGGTCGCCCGGCCTCAGTGAGCGAGCGAGCGCGCAGAGAGGGAGTGGCCAACTCC

ATCACTAGGGGTTCCTGCGGCCGCGATATCATAGGGCTGTCTGGGAGCCACTCCAGGG

CCACAGAAATCTTGTCTCTGACTCAGGGTATTTTGTTTTCTGTTTTGTGTAAATGCTCTTC

TGACTAATGCAAACCATGTGTCCATAGAACCAGAAGATTTTTCCAGGGGAAAAGGTAAG

GAGGTGGTGAGAGTGTCCTGGGTCTGCCCTTCCAGGGCTTGCCCTGGGTTAAGAGCCA

GGCAGGAAGCTCTCAAGAGCATTGCTCAAGAGTAGAGGGGGCCTGGGAGGCCCAGGG

AGGGGATGGGAGGGGAACACCCAGGCTGCCCCCAACCAGATGCCCTCCACCCTCCTC

AACCTCCCTCCCACGGCCTGGAGAGGTGGGACCAGGTATGGAGGCTTGAGAGCCCCT

GGTTGGAGGAAGCCACAAGTCCAGGAACATGGGAGTCTGGGCAGGGGGCAAAGGAGG

CAGGAACAGGCCATCAGCCAGGACAGGTGGTAAGGCAGGCAGGAGTGTTCCTGCTGG

GAAAAGGTGGGATCAAGCACCTGGAGGGCTCTTCAGAGCAAAGACAAACACTGAGGTC

GCTGCCACTCCTACAGAGCCCCCACGCCCCGCCCAGCTATAAGGGGCCATGCACCAAG

CAGGGTACCCAGGCTGCAGAGGTGCGAATTCATTTAAATTCTAGCTAGCACGCGTGCCA

CCATGCCACGAGCGCCCCGATGCAGGGCCGTGCGAAGTCTCCTGCGATCCCACTACAG

GGAAGTGCTGCCACTTGCAACGTTTGTCCGCAGGCTTGGGCCACAAGGGTGGCGCCTT

GTACAGAGAGGCGATCCCGCGGCGTTCAGGGCACTTGTTGCGCAATGTCTCGTGTGTG

TGCCCTGGGACGCACGGCCGCCCCCTGCTGCACCATCATTCAGGCAAGTCAGTTGTTT

GAAAGAATTGGTCGCCCGCGTATTGCAGAGACTTTGTGAGAGGGGGGCAAAGAATGTC

TTGGCGTTCGGATTTGCGCTTCTGGACGGAGCTAGGGGTGGACCACCTGAGGCATTCA

CCACCTCAGTGAGATCCTACCTGCCCAATACGGTTACCGATGCTCTCCGCGGGTCTGGT

GCTTGGGGGTTGCTCCTTCGAAGAGTGGGTGATGATGTGCTCGTTCACCTGTTGGCGA

GGTGCGCGTTGTTCGTCCTTGTGGCACCAAGCTGTGCGTATCAAGTTTGTGGACCGCC

GCTCTACCAGCTTGGCGCAGCTACACAAGCGCGACCTCCCCCACACGCATCTGGTCCC

AGACGGCGCCTCGGATGCGAGCGAGCGTGGAATCACAGCGTGCGCGAAGCGGGCGTG

CCTCTTGGCCTCCCCGCGCCAGGTGCGAGGAGGAGAGGTGGTTCCGCGTCTCGGAGC

CTTCCGCTGCCGAAGAGACCCCGACGAGGAGCTGCGCCTGAACCAGAGAGGACCCCC

GTTGGACAAGGCTCCTGGGCACACCCGGGCCGAACCAGGGGCCCGAGCGACAGGGGT

TTTTGCGTGGTAAGTCCAGCTCGGCCCGCAGAGGAAGCGACGTCCCTTGAAGGCGCAC

TTTCCGGTACTAGACATAGCCACCCCTCAGTCGGAAGGCAGCACCACGCGGGACCACC

GTCTACGAGCCGGCCACCTCGGCCGTGGGACACACCTTGTCCTCCTGTTTATGCAGAG
```

ACCAAACATTTCTTGTATAGCAGCGGGGACAAGGAACAGCTTAGGCCCTCCTTCTTGCT

GTCAAGCCTGCGCCCGTCTCTGACTGGTGCACGCCGGCTGGTCGAGACCATCTTCCTC

GGGTCTAGGCCGTGGATGCCTGGTACACCTAGGAGATTGCCTCGCCTCCCCCAACGAT

ACTGGCAAATGAGACCGTTGTTTCTCGAATTGCTCGGCAATCATGCGCAGTGCCCCTAC

GGGGTCTTGCTTAAGACTCATTGCCCTTTGAGAGCTGCTGTGACGCCTGCCGCCGGAG

TGTGTGCCAGAGAAAAACCCCAGGGCAGTGTCGCCGCCCCGGAGGAGGAAGACACGG

ACCCTAGGCGGTTGGTACAACTCCTTCGACAGCACTCATCTCCGTGGCAAGTTTACGGT

TTCGTACGGGCTTGCCTTAGGAGACTCGTGCCGCCGGGTCTCTGGGGTTCAAGGCATA

ACGAAAGGAGGTTCCTGCGGAATACGAAGAAATTTATTTCATTGGGGAAACATGCGAAG

CTTTCCTTGCAAGAACTTACATGGAAGATGAGCGTCAGGGACTGCGCGTGGTTGAGGA

GGTCACCGGGGGTGGGTTGCGTCCCCGCCGCAGAGCACCGCCTTCGCGAAGAGATTC

TCGCCAAATTTCTCCATTGGCTGATGTCTGTTTATGTAGTAGAATTGTTGCGCTCATTTTT

CTATGTTACCGAGACTACTTTCCAAAAGAACAGATTGTTCTTCTACCGGAAATCTGTTTG

GTCAAAACTTCAATCCATAGGCATTAGACAGCATCTGAAAAGGGTTCAATTGAGGGAACT

CAGTGAGGCCGAGGTTAGACAGCATCGGGAGGCAAGGCCCGCTTTGCTTACGTCAAGA

CTTCGGTTTATACCCAAGCCGGATGGATTGCGGCCGATTGTAAACATGGACTATGTTGT

AGGCGCTCGGACGTTTCGCCGCGAGAAGCGCGCGGAACGACTGACGAGTAGGGTTAA

GGCGTTGTTCAGCGTGCTTAACTACGAACGCGCCAGGAGACCTGGGCTTTTGGGTGCA

TCAGTCTTGGGTCTTGATGATATACACCGGGCGTGGAGAACATTTGTTCTGCGAGTCCG

GGCCCAAGATCCCCCTCCCGAGTTGTACTTCGTGAAGGTAGATGTAACTGGCGCGTAC

GATACCATCCCCCAAGATAGACTTACGGAGGTTATTGCCTCCATCATTAAACCGCAAAAC

ACGTACTGCGTCCGAAGGTATGCAGTTGTCCAGAAGGCTGCACATGGACATGTACGAAA

AGCTTTCAAATCCCATGTAAGCACCTTGACCGACCTTCAACCATATATGAGGCAATTCGT

CGCGCACCTCCAGGAGACCTCCCCTCTCCGAGATGCCGTAGTGATCGAACAATCATCTA

GCCTGAATGAGGCATCCTCCGGTTTGTTTGACGTGTTTTTGCGCTTTATGTGTCACCAC

GCAGTTCGCATTCGCGGAAAGAGTTATGTTCAATGTCAAGGAATCCCCCAGGGAAGTAT

CCTTTCCACTCTCCTTTGTAGTTTGTGCTACGGCGACATGGAGAATAAGCTCTTTGCTGG

CATTCGGAGGGACGGCCTTTTGTTGAGGCTCGTCGACGATTTCCTCCTGGTGACACCAC

ATCTCACTCATGCCAAGACGTTCCTGCGGACGCTTGTCAGAGGGGTTCCTGAGTATGGA

TGCGTCGTCAACCTTAGAAAAACAGTCGTGAATTTCCCCGTGGAGGATGAAGCACTTGG

GGGCACGGCTTTCGTTCAAATGCCTGCCCACGGCCTGTTCCCGTGGTGTGGCCTCCTT

CTGGATACTCGGACCCTTGAGGTTCAGTCAGATTATTCAAGCTATGCCAGGACGTCCAT

TAGAGCTTCCCTGACCTTCAATCGAGGATTTAAAGCAGGGCGCAATATGCGGAGGAAGC

TGTTCGGTGTTCTTAGGTTGAAGTGTCATTCACTCTTTCTTGATCTTCAAGTTAACTCTCT

GCAGACAGTCTGTACGAACATCTACAAGATCTTGCTTTTGCAAGCTTACCGCTTCCACG

CTTGTGTTCTCCAACTGCCCTTTCATCAACAAGTGTGGAAAAACCCCACGTTTTTCCTGC

GAGTCATCTCAGACACGGCCAGCCTTTGCTATTCCATCCTCAAGGCTAAAAACGCGGGA

ATGTCTTTGGGCGCTAAGGGGGCCGCAGGTCCATTGCCATCCGAGGCCGTCCAGTGGT

TGTGTCACCAAGCTTTCTTGCTTAAATTGACTCGGCATCGCGTTACATACGTTCCCCTCC

TCGGCTCCTTGAGAACGGCGCAAACGCAGCTTAGCCGGAAGCTGCCAGGGACGACCCT

-continued

TACTGCCCTTGAAGCGGCAGCGAATCCGGCGTTGCCTAGCGATTTTAAGACTATTTTGG

ATTGAGTCGAGCATTTAAATACGTGGAGCTCGCTGATCAGCCTCGACTGTGCCTTCTAG

TTGCCAGCCATCTGTTGTTTGCCCCTCCCCCGTGCCTTCCTTGACCCTGGAAGGTGCCA

CTCCCACTGTCCTTTCCTAATAAAATGAGGAAATTGCATCGCATTGTCTGAGTAGGTGTC

ATTCTATTCTGGGGGGTGGGGTGGGGCAGGACAGCAAGGGGGAGGATTGGGAAGACA

ATAGCAGGCATGCTGGGGATGCGGTGGGCTCTATGGCCACGTGGATATCGCGGCCGC

AGGAACCCCTAGTGATGGAGTTGGCCACTCCCTCTCTGCGCGCTCGCTCGCTCACTGA

GGCCGGGCGACCAAAGGTCGCCCGACGCCCGGGCTTTGCCCGGGCGGCCTCAGTGA

GCGAGCGAGCGCGCAGCTGCCTGCAGG

SEQ ID NO: 11 codon optimized version of human long isoform
TERT nucleic acid sequence (hTERT-ID)
ATGCCACGAGCGCCCCGATGCAGGGCCGTGCGAAGTCTCCTGCGATCCCACTACAGG

GAAGTGCTGCCACTTGCAACGTTTGTCCGCAGGCTTGGGCCACAAGGGTGGCGCCTTG

TACAGAGAGGCGATCCCGCGGCGTTCAGGGCACTTGTTGCGCAATGTCTCGTGTGTGT

GCCCTGGGACGCACGGCCGCCCCCTGCTGCACCATCATTCAGGCAAGTCAGTTGTTTG

AAAGAATTGGTCGCCCGCGTATTGCAGAGACTTTGTGAGAGGGGGCAAAGAATGTCTT

GGCGTTCGGATTTGCGCTTCTGGACGGAGCTAGGGGGGACCACCTGAGGCATTCACC

ACCTCAGTGAGATCCTACCTGCCCAATACGGTTACCGATGCTCTCCGCGGGTCTGGTG

CTTGGGGGTTGCTCCTTCGAAGAGTGGGTGATGATGTGCTCGTTCACCTGTTGGCGAG

GTGCGCGTTGTTCGTCCTTGTGGCACCAAGCTGTGCGTATCAAGTTTGTGGACCGCCG

CTCTACCAGCTTGGCGCAGCTACACAAGCGCGACCTCCCCCACACGCATCTGGTCCCA

GACGGCGCCTCGGATGCGAGCGAGCGTGGAATCACAGCGTGCGCGAAGCGGGCGTG

CCTCTTGGCCTCCCCGCGCCAGGTGCGAGGAGGAGAGGTGGTTCCGCGTCTCGGAGC

CTTCCGCTGCCGAAGAGACCCCGACGAGGAGCTGCGCCTGAACCAGAGAGGACCCCC

GTTGGACAAGGCTCCTGGGCACACCCGGGCCGAACCAGGGGCCCGAGCGACAGGGGT

TTTTGCGTGGTAAGTCCAGCTCGGCCCGCAGAGGAAGCGACGTCCCTTGAAGGCGCAC

TTTCCGGTACTAGACATAGCCACCCCTCAGTCGGAAGGCAGCACCACGCGGGACCACC

GTCTACGAGCCGGCCACCTCGGCCGTGGGACACACCTTGTCCTCCTGTTTATGCAGAG

ACCAAACATTTCTTGTATAGCAGCGGGGACAAGGAACAGCTTAGGCCCTCCTTCTTGCT

GTCAAGCCTGCGCCCGTCTCTGACTGGTGCACGCCGGCTGGTCGAGACCATCTTCCTC

GGGTCTAGGCCGTGGATGCCTGGTACACCTAGGAGATTGCCTCGCCTCCCCCAACGAT

ACTGGCAAATGAGACCGTTGTTTCTCGAATTGCTCGGCAATCATGCGCAGTGCCCCTAC

GGGGTCTTGCTTAAGACTCATTGCCCTTTGAGAGCTGCTGTGACGCCTGCCGCCGGAG

TGTGTGCCAGAGAAAAACCCCAGGGCAGTGTCGCCGCCCCGGAGGAGGAAGACACGG

ACCCTAGGCGGTTGGTACAACTCCTTCGACAGCACTCATCTCCGTGGCAAGTTTACGGT

TTCGTACGGGCTTGCCTTAGGAGACTCGTGCCGCCGGGTCTCTGGGGTTCAAGGCATA

ACGAAAGGAGGTTCCTGCGGAATACGAAGAAATTTATTTCATTGGGGAAACATGCGAAG

CTTTCCTTGCAAGAACTTACATGGAAGATGAGCGTCAGGGACTGCGCGTGGTTGAGGA

GGTCACCGGGGGTGGGTTGCGTCCCCGCCGCAGAGCACCGCCTTCGCGAAGAGATTC

TCGCCAAATTTCTCCATTGGCTGATGTCTGTTTATGTAGTAGAATTGTTGCGCTCATTTTT

CTATGTTACCGAGACTACTTTCCAAAAGAACAGATTGTTCTTCTACCGGAAATCTGTTTG

GTCAAAACTTCAATCCATAGGCATTAGACAGCATCTGAAAAGGGGTTCAATTGAGGGAACT

-continued

CAGTGAGGCCGAGGTTAGACAGCATCGGGAGGCAAGGCCCGCTTTGCTTACGTCAAGA

CTTCGGTTTATACCCAAGCCGGATGGATTGCGGCCGATTGTAAACATGGACTATGTTGT

AGGCGCTCGGACGTTTCGCCGCGAGAAGCGCGCGGAACGACTGACGAGTAGGGTTAA

GGCGTTGTTCAGCGTGCTTAACTACGAACGCGCCAGGAGACCTGGGCTTTTGGGTGCA

TCAGTCTTGGGTCTTGATGATATACACCGGGCGTGGAGAACATTTGTTCTGCGAGTCCG

GGCCCAAGATCCCCCTCCCGAGTTGTACTTCGTGAAGGTAGATGTAACTGGCGCGTAC

GATACCATCCCCCAAGATAGACTTACGGAGGTTATTGCCTCCATCATTAAACCGCAAAC

ACGTACTGCGTCCGAAGGTATGCAGTTGTCCAGAAGGCTGCACATGGACATGTACGAAA

AGCTTTCAAATCCCATGTAAGCACCTTGACCGACCTTCAACCATATATGAGGCAATTCGT

CGCGCACCTCCAGGAGACCTCCCCTCTCCGAGATGCCGTAGTGATCGAACAATCATCTA

GCCTGAATGAGGCATCCTCCGGTTTGTTTGACGTGTTTTTGCGCTTTATGTGTCACCAC

GCAGTTCGCATTCGCGGAAAGAGTTATGTTCAATGTCAAGGAATCCCCCAGGGAAGTAT

CCTTTCCACTCTCCTTTGTAGTTTGTGCTACGGCGACATGGAGAATAAGCTCTTTGCTGG

CATTCGGAGGGACGGCCTTTTGTTGAGGCTCGTCGACGATTTCCTCCTGGTGACACCAC

ATCTCACTCATGCCAAGACGTTCCTGCGGACGCTTGTCAGAGGGGTTCCTGAGTATGGA

TGCGTCGTCAACCTTAGAAAAACAGTCGTGAATTTCCCCGTGGAGGATGAAGCACTTGG

GGGCACGGCTTTCGTTCAAATGCCTGCCCACGGCCTGTTCCCGTGGTGTGGCCTCCTT

CTGGATACTCGGACCCTTGAGGTTCAGTCAGATTATTCAAGCTATGCCAGGACGTCCAT

TAGAGCTTCCCTGACCTTCAATCGAGGATTTAAAGCAGGGCGCAATATGCGGAGGAAGC

TGTTCGGTGTTCTTAGGTTGAAGTGTCATTCACTCTTTCTTGATCTTCAAGTTAACTCTCT

GCAGACAGTCTGTACGAACATCTACAAGATCTTGCTTTTGCAAGCTTACCGCTTCCACG

CTTGTGTTCTCCAACTGCCCTTTCATCAACAAGTGTGGAAAAACCCCACGTTTTTCCTGC

GAGTCATCTCAGACACGGCCAGCCTTTGCTATTCCATCCTCAAGGCTAAAAACGCGGGA

ATGTCTTTGGGCGCTAAGGGGGCCGCAGGTCCATTGCCATCCGAGGCCGTCCAGTGGT

TGTGTCACCAAGCTTTCTTGCTTAAATTGACTCGGCATCGCGTTACATACGTTCCCCTCC

TCGGCTCCTTGAGAACGGCGCAAACGCAGCTTAGCCGGAAGCTGCCAGGGACGACCCT

TACTGCCCTTGAAGCGGCAGCGAATCCGGCGTTGCCTAGCGATTTTAAGACTATTTTGG

ATTGA

SEQ ID NO: 12 codon optimized version of human long isoform
TERT nucleic acid  sequence (hTERT-GA)
ATGCCTAGGGCTCCTAGATGTAGAGCCGTCAGAAGCCTGCTGCGGAGCCACTATAGAGAG

GTGCTGCCTCTGGCCACCTTCGTGCGTAGACTTGGACCTCAAGGATGGCGGCTGGTGCAG

AGAGGCGATCCTGCTGCTTTTAGAGCCCTGGTGGCCCAGTGTCTCGTGTGCGTTCCATGG

GATGCTAGACCTCCACCAGCTGCTCCCAGCTTCAGACAGGTGTCCTGCCTGAAAGAACTG

GTGGCCAGGGTGCTGCAGAGACTGTGTGAAAGGGGCGCCAAGAACGTGCTGGCCTTTGGA

TTTGCTCTGCTGGATGGCGCTAGAGGCGGACCTCCTGAGGCCTTTACAACAAGCGTGCGG

AGCTACCTGCCTAACACCGTGACAGATGCCCTGAGAGGATCTGGCGCTTGGGGACTGCTG

CTGAGAAGAGTGGGAGATGACGTGCTGGTGCATCTGCTGGCCAGATGCGCTCTGTTTGTG

CTGGTGGCTCCTAGCTGCGCCTACCAAGTTTGTGGCCCTCCACTGTATCAGCTGGGCGCT

GCTACACAGGCTAGACCACCTCCACATGCCAGCGGACCTAGAAGAAGGCTGGGCTGCGAA

AGAGCCTGGAACCACTCTGTTAGAGAAGCCGGCGTGCCACTGGGATTGCCTGCACCAGGT

-continued

```
GCAAGAAGAAGAGGCGGCAGCGCCTCTAGATCTCTGCCTCTGCCTAAGAGGCCTAGAAGA

GGGGCTGCCCCTGAGCCTGAGAGAACACCTGTTGGCCAAGGCTCTTGGGCCCATCCTGGC

AGAACAAGAGGCCCTAGCGATAGAGGCTTCTGCGTGGTGTCTCCTGCCAGACCTGCCGAG

GAAGCCACATCTCTTGAAGGCGCCCTGAGCGGCACAAGACACTCTCACCCATCTGTGGGC

AGACAGCACCATGCCGGACCTCCAAGCACAAGCAGACCACCTAGACCTTGGGACACCCCT

TGTCCTCCAGTGTACGCCGAGACAAAGCACTTCCTGTACAGCAGCGGCGACAAAGAGCAG

CTGAGGCCTAGCTTCCTGCTGTCCTCTCTGAGGCCATCTCTGACCGGTGCTCGGAGACTG

GTGGAAACCATCTTCCTGGGCAGCAGACCTTGGATGCCCGGCACACCTAGAAGGCTGCCT

AGACTGCCACAGCGGTACTGGCAAATGAGGCCCCTGTTCCTGGAACTGCTGGGCAATCAC

GCTCAGTGCCCTTATGGCGTGCTGCTGAAAACCCACTGTCCTCTGAGAGCCGCCGTGACA

CCAGCAGCTGGCGTTTGTGCCAGAGAGAAGCCTCAAGGCTCTGTGGCCGCTCCTGAGGAA

GAGGACACAGATCCTAGACGACTGGTGCAGCTCCTGAGACAGCACAGCTCTCCATGGCAG

GTCTACGGATTTGTGCGGGCCTGTCTGAGAAGGCTCGTTCCTCCTGGACTGTGGGGCTCC

AGACACAACGAGCGGCGGTTTCTGCGGAACACCAAGAAGTTCATCAGCCTGGGAAAGCAC

GCCAAGCTGAGCCTGCAAGAGCTGACCTGGAAGATGAGCGTGCGGGATTGTGCATGGCTG

AGAAGGTCCCCAGGCGTGGGATGTGTTCCTGCCGCTGAACACAGACTGCGGGAAGAGATC

CTGGCCAAGTTCCTGCACTGGCTGATGTCCGTGTACGTGGTCGAACTGCTTCGGAGCTTC

TTCTACGTGACCGAGACAACCTTCCAGAAGAACCGGCTGTTCTTCTACCGGAAGTCCGTG

TGGTCCAAGCTGCAGAGCATCGGCATCCGGCAGCATCTGAAGAGAGTGCAGCTGAGAGAG

CTGAGCGAAGCCGAAGTGCGGCAGCACAGAGAAGCTAGACCAGCTCTGCTGACCAGCAGG

CTGAGATTCATCCCCAAGCCTGATGGCCTGCGGCCTATCGTGAACATGGACTATGTTGTG

GGCGCCAGAACCTTTCGGAGAGAGAAGAGAGCCGAGCGGCTGACCTCTAGAGTGAAGGCC

CTGTTCAGCGTGCTGAACTACGAGAGAGCCAGAAGGCCAGGACTGCTGGGAGCCTCTGTT

CTGGGACTCGACGACATCCACAGAGCTTGGCGGACCTTTGTGCTGAGAGTGCGAGCCCAA

GATCCTCCACCTGAGCTGTACTTCGTGAAGGTGGACGTGACCGGCGCCTACGACACAATC

CCTCAGGACAGACTGACCGAAGTGATCGCCAGCATCATCAAGCCCCAGAACACCTACTGT

GTGCGGAGATACGCCGTGGTGCAGAAAGCCGCTCATGGCCACGTGCGGAAGGCCTTTAAG

AGCCATGTGTCTACCCTGACCGACCTGCAGCCTTACATGAGACAGTTCGTGGCCCATCTG

CAAGAGACAAGCCCTCTGAGGGATGCCGTGGTCATCGAACAGAGCAGCAGCCTGAATGAG

GCCAGCTCCGGCCTGTTTGATGTGTTTCTCCGGTTCATGTGCCACCACGCCGTGCGGATT

AGAGGCAAGAGCTACGTGCAGTGCCAGGGCATTCCTCAGGGCAGCATCCTGAGCACACTG

CTGTGCAGCCTGTGCTACGGCGACATGGAAAACAAGCTGTTCGCCGGCATCAGACGCGAC

GGCCTGCTTCTGAGACTGGTCGACGATTTCCTGCTCGTGACCCCTCACCTGACACACGCC

AAGACCTTTCTGAGAACACTCGTGCGGGGCGTGCCAGAGTATGGCTGTGTGGTCAACCTG

AGAAAGACCGTGGTCAACTTCCCCGTCGAGGATGAAGCCCTTGGCGGCACAGCTTTCGTG

CAGATGCCTGCTCATGGACTGTTCCCTTGGTGCGGCCTGCTGCTGGATACCAGAACACTG

GAAGTGCAGAGCGACTACAGCAGCTACGCCCGGACATCTATCAGAGCCAGCCTGACCTTC

AACCGGGGCTTTAAGGCCGGCAGAAACATGCGGAGAAAGCTGTTTGGAGTGCTGCGGCTG

AAGTGCCACTCTTTGTTTCTGGACCTGCAAGTGAACAGCCTGCAGACCGTGTGCACCAAC

ATCTACAAGATTCTGCTGCTGCAAGCCTACCGGTTCCACGCCTGTGTTCTGCAGCTGCCC

TTTCACCAGCAAGTGTGGAAGAACCCTACATTCTTCCTGCGCGTGATCAGCGACACCGCC
```

-continued

AGCCTGTGTTACTCCATCCTGAAGGCCAAAAACGCCGGCATGAGCCTGGGAGCTAAAGGC

GCTGCTGGACCTCTGCCTTCTGAAGCAGTGCAGTGGCTGTGTCACCAGGCCTTTCTGCTG

AAGCTGACCCGGCACAGAGTGACATATGTGCCTCTGCTGGGCTCCCTGAGAACCGCTCAA

ACACAGCTGAGCAGAAAGCTGCCTGGCACCACACTGACAGCCCTGGAAGCTGCAGCAAAC

CCTGCTCTGCCCAGCGACTTCAAGACCATCCTGGATTGA

SEQ ID NO: 13 codon optimized version of human long isoform
TERT nucleic acid sequence (hTERT_GS).
ATGCCAAGAGCTCCTCGGTGCAGAGCCGTGCGCAGCCTGCTGAGATCCCACTACCGTGAG

GTGCTACCTCTGGCCACCTTTGTGCGCAGACTGGGACCTCAAGGCTGGCGGCTGGTACAG

AGAGGCGACCCTGCCGCCTTCAGAGCCTTAGTGGCCCAGTGCCTGGTTTGCGTGCCTTGG

GATGCCCGGCCGCCTCCCGCCGCTCCTAGCTTCCGGCAGGTGTCCTGCCTGAAAGAACTG

GTTGCTAGAGTGCTGCAAAGACTGTGCGAGCGTGGCGCCAAGAACGTGCTGGCCTTCGGA

TTTGCCCTGCTGGACGGCGCCAGAGGTGGACCACCCGAGGCCTTCACGACTAGTGTCCGT

AGTTACCTGCCAAACACCGTGACAGACGCCCTGAGAGGCTCTGGCGCCTGGGGCCTGCTG

CTTCGGAGAGTGGGCGACGATGTGCTCGTTCACCTGCTGGCGAGGTGTGCCCTGTTCGTG

CTGGTGGCCCCTTCTTGTGCTTACCAGGTGTGCGGCCCTCCTCTGTACCAGCTGGGCGCT

GCAACCCAGGCCAGACCCCCGCCCCACGCGAGCGGCCCTAGGCGCCGCCTAGGTTGTGAA

AGAGCATGGAACCACAGTGTGAGAGAAGCCGGAGTGCCTCTGGGGCTGCCCGCACCTGGC

GCCAGAAGACGGGGCGGCTCCGCTTCTAGATCTCTGCCTCTGCCCAAGAGACCTAGACGC

GGGGCTGCTCCTGAGCCTGAGAGAACTCCAGTGGGCCAGGGCTCTTGGGCCCACCCCGGC

CGGACCAGAGGCCCCTCTGACCGGGGCTTCTGCGTTGTGAGCCCCGCTAGACCAGCCGAG

GAGGCCACATCTCTGGAGGGCGCGCTAAGCGGAACCAGACACAGCCACCCCTCTGTGGGC

AGACAGCACCATGCCGGCCCTCCATCCACCAGCAGACCTCCCAGACCTTGGGACACCCCG

TGCCCCCCCGTGTACGCCGAAACCAAGCACTTCCTGTACAGCAGCGGCGATAAGGAACAG

CTGAGGCCATCCTTCCTGCTGAGCAGCCTGCGGCCCAGCCTGACCGGCGCCCGGAGACTC

GTTGAAACAATCTTCCTGGGATCTAGACCTTGGATGCCCGGGACGCCCAGACGGCTGCCC

CGGCTGCCCCAGAGATACTGGCAGATGCGGCCTCTGTTCCTGGAACTGCTGGGCAACCAC

GCCCAGTGTCCTTACGGCGTGCTGCTGAAAACCCACTGCCCTCTCAGAGCCGCCGTGACA

CCTGCCGCCGGCGTGTGCGCCCGGGAGAAACCTCAGGGCAGCGTGGCCGCCCCTGAGGAA

GAAGACACAGATCCTCGGAGACTCGTGCAGCTGCTGCGCCAGCATTCCAGCCCTTGGCAG

GTCTATGGCTTTGTGAGAGCTTGTCTGCGGAGGCTGGTGCCCCCTGGCCTGTGGGGAAGC

AGACACAACGAGCGGAGATTCCTGAGAAACACCAAGAAGTTCATCAGCCTGGGAAAACAC

GCCAAGCTGTCCCTGCAAGAGCTGACCTGGAAGATGTCAGTGCGGGACTGTGCTTGGCTG

AGGAGAAGCCCTGGCGTGGGATGTGTCCCTGCCGCCGAACACCGGCTGAGAGAAGAAATC

CTGGCGAAATTCCTGCACTGGCTGATGTCTGTGTACGTGGTCGAGCTGCTGAGATCTTTT

TTCTACGTGACCGAGACCACCTTTCAGAAAAACAGACTGTTTTTCTACCGGAAGAGCGTG

TGGAGCAAGCTGCAGTCTATCGGCATCAGACAGCACCTGAAGAGAGTGCAACTGAGAGAG

CTGAGCGAGGCCGAGGTGCGGCAGCACCGAGAGGCCAGACCCGCCCTGCTGACCAGCAGA

CTGCGGTTCATCCCTAAGCCCGACGGCTTGCGGCCAATCGTGAACATGGACTACGTGGTG

GGCGCTAGAACCTTTAGGAGAGAAAAGCGGGCCGAGAGACTGACGAGCCGGGTTAAGGCC

CTGTTCAGCGTCCTTAACTACGAGAGAGCCAGAAGACCCGGCCTGCTGGGAGCGAGCGTG

-continued

```
CTGGGTTTGGACGACATCCACAGAGCCTGGAGAACCTTCGTTCTGAGAGTGAGAGCCCAG

GATCCTCCCCCCGAGCTGTACTTCGTGAAGGTGGACGTGACCGGCGCTTACGACACAATC

CCTCAGGACAGACTGACCGAGGTGATCGCCTCTATCATCAAGCCTCAGAACACATATTGC

GTGCGGCGGTACGCCGTGGTGCAGAAGGCCGCCCACGGCCACGTGAGAAAAGCCTTTAAG

AGCCATGTGTCCACCCTCACTGATCTGCAACCCTACATGAGACAGTTCGTGGCCCATCTC

CAGGAGACAAGCCCACTGCGGGATGCCGTTGTCATCGAGCAGAGCTCCAGCCTTAATGAG

GCTTCCTCTGGCCTGTTCGACGTGTTCCTACGGTTCATGTGCCACCACGCCGTGAGAATC

AGAGGAAAGTCTTACGTGCAGTGCCAGGGCATCCCCCAGGGAAGCATCCTGAGCACACTG

CTGTGCAGCCTGTGTTACGGCGACATGGAAAACAAGCTGTTCGCCGGCATCAGACGGGAT

GGCCTGCTTCTGAGATTGGTGGACGACTTCCTGCTGGTGACACCTCACCTGACACACGCT

AAGACCTTCCTGAGAACACTGGTGAGAGGCGTGCCTGAGTACGGCTGTGTGGTGAACCTG

CGGAAGACCGTGGTGAATTTCCCTGTGGAAGACGAGGCCCTGGGCGGCACCGCCTTTGTG

CAGATGCCTGCGCATGGCCTGTTCCCCTGGTGCGGCCTGCTGCTGGACACCAGAACCCTG

GAAGTGCAAAGCGACTACAGCTCTTATGCCAGAACCTCCATTAGAGCCTCACTCACATTT

AACCGGGGCTTCAAGGCCGGCCGGAATATGAGAAGAAAGCTGTTCGGCGTGCTGAGATTA

AAGTGCCACAGCCTGTTCCTGGATCTGCAAGTCAACAGCCTGCAGACAGTGTGCACCAAC

ATTTACAAGATTCTGCTGCTGCAGGCTTATAGATTCCACGCCTGCGTGCTGCAGCTGCCC

TTCCACCAGCAGGTCTGGAAAAACCCCACCTTCTTCCTGAGAGTGATCAGCGATACCGCC

AGCCTGTGCTACAGCATCCTGAAGGCCAAAAACGCCGGAATGAGCCTGGGCGCTAAGGGC

GCAGCTGGTCCCCTGCCCAGCGAGGCCGTGCAGTGGCTGTGCCACCAGGCCTTCCTGCTT

AAACTGACCAGACATAGAGTGACCTACGTGCCACTCCTGGGAAGCCTCCGGACCGCCCAA

ACACAGCTCAGCCGGAAGCTGCCTGGCACCACACTGACAGCCCTGGAAGCCGCCGCTAAT

CCTGCCCTGCCTAGCGATTTCAAGACCATCCTGGACTGA
```

SEQ ID NO: 14 VP1 AAV6.2

```
   1 atggctgccg atggttatct tccagattgg ctcgaggaca acctctctga gggcattcgc 61 gagtggtggg acttgaaacc tggagccccg aaacccaaag ccaaccagca aaagcaggac 121 gacggccggg gtctggtgct tcctggctac aagtacctcg gacccttcaa cggactcgac 181 aaggggagc ccgtcaacgc ggcggatgca gcggccctcg agcacgacaa ggcctacgac 241 cagcagctca aagcgggtga caatccgtac ctgcggtata ccacgccga cgccgagttt 301 caggagcgtc tgcaagaaga tacgtctttt gggggcaacc tcgggcgagc agtcttccag 361 gccaagaaga gggttctcga acctcttggt ctggttgagg aaggtgctaa gacggctcct 421 ggaaagaaac gtccggtaga gcagtcgcca aagagccag actcctcctc gggcattggc 481 aagacaggcc agcagcccgc taaaaagaga ctcaattttg gtcagactgg cgactcagag 541 tcagtccccg acccacaacc tctcggagaa cctccagcaa ccccgctgc tgtgggacct 601 actacaatgg cttcaggcgg tggcgcacca atggcagaca taacgaagg cgccgacgga 661 gtgggtaatg cctcaggaaa ttggcattgc gattccacat ggctgggcga cagagtcatc 721 accaccagca cccgaacatg ggccttgccc acctataaca accacctcta caagcaaatc 781 tccagtgctt caacggggc cagcaacgac aaccactact cggctacag cacccctcgg 841 gggtatttg atttcaacag attccactgc catttctcac cacgtgactg gcagcgactc
```

-continued

```
 901 atcaacaaca attggggatt ccggcccaag agactcaact tcaagctctt caacatccaa 961 gtcaaggagg tcacgacgaa tgatggcgtc acgaccatcg ctaataacct taccagcacg 1021 gttcaagtct tctcggactc ggagtaccag ttgccgtacg tcctcggctc tgcgcaccag 1081 ggctgcctcc ctccgttccc ggcggacgtg ttcatgattc cgcagtacgg ctacctaacg 1141 ctcaacaatg gcagccaggc agtgggacgg tcatcctttt actgcctgga atatttccca 1201 tcgcagatgc tgagaacggg caataacttt accttcagct acaccttcga ggacgtgcct 1261 ttccacagca gctacgcgca cagccagagc ctggaccggc tgatgaatcc tctcatcgac 1321 cagtacctgt attacctgaa cagaactcag aatcagtccg gaagtgccca aaacaaggac 1381 ttgctgtttta gccgggggtc tccagctggc atgtctgttc agcccaaaaa ctggctacct 1441 ggaccctgtt accggcagca gcgcgtttct aaaacaaaaa cagacaacaa caacagcaac 1501 tttacctgga ctggtgcttc aaaatataac cttaatgggc gtgaatctat aatcaaccct 1561 ggcactgcta tggcctcaca caaagacgac aaagacaagt tctttcccat gagcggtgtc 1621 atgatttttg gaaaggagag cgccggagct tcaaacactg cattggacaa tgtcatgatc 1681 acagacgaag aggaaatcaa agccactaac cccgtggcca ccgaaagatt tgggactgtg 1741 gcagtcaatc tccagagcag cagcacagac cctgcgaccg gagatgtgca tgttatggga 1801 gccttacctg gaatggtgtg gcaagacaga gacgtatacc tgcagggtcc tatttgggcc 1861 aaaattcctc acacggatgg acactttcac ccgtctcctc tcatgggcgg ctttggactt 1921 aagcacccgc ctcctcagat cctcatcaaa aacacgcctg ttcctgcgaa tcctccggca 1981 gagtttttcgg ctacaaagtt tgcttcattc atcacccagt attccacagg acaagtgagc 2041 gtggagattg aatgggagct gcagaaagaa aacagcaaac gctggaatcc cgaagtgcag 2101 tatacatcta actatgcaaa atctgccaac gttgatttca ctgtggacaa caatggactt 2161 tatactgagc ctcgcccat tggcacccgt tacctcaccc gtccctg
```

SEQ ID NO: 15 CDS VP1, 129L variant highlighted in bold.
MAADGYLPDWLEDNLSEGIREWWDLKPGAPKPKANQQKQDDGRG

LVLPGYKYLGPFNGLDKGEPVNAADAAALEHDKAYDQQLKAGDNPYLRYNHADAEFQE

RLQEDTSFGGNLGRAVFQAKKRVLEPLGLVEEGAKTAPGKKRPVEQSPQEPDSSSGIG

KTGQQPAKKRLNFGQTGDSESVPDPQPLGEPPATPAAVGPTTMASGGGAPMADNNEGA

DGVGNASGNWHCDSTWLGDRVITTSTRTWALPTYNNHLYKQISSASTGASNDNHYFGY

STPWGYFDFNRFHCHFSPRDWQRLINNNWGFRPKRLNFKLFNIQVKEVTTNDGVTTIA

NNLTSTVQVFSDSEYQLPYVLGSAHQGCLPPFPADVFMIPQYGYLTLNNGSQAVGRSS

FYCLEYFPSQMLRTGNNFTFSYTFEDVPFHSSYAHSQSLDRLMNPLIDQYLYYLNRTQ

NQSGSAQNKDLLFSRGSPAGMSVQPKNWLPGPCYRQQRVSKTKTDNNNSNFTWTGASK

YNLNGRESIINPGTAMASHKDDKDKFFPMSGVMIFGKESAGASNTALDNVMITDEEEI

KATNPVATERFGTVAVNLQSSSTDPATGDVHVMGALPGMVWQDRDVYLQGPIWAKIPH

TDGHFHPSPLMGGFGLKHPPPQILIKNTPVPANPPAEFSATKFASFITQYSTGQVSVE

IEWELQKENSKRWNPEVQYTSNYAKSANVDFTVDNNGLYTEPRPIGTRYLTRPL

The following examples must be considered as merely illustrative and in no case limiting of the scope of the present invention.

EXAMPLES

Example 1: Testing Different TERT Sequences and Choice of the Best Candidate AAV6.2-SpB-hTERT (Also Called AAV-TERT-01) Design SpB Promoter The regulatory sequences used to confer high lung expression relative to non-target tissues in the AAV vectors were obtained from the promoter of the human surfactant protein B (SpB) (*Homo sapiens* surfactant protein B (SFTPB), RefSeqGene on chromosome 2. Sequence ID: NG_016967.1). Due to the long size of the TERT sequence and the restricted cloning capacity of the AAV vectors, a shortened version of SpB was generated based on the minimal specific cis-regulatory elements of the human SpB gene. The SpB promoter sequence included the vertebrate consensus TATA-Box sequence for strong initiation (GC-TATAAGGGGCCATGC (SEQ ID NO: 16)). The DNA was cloned into the pAAV-CMV-MCS plasmid that contains AAV2 ITRs obtained from Cell Biolabs, Inc (Cat n°: VPK-410). The Kozak sequence, GCCACCATG (SEQ ID NO: 4), was included in AAV-SpB-TERT vectors at the start of the coding sequence to optimize its translation. The polyadenylation (Poly-A) signal included in the AAV-SpB-TERT vector was the bovine growth hormone polyadenylation signal.

Human Telomerase

There are two isoforms of the human TERT protein in the consensus CDS protein set database CCDS (ncbi.nlm.nih-.gov/projects/CCDS). The short isoform (3210 bp) corresponds to the *Homo sapiens* telomerase reverse transcriptase (TERT), transcript variant 2 (CCDS ID: CCDS54831.1, NM_001193376.3, NP_001180305.1). The long isoform (3399 bp) corresponds to the *Homo sapiens* telomerase reverse transcriptase (TERT), transcript variant 1, (CCDS ID: CCDS3861.2, NM_198253.3, NP_937983.2). Both sequences were cloned and evaluated for telomerase activity. Both short and long TERT variants could be expressed in human foreskin BJ fibroblasts by retroviral transduction.

Figure 1:
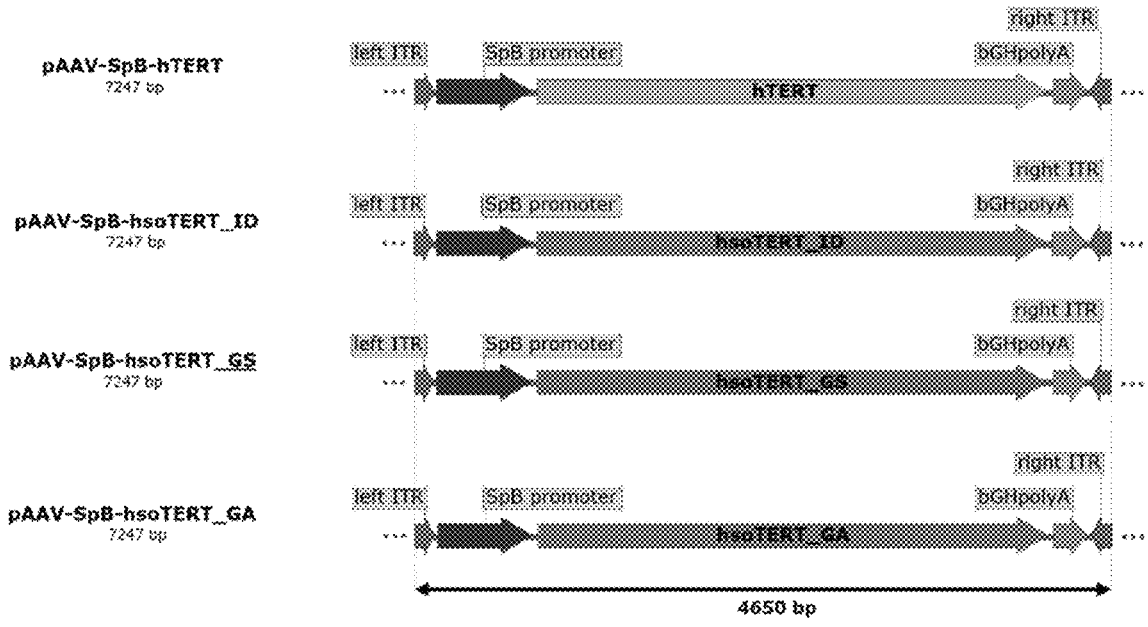
FIG. 1. The four different TERT codon-optimized sequences cloned into the AAV vector. The 4650 bp AAV vector genome comprises the SpB promoter, the corresponding TERT CDS, and the bGH PolyA signal all flanked by the AAV2 ITRs.

Optimization of codon usage to a specific species is broadly used to increase protein production from a transgene. To improve gene expression and increase the translational efficiency of the human TERT transgene, the transcript variant 1 CCDS (3399 nt) was selected to generate three different optimized sequences (GeneArt (GA): thermofisher.com/es/es/home/life-science/cloning/gene-synthesis/geneart-gene-synthesis/geneoptimizer.html; Integrated DNA Technologies (IDT): eu.idtdna.com/CodonOpt; and GeneScript (GS): genscript.com/gensmart-free-gene-codon-optimization.html). Finally, all the sequences incorporate specific restriction sites on 3' and 5' to clone into the final AAV vector (FIG. 1) and were synthesized by Thermo Fisher Scientific (Thermo Fisher: thermofisher.com/es/es/home/life-science/cloning/gene-synthesis/geneart-gene-synthesis.html).

Figures 2A, 2B:
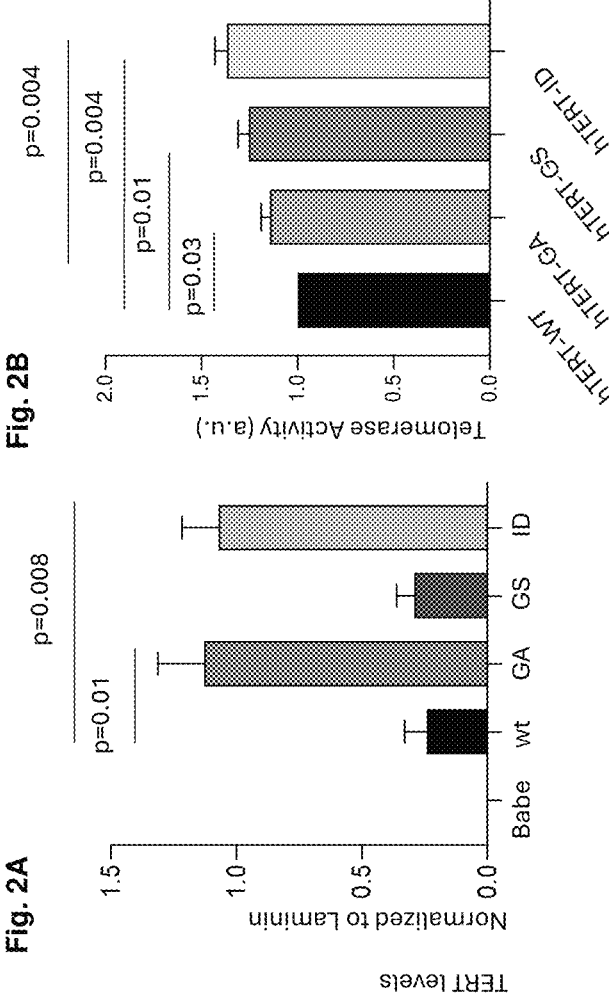
FIGS. 2A-2B. Telomerase protein levels were analyzed by Western blot and quantified by normalization to Laminin (FIG. 2A). Telomerase activity was analyzed by TRAP (FIG. 2B) as per Blasco et al., 1997 (Blasco M A, Lee H W, Hande M P, Samper E, Lansdorp P M, DePinho R A, Greider C W. Telomere shortening and tumor formation by mouse cells lacking telomerase RNA. Cell. 1997 Oct. 3; 91(1):25-34. doi: 10.1016/s0092-8674 (01) 80006-4. PMID: 9335332).

The three-codon optimized human Telomerase genes (GA, GS, and ID) and the wildtype TERT (v1) were cloned into the pBabe retroviral vector and introduced into BJ human fibroblasts that lack telomerase expression. The four hTERT versions were transcriptionally expressed in BJ fibroblast to high levels. Quantitative comparisons among them are not possible to perform as the sequence of the primer pairs used to analyze their expression are different for the four genes given their distinct TERT gene sequences. TERT protein levels were measured by western blot and hTERT-GA and hTERT-ID showed significantly higher levels as compared to hTERT-v1 and hTERT-GS. Telomerase activity measured by TRAP (telomere repeat amplification protocol) showed higher activity with the three codon-optimized hTERT versions compared to hTERT-v1, with hTERT-ID having the highest activity FIG. 2).

Figure 3:
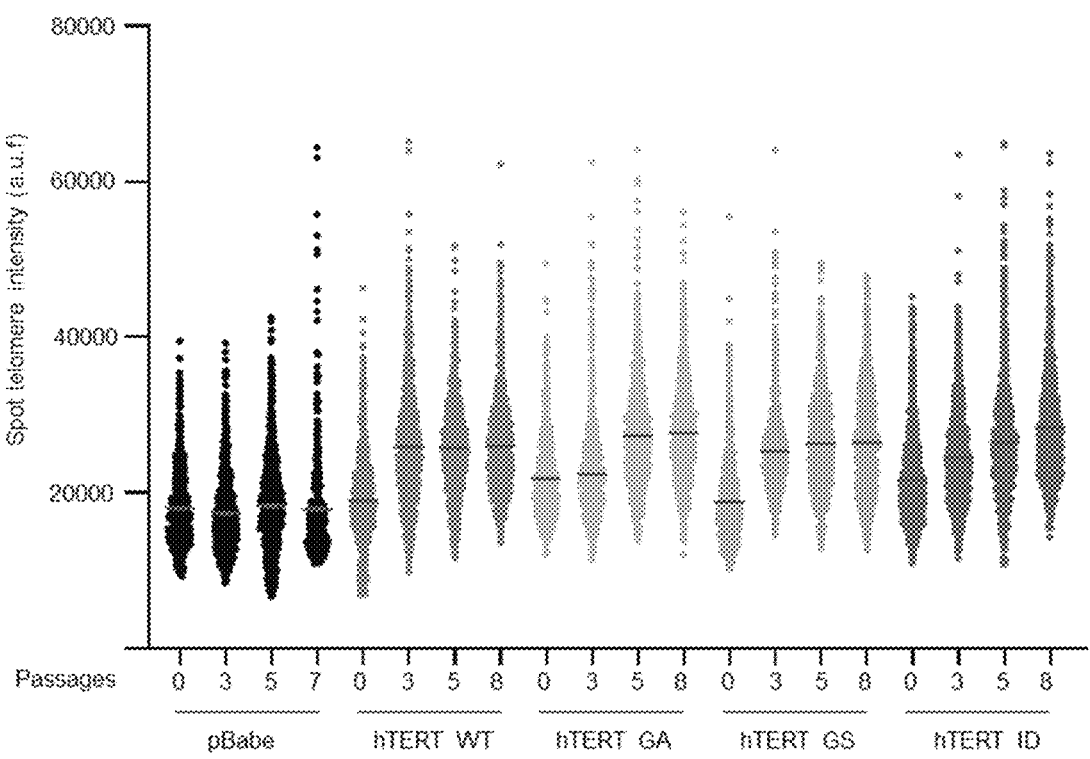
FIG. 3. BJ human fibroblasts were retrovirally transduced with pBabe-hTERT-WT, pBabe-hTERT-GA, pBabe-hTERT-GS and pBabe-hTERT-ID and telomere lengthening through successive passages (p0, p3, p5, and p7) was analyzed by q-Fish.

BJ fibroblasts transduced with the three-codon optimized human telomerase genes (GA, GS, and ID) and the wildtype TERT (v1) were successively passaged in cell culture FIG. 3). Q-Fish analysis in metaphase spreads were performed at passages 0, 3, 5, and 8 to quantitatively measure telomere length.

A progressive telomere lengthening and decrease in the percentage of short telomeres (below 20,000 Arbitrary units of fluorescence (a.u.f.) was observed with the four telomerase gene versions. The rate of telomere lengthening was similar with v1, GA, GS, and ID. Of note, telomere length did not increase in the negative control, pBabe-GFP transduced BJ fibroblasts, and these entered became senescent at passage 7.

The results show that the four TERT alleles lengthen telomeres in human cells. No differences in the lengthening rate were observed among hTERT-WT, hTERT-GA, hTERT-GS, and hTERT-ID. hTERT-ID was chosen as the TERT transgene as it showed the highest activity in the TRAP assay (FIG. 2) hTERT-ID is referred to as hTERT from herein after.

Figure 4:
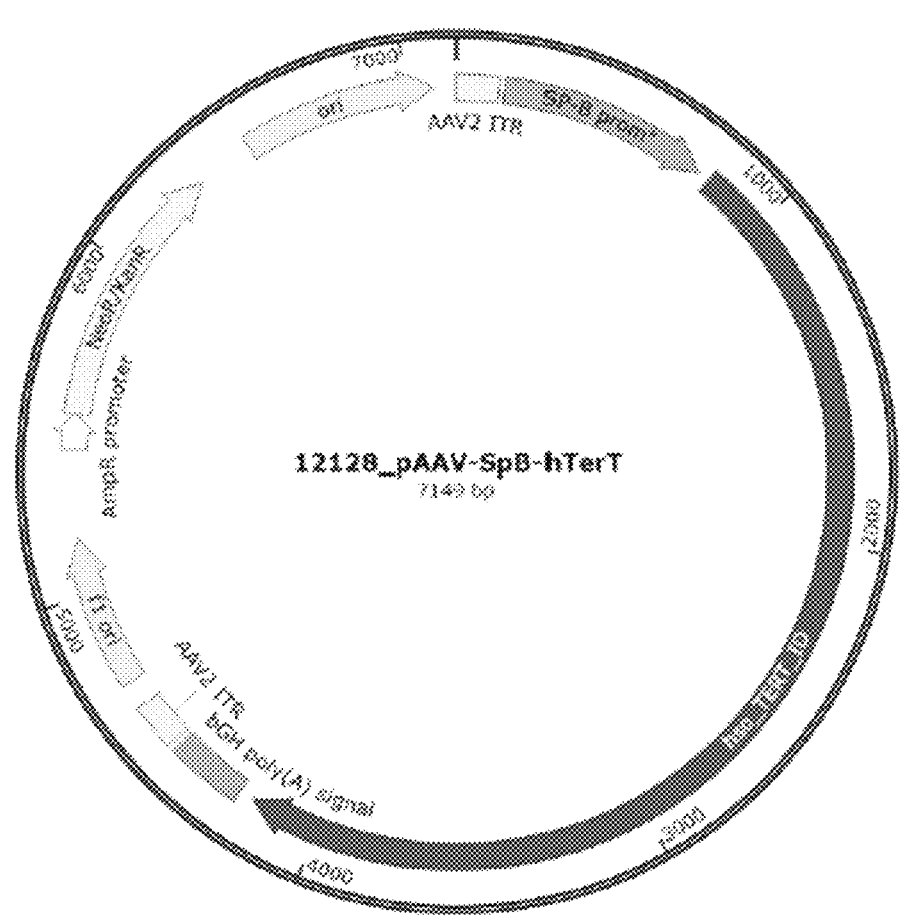
FIG. 4. AAV-TERT-01: AAV6.2-SpB-hTERT sequence map.

AAV-TERT-01, also called AAV6.2-SpB-hTERT, was selected as the clinical product to be manufactured and tested in clinical studies due to the known tropism of AAV6.2 capsid to human lung organoids and NHP lung. Both SpB-GFP and the SpB-null control vectors will be produced in parallel. The sequence of AAV-TERT-01 is depicted in FIG. 4.

Example 2: Experiments with AAV6.2-SpB-hTERT (AAV-TERT-01)

Research Grade Small Batch Production of AAV6.2-SpB-hTERT (AAV-TERT-01)

Overview

AAV6.2 was selected as the candidate serotype to be used in the clinical product. Transgene AAV6.2 plasmid production was carried out at Sirion Biotech (Revvity) to generate a batch of viral particles for use in nonclinical studies in mouse and human cells and to assess transduction efficacy and tropism. The vectors described below were generated, including a control (GFP) vector and a vector with the human transgene (hTERT).

a) AAV6.2-SpB-hTERT
    Gene of Interest (GOI): hTERT-ID
    Organism: human
    Ref Seq.: NM_198253.3
    Length of coding region: 3396 bp
    Cloned as: SpB-hso Tert-bGHpA
b) AAV6.2-SpB-GFP
    Gene of Interest (GOI): GFP
    Length of coding region: 717 bp
    Cloned as: SpB-GFP-bGHpA
    Vector cloning success was verified by restriction analysis and DNA sequencing.

Vector Quality Control
    Plasmid Purification: Endo-free plasmid Mega Kit (Qiagen)
    Integrity of ITRs: Confirmed by restriction analysis.

Upstream Process

TABLE 1

Packaging and helper plasmids (Triple transfection system).

| Vector Name | Rep-Cap plasmid | Helper plasmid | Expression plasmid |
|---|---|---|---|
| AAV6.2-SpB-hTERT | pRep2-Cap6.2 (F129L) | pHelper | P12128 |
| AAV6.2-SpB-GFP | pRep2-Cap6.2 (F129L) | pHelper | P11306 |

Production scale: 4×240 ml, 1×240 ml and 1×120 ml suspension, respectively.

Production cell line: HEK293 based Suspension Cell line.

Transfection reagent: AAV-MAX Transfection Reagent.

Virus harvest: 72 h after transfection.

AAV particles isolated: from cells.

Downstream Process

Crude Lysate preparation: 0.1% Triton lysis of cell Pellet+ Endonuclease digest.

Purification step 1: Primary capture with Poros Capture-Select AAV-X (ThermoFisher).

Purification step 2: Iodixanol gradient centrifugation (enrichment of full capsids).

Concentration/Formulation: Amicon ULTRA 15, Ultracel PL Membrane, 100 kDa.

Formulation buffer: PBS+0.001% Pluronic F68.

Sterile filtration: Acrodisc PP, PES, 0.2 µM 1 cm2.

Storage: 2 ml cryovial at −80° C. in sterile PP-screw-cap vial (Sarstedt).

Quality Control

Titration of viral particles (Vector genome titer) was performed by ddPCR using a QX200™ Droplet Digital™ PCR System, BioRad using ITR specific PCR-primer. A first titration was performed after formulation and sterile filtration. The titer of the AAV particles was adjusted to 2.0E+13 VG/ml with formulation buffer followed by aliquoting and freezing. One aliquot of the frozen batch was thawed, and the titer of the diluted sample was measured by qPCR. ELISA titer and ratio of total/full capsids were determined for the AAV6.2-SpB-hTERT sample. Finally, the percentage of empty/full capsids and DLS measurement was obtained with the stunner instrument (Unchained Labs) for the three samples (see table below). Particle titer was performed by AAV6 ELISA (Progen)

TABLE 2

AAV Samples qPCR measurements.

| AAV sample | Adjusted qPCR titer | Final ddPCR titer | Full capsids (%) |
|---|---|---|---|
| AAV6.2-SpB-hTERT | 1.0E+13 vg/ml | $1.1 \times 10^{13}$ vg/ml | 75% |
| AAV6.2-SpB-GFP | 1.0E+12 vg/ml | $1.6 \times 10^{12}$ vg/ml | 78% |

Note:
Titer was assessed by ddPCR using an automated software (BioRad) to calculate the titer based on a preset volume (mathematically based on Poisson-distribution).
The given dilution factor of the sample is considered for finalized and reported titer.
The available volume of each sample calculates the total amount of vg.

TABLE 3

AAV Samples DLS measurements.

| AAV sample | Capsid intensity | Aggregate intensity | Capsid diameter | Polydispersity Index (PdI) |
|---|---|---|---|---|
| AAV6.2-SpB-hTERT | 78.27 | 21.73 | 26.60 | 0.18 |
| AAV6.2-SpB-GFP | 80.87 | 19.13 | 26.13 | 0.13 |

Purity Check

Figures 5A, 5B:
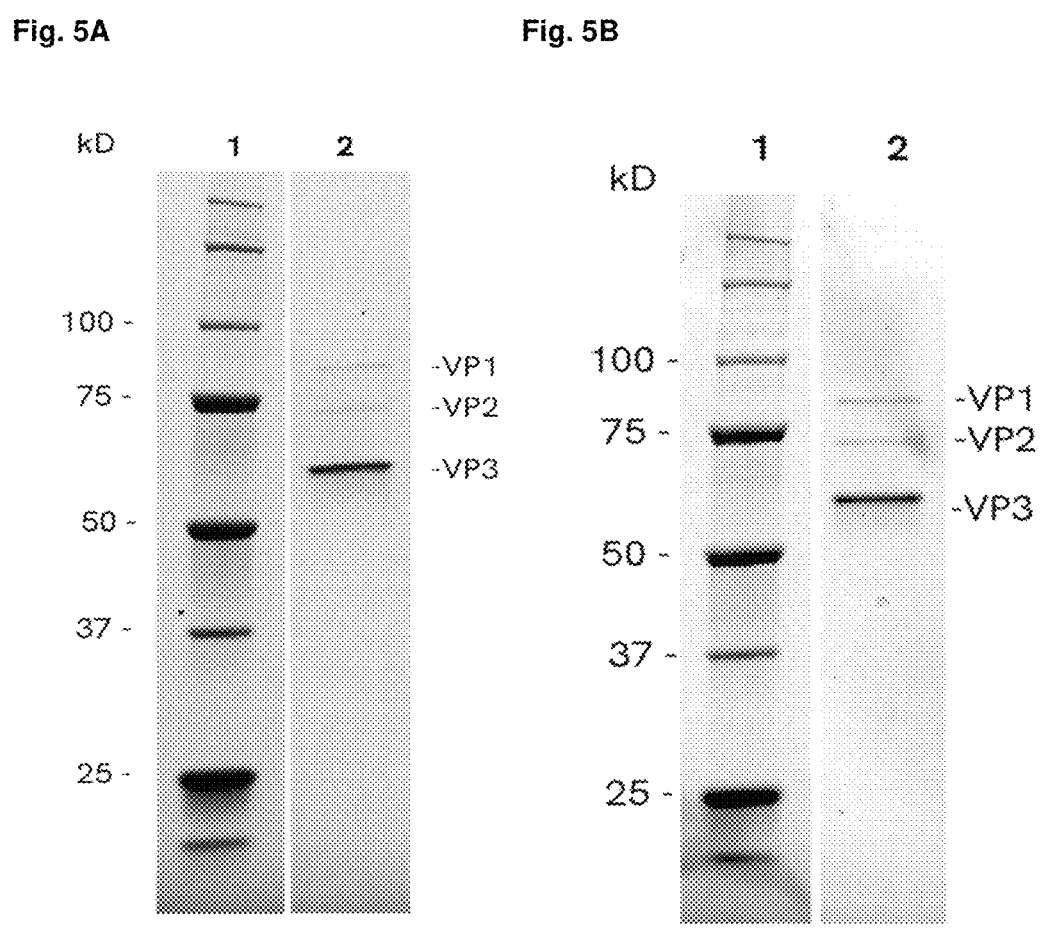

Protein present in the final product and corresponding to 5.0E+10 VG was separated on a 10% SDS PAGE using Stain technology (Biorad) for visualization of proteins. Only VP1, VP2, and VP3 proteins are detectable indicating a purity of the AAV preparation of >95% (FIG. 5). The software applied by the instrument (BioRad) was used to calculate the signal intensity of each lane. A general purity of >95% (provided by the software) was set as a lower acceptance limit.

Integrity Check of Packaged Vector Genomes

DNA contained in 4.0E+10 VG of each of the final product was separated on a 0.8% agarose gel and was stained with gel red. FIG. 6b shows a single sharp band of about 4.6 kb which corresponds well to the size of the packaged vector genome (AAV6.2-SpB-hTERT) which is 4639 bp, demonstrating its integrity in the AAV particles. Finally, FIG. 6c shows a single sharp band of about 2.1 kb which corresponds well to the size of the packaged vector genome (AAV6.2-SpB-GFP) which is 2119 bp, thereby demonstrating its integrity in the AAV particles.

Endotoxin Test

Endotoxin levels in the final product were determined using the Endosafe-exgen-PT Spectrometer from Charles River Laboratories (CRL). The result is shown below:

AAV6.2-SpB-hTERT<1.0 EU/2.0 E+13 vg

AAV6.2-SpB-GFP<1.0 EU/2.0E+13 vg

Detection limit: 1.0 EU/ml.

Methods are internally validated or measured in relation to an external reference standard. Acceptance criteria are defined by SOP.

In Vitro Models and Transduction

H441 cell culture and transduction: H441 cells were seeded in 6 well culture plates. After 24 hours, media was replaced with culture media containing 1 uM dexamethasone and cells were cultured for 3 days. AAVs were then added at various concentrations and cells were harvested 48 hours later by trypsinization for flow cytometry of GFP, RNA RNA extraction for RT-qPCR and protein isolation for TRAP activity assay.

The liver epithelial cell line HEP G2 and the liver endothelial cell line SK-HEP-1 were seeded, and once confluent, were transduced with AAVs at various concentrations (vg/cell). Following 48 hours, cells were harvested for flow cytometry for GFP or RNA isolation for RT-qPCR.

Lung Fibroblast cell culture and transduction: Human lung fibroblasts (BA196) were cultured and transduced with AAVs at various concentrations for 72 hours followed by harvest for flow cytometry, RNA RT-qPCR or TRAP analysis.

Primary AT2 cell isolation, culture and transduction: Epithelial cells from human lung lobectomies were isolated using EPCAM+ selection. Cells were then seeded in a Matrigel droplet (3D) and were allowed to form organoids. Organoids were then cultured for a minimum of 5 days before AAV transduction for 5 or 7 days. Organoids were either passaged or harvested after 10 days of culture for flow cytometry, RNA RT-qPCR, or TRAP analysis.

hTERT functional testing: WT and codon-optimized hTERT transgenes were cloned into pBABe vector. Transduced cells were selected with puromycin, passaged, and assayed for Tert expression levels, and telomerase activity (TRAP). Telomere length was analyzed after 6 passages by q-Fish in metaphase spreads.

Technical Assays for Measuring Telomerase Activity and Telomere Lengthening

In vitro models as well as in vivo model utilized sensitive technical assays to measure telomerase expression and telomere lengthening. Telomeric repeats amplification protocol (TRAP) was used to measure telomerase activity and has been previously described (Blasco et al. 1997). High-Throughput Quantitative Fluorescence In Situ Hybridization (HT-Q-FISH) analysis was used to label telomeres with a probe that recognizes telomeric units (TTAGGG), and confocal images were captured using the Opera Phenix High-Content Screening System (PerkinElmer). Images were analyzed with Harmony High-Content Analysis Software (PerkinElmer).

Results

AAV6.2-SpB-hTERT can be Expressed and Active in H441 Cells

To determine if AAV-TERT-01 (AAV6.2-SpB-hTERT) can transduce human lung AT2 cells, the cells that are damaged in IPF, H441 cells, a fast-growing lung adenocarcinoma cell line with phenotypic and functional properties of primary AT2 cells were used. H441 cells could be induced to turn on and maintain SpB expression upon treatment with the corticosteroid, Dexamethasone (Dex) suggesting that the SpB promoter could be expressed in this cell type (FIG. 7).

Next, we wanted to utilize the H441 cell line to compare the expression of a transgene packaged in an AAV vector utilizing a ubiquitous CMV promoter or the lung specific SpB promoter. Therefore, H441 cells were transduced with AAV6 expressing GFP downstream of SpB or CMV or with AAV6.2-SpB-GFP, our therapeutic capsid: promoter combination. As demonstrated in FIG. 8A, all three vectors were able to transduce H441 cells and express GFP compared to untreated and AAV-null vector. CMV-driven GFP expression was higher than SpB utilizing the same capsid (AAV6), which is consistent with strong CMV promoter activity. Additionally, AAVs packaging SpB-hTERT cargo were used to transduce H441 cells following Dex treatment and resulted in an increase in hTERT activity, 48 hours after transduction suggesting that hTERT can be expressed and active in AT2-like H441 cells (FIG. 8B).

AAV6.2-SpB is Silent in Liver Cells

Commonly used AAV capsids combined with ubiquitous promoters distribute to and drive target gene expression in the liver and have some amount of liver toxicity when delivered intravenously, which is increased at higher doses. AAV-TERT-01, however, utilizes a tissue-specific promoter, human SpB to lessen or eliminate non-lung expression of hTERT. To confirm lack of liver expression with AAV-TERT-01, liver epithelial and endothelial cell lines were tested for permissibility of transduction and expression from lung SpB promoter.

Figure 9:
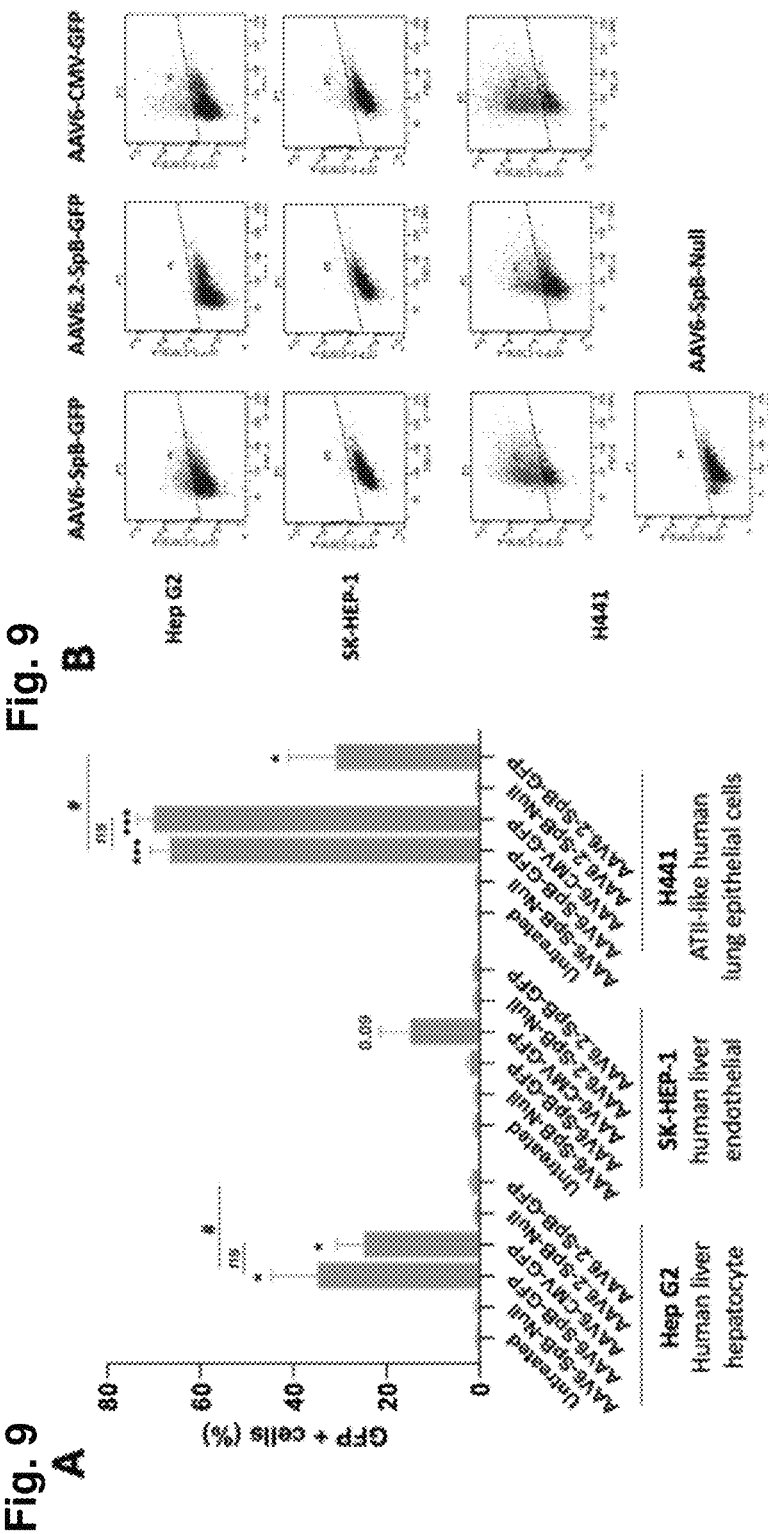

The liver epithelial cell line (HEPG2) and liver endothelial cell line (SK-HEP-1) were treated with $7.5 \times 10^4$ vg/cell of GFP packaged in AAV6.2-SpB, which is the capsid: promoter combination in AAV-TERT-01 or AAV6 combined with CMV or SpB promoters (FIG. 9). Surprisingly, in contrast to serotype AAV6, a capsid known to transduce human liver hepatocytes, AAV6.2-SpB-GFP did not result in GFP expression in either liver cell line, while it did drive expression in the AT2-like H441 lung cell line. SpB promoter did not restrict expression in hepatocyte cell line using AAV6 capsid but did restrict expression in endothelial cell line.

These data demonstrate that the combination of AAV6.2 capsid and SpB promoter restricts transgene expression in liver cell lines. This effect is only seen with the AAV6.2-SpB combination. The leakiness of the SpB promoter in hepatocytes (HepG2) when delivered by AAV6 may be due to strong hepatocyte transduction by AAV6. In contrast, liver endothelial cells (SK-HEP-1) do not express AAV6-SpB-GFP, perhaps due to lower transduction (visible by lower expression of AAV6-CMV-GFP) or better silencing of SpB promoter in liver endothelial cells. Importantly, AAV6.2-SpB-GFP showed no expression in either liver cell line, suggesting this capsid promoter combination restricts liver expression. This demonstrates that AAV-TERT-01 has unique specificity for lung and should prevent liver toxicity when delivered systemically.

SpB Promoter is Silent in Fibroblasts

Figure 10:
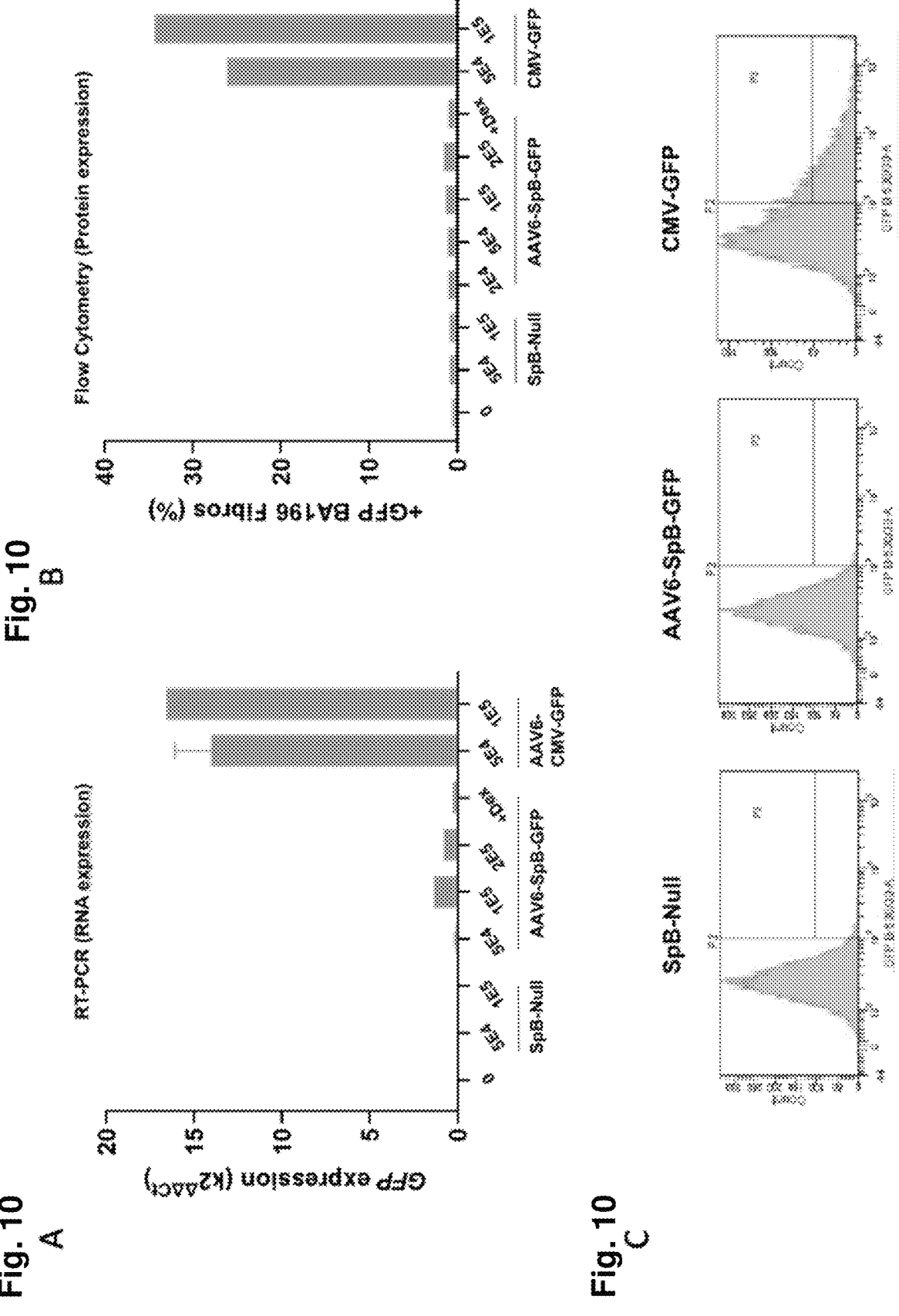

Next, we wanted to confirm that other lung cell types would not express AAV-TERT-01, particularly lung fibroblasts. Activation and proliferation of collagen-secreting myofibroblasts are key hallmark of fibrosis and extending the proliferative potential of these fibroblasts through telomerase expression should be derisked. Therefore, primary human lung fibroblasts were cultured and transduced with ascending doses of AAVs utilizing SpB or CMV promoter from $5 \times 10^4$ to $2 \times 10^5$ vg/cell. After 72 hours, cells were harvested for RNA collection or flow cytometry. AAV6 transduction is evidenced by high expression of GFP mRNA and GFP protein using ubiquitous CMV promoter. However, SpB promoter usage results in little to no GFP mRNA and GFP expression by flow cytometry in fibroblasts (FIG. 10).

These data demonstrate that use of the SpB promoter in AAV-TERT-01 will silence or restrict expression in non-target cells, even those permissive to AAV transduction.

Dose-Dependent hTERT Expression from AAV-TERT-01 in Primary AT2 Cells

Primary human AT2 cells models have been developed in-house to measure telomere lengthening and the effect on stemness and fibrotic signaling. Although H441 cells have been demonstrated to show permissiveness to AAV-TERT-01 transduction and expression, endogenous telomerase expression and activity make them incompatible for measuring TERT protein and telomerase activity long term. AT2 cells derived from biopsied human lung tissue can be cultured as 3D organoids to maintain SPB mRNA expression across multiple passages and demonstrate low endogenous telomerase activity (FIG. 11). Furthermore, they can express therapeutic hTERT (hTERT-ID) expressed by SpB promoter after 5 days with AAV treatment (FIG. 11). Additionally, a dose response using AAVs expressing GFP by SpB promoter demonstrates dose dependent increase in GFP protein in 3D organoids 5 days after treatment. (FIG. 12).

The invention claimed is:

1. A recombinant adeno-associated virus (rAAV) particle comprising:
   a) a recombinant nucleic acid comprising a lung-specific SpB promoter and a therapeutic gene, wherein the lung-specific SpB promoter comprises SEQ ID NO: 1, and wherein the lung-specific SpB promoter is operably linked to the therapeutic gene, and
   b) an AAV capsid of 6.2 serotype.

2. The rAAV particle of claim 1, wherein the therapeutic gene encodes for human telomerase reverse transcriptase (TERT).

3. The rAAV particle of claim 1, wherein the therapeutic gene encodes a protein comprising SEQ ID NO: 2 or 3.

4. The rAAV particle of claim 1 wherein the AAV capsid of 6.2 serotype comprises a VP1 protein comprising SEQ ID NO: 15.

5. The rAAV particle of claim 1, wherein the therapeutic gene comprises SEQ ID NO: 8, 9, 11, 12, or 13.

6. The rAAV particle of claim 5, wherein the therapeutic gene comprises SEQ ID NO: 11.

7. The rAAV particle of claim 1, wherein the recombinant nucleic acid of a) further comprises a Kozak sequence upstream of the therapeutic gene.

8. The rAAV particle of claim 7, wherein the Kozak sequence comprises SEQ ID NO: 4.

9. The rAAV particle of claim 1, wherein the recombinant nucleic acid of a) further comprises a polyadenylation (Poly-A) signal placed downstream of the therapeutic gene.

10. The rAAV particle of claim 9, wherein the Poly-A signal is a bovine growth hormone polyadenylation signal.

11. The rAAV particle of claim 1, wherein the recombinant nucleic acid of a) further comprises a 5'-end and 3'-end inverted terminal repeat (ITR) sequences from AAV serotype 2 (AAV2).

12. The rAAV particle of claim 11, wherein the 5'-end and 3'-end AAV2 ITR sequences comprise SEQ ID NO: 6 and 7, respectively.

13. The rAAV particle of claim 1, wherein the recombinant nucleic acid of a) comprises SEQ ID NO: 10.

14. A method of treating or preventing a lung disease comprising administering the rAAV particle of claim 1 to a subject in need thereof.

15. The method of claim 14, wherein the recombinant nucleic acid of a) comprises SEQ ID NO: 10.

16. The method of claim 14, wherein the lung disease is pulmonary fibrosis.

17. The method of claim 16, wherein the pulmonary fibrosis is idiopathic pulmonary fibrosis.

* * * * *

SEQUENCE LISTING

Sequence total quantity: 16
SEQ ID NO: 1                moltype = DNA   length = 632
FEATURE                     Location/Qualifiers
source                      1..632
                            mol_type = other DNA
                            organism = synthetic construct
SEQUENCE: 1
atagggctgt ctgggagcca ctccagggcc acagaaatct tgtctctgac tcagggtatt   60
ttgtttttctg ttttgtgtaa atgctcttct gactaatgca aaccatgtgt ccatagaacc  120
agaagatttt tccaggggaa aaggtaagga ggtggtgaga gtgtcctggg tctgcccttc  180
cagggcttgc cctgggttaa gagccaggca ggaagctctc aagagcattg ctcaagagta  240
gaggggggcct gggaggccca gggaggggat gggaggggaa cacccaggct gcccccaacc  300
agatgccctc caccctcctc aacctccctc ccacggcctg gagaggtggg accaggtatg  360
gaggcttgag agcccctggt tggaggaagc cacaagtcca ggaacatggg agtctgggca  420
gggggcaaag gaggcaggaa caggccatca gccaggacag gtggtaaggc aggcaggagt  480
gttcctgctg ggaaaaggtg ggatcaagca cctggagggc tcttcagagc aaagacaaac  540
actgaggtcg ctgccactcc tacagagccc ccacgccccg cccagctata aggggccatg  600
caccaagcag ggtacccagg ctgcagaggt gc                                632

SEQ ID NO: 2                moltype = AA   length = 1132
FEATURE                     Location/Qualifiers
source                      1..1132
                            mol_type = protein
                            organism = Homo sapiens
SEQUENCE: 2
MPRAPRCRAV RSLLRSHYRE VLPLATFVRR LGPQGWRLVQ RGDPAAFRAL VAQCLVCVPW   60
DARPPPAAPS FRQVSCLKEL VARVLQRLCE RGAKNVLAFG FALLDGARGG PPEAFTTSVR  120
SYLPNTVTDA LRGSGAWGLL LRRVGDDVLV HLLARCALFV LVAPSCAYQV CGPPLYQLGA  180
ATQARPPPHA SGPRRRLGCE RAWNHSVREA GVPLGLPAPG ARRRGGSASR SLPLPKRPRR  240
GAAPEPERTP VGQGSWAHPG RTRGPSDRGF CVVSPARPAE EATSLEGALS GTRHSHPSVG  300
RQHHAGPPST SRPPRPWDTP CPPVYAETKH FLYSSGDKEQ LRPSFLLSSL RPSLTGARRL  360
VETIFLGSRP WMPGTPRRLP RLPQRYWQMR PLFLELLGNH AQCPYGVLLK THCPLRAAVT  420
PAAGVCAREK PQGSVAAPEE EDTDPRRLVQ LLRQHSSPWQ VYGFVRACLR RLVPPGLWGS  480
RHNERRFLRN TKKFISLGKH AKLSLQELTW KMSVRDCAWL RRSPGVGCVP AAEHRLREEI  540
LAKFLHWLMS VYVVELLRSF FYVTETTFQK NRLFFYRKSV WSKLQSIGIR QHLKRVQLRE  600
LSEAEVRQHR EARPALLTSR LRFIPKPDGL RPIVNMDYVV GARTFRREKR AERLTSRVKA  660
LFSVLNYERA RRPGLLGASV LGLDDIHRAW RTFVLRVRAQ DPPPELYFVK VDVTGAYDTI  720
PQDRLTEVIA SIIKPQNTYC VRRYAVVQKA AHGHVRKAFK SHVSTLTDLQ PYMRQFVAHL  780
QETSPLRDAV VIEQSSSLNE ASSGLFDVFL RFMCHHAVRI RGKSYVQCQG IPQGSILSTL  840
LCSLCYGDME NKLFAGIRRD GLLLRLVDDF LLVTPHLTHA KTFLRTLVRG VPEYGCVVNL  900
RKTVVNFPVE DEALGGTAFV QMPAHGLFPW CGLLLDTRTL EVQSDYSSYA RTSIRASLTF  960
NRGFKAGRNM RRKLFGVLRL KCHSLFLDLQ VNSLQTVCTN IYKILLLQAY RFHACVLQLP 1020
FHQQVWKNPT FFLRVISDTA SLCYSILKAK NAGMSLGAKG AAGPLPSEAV QWLCHQAFLL 1080
KLTRHRVTYV PLLGSLRTAQ TQLSRKLPGT TLTALEAAAN PALPSDFKTI LD          1132

SEQ ID NO: 3                moltype = AA   length = 1069
FEATURE                     Location/Qualifiers
source                      1..1069
                            mol_type = protein
                            organism = Homo sapiens
SEQUENCE: 3
MPRAPRCRAV RSLLRSHYRE VLPLATFVRR LGPQGWRLVQ RGDPAAFRAL VAQCLVCVPW   60
DARPPPAAPS FRQVSCLKEL VARVLQRLCE RGAKNVLAFG FALLDGARGG PPEAFTTSVR  120
SYLPNTVTDA LRGSGAWGLL LRRVGDDVLV HLLARCALFV LVAPSCAYQV CGPPLYQLGA  180
ATQARPPPHA SGPRRRLGCE RAWNHSVREA GVPLGLPAPG ARRRGGSASR SLPLPKRPRR  240
GAAPEPERTP VGQGSWAHPG RTRGPSDRGF CVVSPARPAE EATSLEGALS GTRHSHPSVG  300
RQHHAGPPST SRPPRPWDTP CPPVYAETKH FLYSSGDKEQ LRPSFLLSSL RPSLTGARRL  360
VETIFLGSRP WMPGTPRRLP RLPQRYWQMR PLFLELLGNH AQCPYGVLLK THCPLRAAVT  420
PAAGVCAREK PQGSVAAPEE EDTDPRRLVQ LLRQHSSPWQ VYGFVRACLR RLVPPGLWGS  480
RHNERRFLRN TKKFISLGKH AKLSLQELTW KMSVRDCAWL RRSPGVGCVP AAEHRLREEI  540
LAKFLHWLMS VYVVELLRSF FYVTETTFQK NRLFFYRKSV WSKLQSIGIR QHLKRVQLRE  600
LSEAEVRQHR EARPALLTSR LRFIPKPDGL RPIVNMDYVV GARTFRREKR AERLTSRVKA  660
LFSVLNYERA RRPGLLGASV LGLDDIHRAW RTFVLRVRAQ DPPPELYFVK VDVTGAYDTI  720
PQDRLTEVIA SIIKPQNTYC VRRYAVVQKA AHGHVRKAFK SHVSTLTDLQ PYMRQFVAHL  780
QETSPLRDAV VIEQSSSLNE ASSGLFDVFL RFMCHHAVRI RGKSYVQCQG IPQGSILSTL  840
LCSLCYGDME NKLFAGIRRD GLLLRLVDDF LLVTPHLTHA KTFLSYARTS IRASLTFNRG  900
FKAGRNMRRK LFGVLRLKCH SLFLDLQVNS LQTVCTNIYK ILLLQAYRFH ACVLQLPFHQ  960
QVWKNPTFFL RVISDTASLC YSILKAKNAG MSLGAKGAAG PLPSEAVQWL CHQAFLLKLT 1020
RHRVTYVPLL GSLRTAQTQL SRKLPGTTLT ALEAAANPAL PSDFKTILD             1069

SEQ ID NO: 4                moltype =    length =
SEQUENCE: 4
000

SEQ ID NO: 5                moltype = DNA   length = 225
FEATURE                     Location/Qualifiers
source                      1..225
                            mol_type = other DNA

```
                              organism = synthetic construct
SEQUENCE: 5
ctgtgccttc tagttgccag ccatctgttg tttgcccctc ccccgtgcct tccttgaccc      60
tggaaggtgc cactcccact gtcctttcct aataaaatga ggaaattgca tcgcattgtc     120
tgagtaggtg tcattctatt ctgggggggtg gggtggggca ggacagcaag ggggaggatt    180
gggaagacaa tagcaggcat gctgggggatg cggtgggctc tatgg                    225

SEQ ID NO: 6                  moltype = DNA   length = 130
FEATURE                       Location/Qualifiers
source                        1..130
                              mol_type = other DNA
                              organism = synthetic construct
SEQUENCE: 6
cctgcaggca gctgcgcgct cgctcgctca ctgaggccgc ccgggcgtcg ggcgaccttt      60
ggtcgcccgg cctcagtgag cgagcgagcg cgcagagagg gagtggccaa ctccatcact     120
aggggttcct                                                            130

SEQ ID NO: 7                  moltype = DNA   length = 141
FEATURE                       Location/Qualifiers
source                        1..141
                              mol_type = other DNA
                              organism = synthetic construct
SEQUENCE: 7
aggaacccct agtgatggag ttggccactc cctctctgcg cgctcgctcg ctcactgagg      60
ccgggcgacc aaaggtcgcc cgacgcccgg gctttgcccg ggcggcctca gtgagcgagc     120
gagcgcgcag ctgcctgcag g                                               141

SEQ ID NO: 8                  moltype = DNA   length = 3399
FEATURE                       Location/Qualifiers
source                        1..3399
                              mol_type = genomic DNA
                              organism = Homo sapiens
SEQUENCE: 8
atgccgcgcg ctccccgctg ccgagccgtg cgctccctgc tgcgcagcca ctaccgcgag      60
gtgctgccgc tggccacgtt cgtgcggcgc ctgggggcccc agggctggcg gctggtgcag     120
cgcgggggacc cggcggcttt ccgcgcgctg gtgggcccagt gcctggtgtg cgtgccctgg    180
gacgcacggc cgcccccccgc cgcccccctcc ttccgccagg tgtcctgcct gaaggagctg    240
gtggcccgag tgctgcagag gctgtgcgag cgcgcgcgca agaacgtgct ggccttcggc      300
ttcgcgctgc tggacggggc ccgcgggggc cccccagggg ccttcaccac cagcgtgcgc     360
agctacctgc ccaacacggt gaccgacgca ctgcgggggg cgggggcgtg ggggctgctg     420
ctgcgccgcg tgggcgacga cgtgctggtt cacctgctgg cacgctgcgc gctctttgtg     480
ctggtggctc ccagctgcgc ctaccaggtg tgcgggccgc cgctgtacca gctcggcgct    540
gccactcagg cccggccccc gccacacgct agtggaccgc gaaggcgtct gggatgcgaa     600
cgggcctgga accatagcgt cagggaggcc ggggtccccc tgggcctgcc agccccgggt     660
gcgaggaggc gcgggggcag tgccagccga agtctgccgt gcccaagag gcccaggcgt     720
ggcgctgccc ctgagccgga gcggacgccc gttgggcagg ggtcctgggc ccacccgggc     780
aggacgcgtg gaccgagtga ccgtggtttc tgtgtggtgt cacctgccag acccgccgaa     840
gaagccacct cttttggaggg tgcgctctct ggcacgcgcc actcccaccc atccgtgggc     900
cgccagcacc acgcgggccc cccatccaca tcgcggccac cacgtccctg ggacacgcct     960
tgtccccccgg tgtacgccga gaccaagcac ttcctctact cctcaggcga caaggagcag    1020
ctgcggcccct ccttcctact cagctctctg aggcccagcc tgactggcgc tcggaggctc    1080
gtggagacca tctttctggg ttccaggccc tggatgccag ggactcccg caggttgccc     1140
cgcctgcccc agcgctactg gcaaatgcgg ccctgtttc tggagctgct tgggaaccac     1200
gcgcagtgcc cctacggggt gctcctcaag acgcactgcc cgctgcgagc tgcggtcacc     1260
ccagcagcg gtgtctgtgc ccgggagaag ccccagggct ctgtggccgc cccgaggag     1320
gaggacacag accccccgtcg cctggtgcag ctgctccgcc agcacagcag ccctggcag    1380
gtgtacggct tcgtgcgggc ctgcctgcgc cggctggtgc ccccaggcct ctggggctcc    1440
aggcacaacg aacgccgctt cctcaggaac accaagaagt tcatctccct ggggaagcat    1500
gccaagctct cgctgcagga gctgacgtgg aagatgagcg tgcgggactg cgcttggctg    1560
cgcaggagcc caggggttgg ctgtgttccg gccgcagagc accgtctgcg tgaggagatc    1620
ctggccaagt tcctgcactg gctgatgagt gtgtacgtcg tcgagctgct caggtctttc    1680
tttatgtca cggagaccac gtttcaaaag aacaggctct tttctaccg gaagagtgtc     1740
tggagcaagt tgcaaagcat tggaatcaga cagcacttga agagggtgca gctgcgggag    1800
ctgtcggaag cagaggtcag gcagcatcgg gaagccagc cgccctgct gacgtccaga    1860
ctccgcttca tccccaagcc tgacgggctg cggccgattg tgaacatgga ctacgtcgtg    1920
ggagccagaa cgttccgcag agaaaagagg gccgagcgtc tcacctcgag ggtgaaggca    1980
ctgttcagcg tgctcaacta cgagcgggcg cggcgccccg gcctcctggg cgcctctgtg    2040
ctgggcctgg acgatatcca cagggcctgg cgcaccttcg tgctgcgtgt gcggggcccag    2100
gacccgcgc ctgagctgta ctttgtcaag gtggatgtga cgggcgcgcta cgacaccatc    2160
ccccaggaca ggctcacgga ggtcatcgcc agcatcatca aaccccagaa cacgtactgc    2220
gtgcgtcggt atgccgtggt ccagaaggcc gcccatgggc acgtccgcaa ggccttcaag    2280
agccacgtct ctaccttgac agacctccag ccgtacatgc gacagttcgt ggctcacctg    2340
caggagacca gcccgctgag ggatgccgtc gtcatcgagc agagctcctc cctgaatgag    2400
gccagcagtg gcctcttcga cgtcttccta cgcttcatgt gccaccacgc cgtgcgcatc    2460
aggggcaagt cctacgtcca gtgccagggg atcccgcagg gctccatcct ctccacgctg    2520
ctctgcagcc tgtgctacgg cgacatggag aacaagctgt ttgcggggat tcggcggga c   2580
gggctgctcc tgcgtttggt ggatgatttc ttgttggtga cacctcacct cacccacgcg    2640
aaaaccttcc tcaggaccct ggtccgaggt gtccctgagt atggctgcgt ggtgaacttg    2700
cggaagacag tggtgaactt ccctgtagaa gacgaggccc tgggtggcac ggcttttgtt    2760
```

```
cagatgccgg cccacggcct attcccctgg tgcggcctgc tgctggatac ccggaccctg   2820
gaggtgcaga gcgactactc cagctatgcc cggacctcca tcagagccag tctcaccttc   2880
aaccgcggct tcaaggctgg gaggaacatg cgtcgcaaac tctttggggt cttgcggctg   2940
aagtgtcaca gcctgtttct ggatttgcag gtgaacagcc tccagacggt gtgcaccaac   3000
atctacaaga tcctcctgct gcaggcgtac aggtttcacg catgtgtgct gcagctccca   3060
tttcatcagc aagtttggaa gaaccccaca tttttcctgc gcgtcatctc tgacacggcc   3120
tccctctgct actccatcct gaaagccaag aacgcaggga tgtcgctggg ggccaagggc   3180
gccgccggcc ctctgccctc cgaggccgtg cagtggctgt gccaccaagc attcctgctc   3240
aagctgactc gacaccgtgt cacctacgtg ccactcctgg ggtcactcag gacagcccag   3300
acgcagctga gtcggaagct cccggggacg acgctgactg ccctggaggc cgcagccaac   3360
ccggcactgc cctcagactt caagaccatc ctggactga                          3399
```

```
SEQ ID NO: 9              moltype = DNA   length = 3210
FEATURE                   Location/Qualifiers
source                    1..3210
                          mol_type = genomic DNA
                          organism = Homo sapiens
SEQUENCE: 9
atgccgcgcg ctccccgctg ccgagccgtg cgctccctgc tgcgcagcca ctaccgcgag   60
gtgctgccgc tggccacgtt cgtgcggcgc ctggggcccc agggctggcg gctggtgcag   120
cgcgggacc cggcggcttt ccgcgcgctg gtggcccagt gcctggtgtg cgtgccctgg    180
gacgcacggc cgcccccgc cgccccctcc ttccgccagg tgtcctgcct gaaggagctg    240
gtggcccgag tgctgcagag gctgtgcgag cgcggcgcga agaacgtgct ggccttcggc   300
ttcgcgctgc tggacggggc ccgcgggggc cccccgagg ccttcaccac cagcgtgcgc    360
agctacctgc ccaacacggt gaccgacgca ctgcggggga gcggggcgtg ggggctgctg   420
ctgcgcgcg tgggcgacga cgtgctggtt cacctgctgg cacgctggcg gctctttgtg    480
ctggtggctc ccagctgcgc ctaccaggtg tgcgggccgc cgctgtacca gctcggcgct   540
gccactcagg cccggcccc gccacacgct agtggacccc gaaggcgtct gggatgcgaa    600
cgggcctgga accatagcgt cagggaggcc ggggtcccc tgggcctgcc agccccgggt    660
gcgaggaggc gcgggggcag tgccagccga agtctgccgt tgcccaagag gcccaggcgt   720
ggcgctgccc ctgagccgga gcggacgccc gttgggcagg ggtcctgggc ccacccgggc   780
aggacgcgtg gaccgagtga ccgtggtttc tgtgtggtgt cacctgccag acccgccgaa   840
gaagccacct ctttggaggg tgcgctctct ggcacgcgcc actcccaccc atccgtgggc   900
cgccagcacc acgcggggcc cccatccaca tcgcggccac cacgtccctg ggacacgcct   960
tgtccccgg tgtacgccga gaccaagcac ttcctctact cctcaggcga caaggagcag   1020
ctgcggccct ccttcctact cagctctctg aggcccagcc tgactggcgc tcggaggctc   1080
gtggagacca tctttctggg ttccaggccc tggatgccag ggactccccg caggttgccc   1140
cgcctgcccc agcgctactg gcaaatgcgg ccctgtttc tggagctgct tgggaaccac    1200
gcgcagtgcc cctacggggt gctcctcaag acgcactgcc cgctgcgagc tgcggtcacc   1260
ccagcagccg gtgtctgtgc ccgggagaag ccccagggct ctgtggcggc ccccgaggag   1320
gaggacacag accccgtcg cctggtgcag ctgctccgcc agcacagcag ccctggcag    1380
gtgtacggct tcgtgcgggc ctgcctgcgc cggctggtgc ccccaggcct ctggggctcc   1440
aggcacaacg aacgccgctt cctcaggaac accaagaagt tcatctccct ggggaagcat   1500
gccaagctct cgctgcagga gctgacgtgg aagatgagcg tgcgggactg cgcttggctg   1560
cgcaggagcc caggggttgg ctgtgttccg gccgcagagc accgtctgcg tgaggagatc   1620
ctggccaagt tcctgcactg gctgatgagt gtgtacgtcg tcgagctgct caggtctttc   1680
ttttatgtca cggagaccac gtttcaaaag aacaggctct ttttctaccg gaagagtgtc   1740
tggagcaagt tgcaaagcat tggaatcaga cagcacttga agagggtgca gctgcgggag   1800
ctgtcggaag cagaggtcag gcagcatcgg gaagccaggc ccgccctgct gacgtccaga   1860
ctccgcttca tccccaagcc tgacgggctg cggccgattg tgaacatgga ctacgtcgtg   1920
ggagccagaa cgttccgcag agaaaagagg gccgagcgtc tcacctcgag ggtgaaggca   1980
ctgttcagcg tgctcaacta cgagcgggcg cggcgccccg gcctcctggg cgcctctgtg   2040
ctgggcctgg acgatatcca cagggcctgg cgcaccttcg tgctgcgtgt gcgggcccag   2100
gaccgcgc ctgagctgta ctttgtcaag gtggatgtga cgggcgcgta cgacaccatc     2160
ccccaggaca ggctcacgga ggtcatcgcc agcatcatca aacccagaa cacgtactgc     2220
gtgcgtcggt atgccgtggt ccagaaggcc gcccatgggc acgtccgcaa ggccttcaag   2280
agccacgtct ctaccttgac agacctccag ccgtacatgc gacagttcgt ggctcacctg   2340
caggagacca gcccgctgag ggatgccgtc gtcatcgagc agagctcctc cctgaatgag   2400
gccagcagtg gcctcttcga cgtcttccta cgcttcatgt gccaccacgc cgtgcgcatc   2460
aggggcaagt cctacgtcca gtgccagggg atcccgcagg gctccatcct ctccacgctg   2520
ctctgcagcc tgtgctacgg cgacatggag aacaagctgt ttgcggggat tcggcgggac   2580
gggctgctcc tgcgtttggt ggatgatttc ttgttggtga cacctcacct cacccacgcg   2640
aaaaccttcc tcagctatgc ccggacctcc atcagagcca gtctcacctt caaccgcggc   2700
ttcaaggctg ggaggaacat gcgtcgcaaa ctctttgggg tcttgcggct gaagtgtcac   2760
agcctgtttc tggatttgca ggtgaacagc ctccagacgg tgtgcaccaa catctacaag   2820
atcctcctgc tgcaggcgta caggtttcac gcatgtgtgc tgcagctccc atttcatcag   2880
caagtttgga agaaccccac atttttcctg cgcgtcatct ctgacacggc ctccctctgc   2940
tactccatcc tgaaagccaa gaacgcaggg atgtcgctgg gggccaaggg cgccgccggc   3000
cctctgccct ccgaggccgt gcagtggctg tgccaccaag cattcctgct caagctgact   3060
cgacaccgtg tcacctacgt gccactcctg gggtcactca ggacagccca gacgcagctg   3120
agtcggaagc tcccggggac gacgctgact gccctggagg ccgcagccaa cccggcactg   3180
ccctcagact tcaagaccat cctggactga                                     3210
```

```
SEQ ID NO: 10             moltype = DNA   length = 4639
FEATURE                   Location/Qualifiers
source                    1..4639
                          mol_type = other DNA
                          organism = synthetic construct
SEQUENCE: 10
```

-continued

```
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact  120
aggggttcct gcggccgcga tatcataggg ctgtctggga gccactccag ggccacagaa  180
atcttgtctc tgactcaggg tattttgttt tctgttttgt gtaaatgctc ttctgactaa  240
tgcaaaccat gtgtccatag aaccagaaga tttttccagg ggaaaaggta aggaggtggt  300
gagagtgtcc tgggtctgcc cttccagggc ttgccctggg ttaagagcca ggcaggaagc  360
tctcaagagc attgctcaag agtagagggg gcctgggagg cccagggagg ggatgggagg  420
ggaacaccca ggctgccccc aaccagatgc cctccaccct cctcaacctc cctcccacgg  480
cctggagagg tgggaccagg tatggaggct tgagagcccc tggttggagg aagccacaag  540
tccaggaaca tgggagtctg ggcaggggc aaaggaggca ggaacaggcc atcagccagg  600
acaggtggta aggcaggcag gagtgttcct gctgggaaaa ggtgggatca agcacctgga  660
gggctcttca gagcaaagac aaacactgag gtcgctgcca ctcctacaga gcccccacgc  720
cccgcccagc tataaggggc catgcaccaa gcagggtacc caggctgcag aggtgcgaat  780
tcatttaaat tctagctagc acgcgtgcca ccatgccacg agcgcccga tgcagggccg  840
tgcgaagtct cctgcgatcc cactacaggg aagtgctgcc acttgcaacg tttgtccgca  900
ggcttggggcc acaagggtgg cgccttgtac agagaggcga tcccgcggcg ttcagggcac  960
ttgttgcgca atgtctcgtg tgtgtgccct gggacgcacg gccgccccct gctgcaccat 1020
cattcaggca agtcagttgt ttgaaagaat tggtcgcccg cgtattgcag agactttgtg 1080
agagggggggc aaagaatgtc ttggcgttcg gatttgcgct tctggacgga gctaggggtg 1140
gaccacctga ggcattcacc acctcagtga gatcctacct gcccaatacg gttaccgatg 1200
ctctccgcgcg gtctggtgct tgggggttgc tccttcgaag agtgggtgat gatgtgctcg 1260
ttcacctgtt ggcgaggtgc gcgttgttcg tccttgtggc accaagctgt gcgtatcaag 1320
tttgtggacc gccgctctac cagcttggcg cagctacaca agcgcgacct ccccacacg 1380
catctggtcc cagacggcgc ctcggatgcg agcgagcgtg gaatcacagc gtgcgcgaag 1440
cgggcgtgcc tcttggcctc cccgcgccag gtgcgaggag gagaggtggt tccgcgtctc 1500
ggagccttcc gctgccgaag agaccccgac gaggagctgc gcctgaacca gagaggaccc 1560
ccgttggaca aggctcctgg gcacaccccg gccgaaccag gggcccgagc gacaggggtt 1620
tttgcgtggt aagtccagct cggcccgcag aggaagcgac gtcccttgaa ggcgcacttt 1680
ccggtactag acatagccac ccctcagtcg gaaggcagca ccacgcggga ccaccgtcta 1740
cgagccggcc acctcggccg tgggacacac cttgtcctcc tgtttatgca gagaccaaac 1800
atttcttgta tagcagcggg gacaaggaac agcttaggcc ctccttcttg ctgtcaagcc 1860
tgcgcccgtc tctgactggt gcacgccggc tggtcgagac catcttcctc gggtctaggc 1920
cgtggatgcc tggtacacct aggagattgc ctcgcctccc ccaacgatac tggcaaatga 1980
gaccgttgtt tctcgaattg ctcggcaatc atgcgcagtg cccctacggg gtcttgctta 2040
agactcattg ccctttgaga gctgctgtga cgcctgccgc cggagtgtgt gccagagaaa 2100
aaccccaggg cagtgtcgcc gccccggagg aggaagacac ggaccctagg cggttggtac 2160
aactccttcg acagcactca tctccgtggc aagtttacgg tttcgtacgg gcttgcctta 2220
ggagactcgt gccgccgggt ctctggggtt caaggcataa cgaaaggagg ttcctgcgga 2280
atacgaagaa atttatttca ttggggaaac atgcgaagct ttccttgcaa gaacttacat 2340
ggaagatgag cgtcagggac tgcgcgtggt tgaggaggtc accgggggtg ggttgcgtcc 2400
ccgccgcaga gcaccgcctt cgcgaagaga ttctcgccaa atttctccat tggctgatgt 2460
ctgtttatgt agtagaattg ttgcgctcat ttttctatgt taccgagact actttccaaa 2520
agaacagatt gttcttctac cggaaatctg tttggtcaaa acttcaatcc ataggcatta 2580
gacagcatct gaaaagggtt caattgaggg aactcagtga ggccgaggtt agacagcatc 2640
gggaggcaag gcccgctttg cttacgtcaa gacttcggtt tatacccaag ccggatggat 2700
tgcggccgat tgtaaacatg gactatgttg taggcgctcg gacgtttcgc cgcgagaagc 2760
gcgcggaacg actgacgagt agggttaagg cgttgttcag cgtgcttaac tacgaacgcg 2820
ccaggagacc tgggcttttg ggtgcatcag tcttgggtct tgatgatata caccgggcgt 2880
ggagaacatt tgttctgcga gtccgggccc aagatccccc tcccgagttg tacttcgtga 2940
aggtagatgt aactggcgcg tacgatacca tcccccaaga tagacttacg gaggttattg 3000
cctccatcat taaaccgcaa aacacgtact gcgtccgaag gtatgcagtt gtccagaagg 3060
ctgcacatgg acatgtacga aaagctttca aatcccatgt aagcaccttg accgaccttc 3120
aaccatatat gaggcaattc gtcgcgcacc tccaggagac ctcccctctc cgagatgccg 3180
tagtgatcga acaatcatct agcctgaatg aggcatcctc cggtttgttt gacgtgtttt 3240
tgcgctttat gtgtcaccac gcagttcgca ttcgcggaaa gagttatgtt caatgtcaag 3300
gaatcccccca gggaagtatc ctttccactc tcctttgtag tttgtgctac ggcgacatgg 3360
agaataagct ctttgctggc attcggaggg acggcctttt gttgaggctc gtcgacgatt 3420
tcctcctggt gacaccacat ctcactcatg ccaagacgtt cctgcggacg cttgtcagag 3480
gggttcctga gtatggatgc gtcgtcaacc ttagaaaaac agtcgtgaat ttccccgtgg 3540
aggatgaagc acttgggggc acggctttcg ttcaaatgcc tgcccacggc ctgttcccgt 3600
ggtgtggcct ccttctggat actcggaccc ttgaggttca gtcagattat tcaagctatg 3660
ccaggacgtc cattagagct tccctgacct tcaatcgagg atttaaagca gggcgcaata 3720
tgcggaggaa gctgttcggt gttcttaggt tgaagtgtca ttcactcttt cttgatcttc 3780
aagttaactc tctgcagaca gtctgtacga acatctacaa gatcttgctt ttgcaagctt 3840
accgcttcca cgcttgtgtt ctccaactgc cctttcatca acaagtgtgg aaaaacccca 3900
cgttttcct gcgagtcatc tcagacacgg ccagcctttg ctattccatc ctcaaggcta 3960
aaaacgcggg aatgtctttg ggcgctaagg gggccgcagg tccattgcca tccgaggccg 4020
tccagtggtt gtgtcaccaa gctttcttgc ttaaattgac tcggcatcgc gttacatacg 4080
ttccctcct cggctccttg agaacggcgc aaacgcagct tagccggaag cgtgccaggga 4140
cgacccttac tgcccttgaa gcggcagcga atccggcgtt gcctagcgat tttaagacta 4200
ttttggattg agtcgagcat ttaaatacgt ggagctcgct gatcagcctc gactgtgcct 4260
tctagttgcc agccatctgt tgtttgcccc tccccgtgc cttccttgac cctgaaggt 4320
gccactccca ctgtcctttc ctaataaaat gaggaaattg catcgcattg tctgagtagg 4380
tgtcattcta ttctgggggg tgggtgggg caggacagca aggggggagga ttgggaagac 4440
aatagcaggc atgctgggga tgcggtgggc tctatggcca cgtggatatc gcggccgcag 4500
gaacccctag tgatggagtt ggccactccc tctctcgcgcg ctcgctcgct cactgaggcc 4560
gggcgaccaa aggtcgcccg acgcccgggc tttgcccggg cggcctcagt gagcgagcga 4620
gcgcgcagct gcctgcagg                                              4639
```

-continued

```
SEQ ID NO: 11        moltype = DNA   length = 3399
FEATURE              Location/Qualifiers
source               1..3399
                     mol_type = other DNA
                     organism = synthetic construct
SEQUENCE: 11
atgccacgag cgccccgatg cagggccgtg cgaagtctcc tgcgatccca ctacagggaa    60
gtgctgccac ttgcaacgtt tgtccgcagg cttgggccac aagggtggcg ccttgtacag   120
agaggcgatc ccgcggcgtt cagggcactt gttgcgcaat gtctcgtgtg tgtgccctgg   180
gacgcacggc cgcccctgc tgcaccatca ttcaggcaag tcagttgttt gaaagaattg    240
gtcgcccgcg tattgcagag actttgtgag agggggcaa agaatgtctt ggcgttcgga     300
tttgcgcttc tggacggagc taggggtgga ccacctgagg cattcaccac ctcagtgaga    360
tcctacctgc ccaatacggt taccgatgct ctccgcgggt ctggtgcttg ggggttgctc    420
cttcgaagag tgggtgatga tgtgctcgtt cacctgttgg cgaggtgcgc gttgttcgtc    480
cttgtggcac caagctgtgc gtatcaagtt tgtggaccgc cgctctacca gcttggcgca    540
gctacacaag cgcgacctcc cccacacgca tctggtccca gacggcgcct cggatgcgag    600
cgagcgtgga atcacagcgt gcgcgaagcg ggcgtgcctc ttggcctccc cgcgccaggt    660
gcgaggagga gaggtggttc cgcgtctcgg agccttccgc tgccgaagag accccgacga    720
ggagctgcgc ctgaaccaga gaggacccc gttggacaag gctcctgggc acacccgggc     780
cgaaccaggg gcccgagcga caggggtttt tgcgtggtaa gtccagctcg gcccgcagag    840
gaagcgacgt cccttgaagg cgcactttcc ggtactagac atagccaccc ctcagtcgga    900
aggcagcacc acgcgggacc accgtctacg agccggccac cggcccgtg ggacacacgt      960
tgtcctcctg tttatgcaga gaccaaacat ttcttgtata gcagcgggga caaggaacag   1020
cttaggccct ccttcttgct gtcaagcctg cgcccgtctc tgactggtgc acgccggctg   1080
gtcgagacca tcttcctcgg gtctaggccg tggatgcctg gtacacctag gagattgcct   1140
cgcctccccc aacgatactg gcaaatgaga ccgttgtttc tcgaattgct cggcaatcat   1200
gcgcagtgcc cctacggggt cttgcttaag actcattgcc ctttgagagc tgctgtgacg   1260
cctgccgccg gagtgtgtgc cagagaaaaa ccccagggca gtgtcgccgc cccggaggag   1320
gaagacacgg accctaggcg gttggtacaa ctccttcgac agcactcatc tccgtggcaa   1380
gtttacggtt tcgtacgggc ttgccttagg agactcgttg cgccgggtct ctggggttca   1440
aggcataacg aaaggaggtt cctgcggaat acgaagaaat ttatttcatt ggggaaacat   1500
gcgaagcttt ccttgcaaga acttacatgg aagatgagcg tcagggactg cgcgtggttg   1560
aggaggtcac cgggggtggg ttgcgtcccc gccgcagagc accgccttcg cgaagagatt    1620
ctcgccaaat ttctccattg gctgatgtct gtttatgtag tagaattgtt gcgctcattt   1680
ttctatgtta ccgagactac tttccaaaag aacagattgt tcttctaccg gaaatctgtt   1740
tggtcaaaac ttcaatccat aggcattaga cagcatctga aaagggttca attgagggaa   1800
ctcagtgagg ccgaggttag acagcatcgg gaggcaaggc ccgctttgct tacgtcaaga   1860
cttcggttta tacccaagcc ggatggattg cggccgattg taaacatgga ctatgttgta   1920
ggcgctcgga cgtttcgccg cgagaagcgc gcggaacgac tgacgagtag ggttaaggcg   1980
ttgttcagcg tgcttaacta cgaacgcgcc aggagacctg ggcttttggg tgcatcagtc    2040
ttgggtcttg atgatataca ccgggcgtgg agaacatttg ttctgcgagt ccgggcccaa   2100
gatcccctc ccgagttgta cttcgtgaag gtagatgtaa ctggcgcgta cgataccatc     2160
ccccaagata gacttacgga ggttattgcc tccatcatta aaccgcaaaa cacgtactgc   2220
gtccgaaggt atgcagttgt ccagaaggct gcacatggac atgtacgaaa agctttcaaa   2280
tcccatgtaa gcaccttgac cgaccttcaa ccatatatga ggcaattcgt cgcgcacctc   2340
caggagacct ccctctccg agatgccgta gtgatcgaac aatcatctag cctgaatgag     2400
gcatcctccg gtttgtttga cgtgtttttg cgctttatgt gtcaccacgc agttcgcatt   2460
cgcggaaaga gttatgttca atgtcaagga atccccagg gaagtatcct ttccactctc     2520
ctttgtagtt tgtgctacgg cgacatggag aataagctct ttgctggcat cggagggac    2580
ggccttttgt tgaggctcgt cgacgatttc ctcctggtga caccacatct cactcatgcc   2640
aagacgttcc tgcggacgct tgtcagaggg gttcctgagt atggatgcgt cgtcaacctt   2700
agaaaaacag tcgtgaattt ccccgtggag gatgaagcac ttggggggcac ggctttcgtt   2760
caaatgcctg cccacggcct gttcccgtgg tgtggcctcc ttctggatac tcggaccctt   2820
gaggttcagt cagattattc aagctatgcc aggacgtcca ttagagcttc cctgaccttc    2880
aatcgaggat ttaaagcagg gcgcaatatg cggaggaagc tgttcggtgt tcttaggttg   2940
aagtgtcatt cactctttct tgatcttcaa gttaactctc tgcagacagt ctgtacgaac    3000
atctacaaga tcttgctttt gcaagcttac cgcttccacg cttgtgttct ccaactgccc   3060
tttcatcaac aagtgtggaa aaaccccacg tttttcctgc gagtcatctc agacacggcc   3120
agcctttgct attccatcct caaggctaaa aacgcgggaa tgtctttggg cgctaagggg   3180
gccgcaggtc cattgccatc cgaggccgtc cagtggttgt gtcaccaagc tttcttgctt   3240
aaattgactc ggcatcgcgt tacatacgtt ccccgtcctcg gctccttgag aacggcgcaa   3300
acgcagctta gccggaagct gccagggacg accccttactg cccttgaagc ggcagcgaat   3360
ccggcgttgc ctagcgattt taagactatt ttggattga                          3399

SEQ ID NO: 12        moltype = DNA   length = 3399
FEATURE              Location/Qualifiers
source               1..3399
                     mol_type = other DNA
                     organism = synthetic construct
SEQUENCE: 12
atgcctaggg ctcctagatg tagagccgtc agaagcctgc tgcggagcca ctatagagag    60
gtgctgcctc tggccacctt cgtgcgtaga cttggacctc aaggatggcg gctggtgcag   120
agaggcgatc ctgctgcttt tagagccctg gtggcccagt gtctcgtgtg cgttccatgg   180
gatgctgac ctccaccagc tgctcccagc ttcagacagt gtcctgcct gaaagaactg      240
gtggccaggg tgctgcagag actgtgtgaa aggggcgcca agaacgtgct ggcctttgga   300
tttgctctgc tggatggcgc tagaggcgga cctcctgagg cctttacaac aagcgtgcgg    360
agctacctgc ctaacaccgt gacagatgcc ctgagaggat ctggcgcttg gggactgctg   420
ctgagaagag tgggagatga cgtgctggtg catctgctgg ccagatgcgc tctgtttgtg   480
ctggtggctc ctagctgcgc ctaccaagtt tgtggccctc cactgtatca gctgggcgct   540
```

-continued

```
gctacacagg ctagaccacc tccacatgcc agcggaccta gaagaaggct gggctgcgaa   600
agagcctgga accactctgt tagagaagcc ggcgtgccac tgggattgcc tgcaccaggt   660
gcaagaagaa gaggcggcag cgcctctaga tctctgcctc tgcctaagag gcctagaaga   720
ggggctgccc ctgagcctga gagaacacct gttggccaag gctcttgggc ccatcctggc   780
agaacaagag gccctagcga tagaggcttc tgcgtggtgt ctcctgccag acctgccgag   840
gaagccacat ctcttgaagg cgccctgagc ggcacaagac actctcaccc atctgtgggc   900
agacagcacc atgccggacc tccaagcaca agcagaccac ctagaccttg ggacacccct   960
tgtcctccag tgtacgccga gacaaagcac ttcctgtaca gcagcggcga caaagagcag  1020
ctgaggccta gcttcctgct gtcctctctg aggccatctc tgaccggtgc tcggagactg  1080
gtggaaacca tcttcctggg cagcagacct tggatgcccg gcacacctag aaggctgcct  1140
agactgccac agcggtactg gcaaatgagg cccctgttcc tggaactgct gggcaatcac  1200
gctcagtgcc cttatggcgt gctgctgaaa acccactgtc ctctgagagc cgccgtgaca  1260
ccagcagctg gcgtttgtgc cagagagaag cctcaaggct ctgtggccgc tcctgaggaa  1320
gaggacacag atcctagacg actggtgcag ctcctgacag agcacacgtc tccatggcag  1380
gtctacggat ttgtgcgggc ctgtctgaga aggctcgttc ctcctggact gtggggctcc  1440
agacacaacg agcggcggtt tctgcggaac accaagaagt tcatcagcct gggaaagcac  1500
gccaagctga gcctgcaaga gctgacctgg aagatgagcg tgcgggattg tgcatggctg  1560
agaaggtccc caggcgtggg atgtgttcct gccgctgaac acagactgcg gaagagatc   1620
ctggccaagt tcctgcactg gctgatgtcc gtgtacgtgg tcgaactgct tcggagcttc  1680
ttctacgtga ccgagacaac cttccagaag aaccggctgt tcttctaccg gaagtccgtg  1740
tggtccaagc tgcagagcat cggcatccgg cagcatctga agagagtgca gctgagagag  1800
ctgagcgaag ccgaagtgcg gcagcacaga gaagctgaac cagctctgct gaccagcagg  1860
ctgagattca tccccaagcc tgatggcctg cggcctatcg tgaacatgga ctatgttgtg  1920
ggcgccagaa ccttttcggag agagaagaga gccgagcggc tgacctctag agtgaaggcc  1980
ctgttcagcg tgctgaacta cgagagagcc agaaggccag gactgctggg agcctctgtt  2040
ctgggactcg acgacatcca cagagcttgg cggacctttg tgctgagagt gcgagcccaa  2100
gatcctccac ctgagctgta cttcgtgaag gtggacgtga ccggcgccta cgacacaatc  2160
cctcaggaca gactgaccga agtgatcgcc agcatcatca agccccagaa cacctactgt  2220
gtgcggagat acgccgtggt gcagaaagcc gctcatggcc acgtgcggaa ggcctttaag  2280
agccatgtgt ctaccctgac cgacctgcag ccttacatga gacagttcgt ggcccatctg  2340
caagagacaa gccctctgag ggatgccgtg gtcatcgaac agagcagcag cctgaatgag  2400
gccagctccg gcctgtttga tgtgtttctc cggttcatgt gccaccacgc cgtgcggatt  2460
agaggcaaga gctacgtgca gtgccagggc attcctcagg gcagcatcct gagcacactg  2520
ctgtgcagcc tgtgctacgg cgacatggaa aacaagctgt tcgccggcat cagacgcgac  2580
ggcctgcttc tgagactggt cgacgatttc ctgctcgtga cccctcacct gacacacgcc  2640
aagacctttc tgagaacact cgtgcggggc gtgccagagt atggctgtgt ggtcaacctg  2700
agaaagaccg tggtcaactt cccgtcgag gatgaagccc ttggcggcac agctttcgtg  2760
cagatgcctg ctcatggact gttcccttgg tgcggcctgc tgctggatac cagaacactg  2820
gaagtgcaga gcgactacag cagctacgcc cggacatctca tcagagccag cctgaccttc  2880
aaccgggggct ttaaggccgg cagaaacatg cggagaaagc tgtttggagt gctgcggctg  2940
aagtgccact ctttgttct ggacctgcaa gtgaacagcc tgcagaccgt gtgcaccaac  3000
atctacaaga ttctgctgct gcaagcctac cggttccacg cctgtgttct gcagctgccc  3060
tttcaccagc aagtgtggaa gaaccctaca ttcttcctgc gcgtgatcag cgacaccgac  3120
agcctgtgtt actccatcct gaaggccaaa aacgccggca tgagcctggg agctaaaggc  3180
gctgctggac ctctgccttc tgaagcagtg cagtggctgt gtcaccaggc ctttctgctg  3240
aagctgaccc ggcacagagt gacatatgtg cctctgctgg gctccctgag aaccgctcaa  3300
acacagctga gcagaaagct gcctggcacc acactgacag ccctggaagc tgcagcaaac  3360
cctgctctgc ccagcgactt caagaccatc ctggattga                          3399
```

SEQ ID NO: 13           moltype = DNA   length = 3399
FEATURE                 Location/Qualifiers
source                  1..3399
                        mol_type = other DNA
                        organism = synthetic construct
SEQUENCE: 13

```
atgccaagag ctcctcggtg cagagccgtg cgcagcctgc tgagatccca ctaccgtgag   60
gtgctacctc tggccacctt tgtgcgcaga ctgggacctc aaggctggcg gctggtacag  120
agaggcgacc ctgccgcctt cagagcctta gtggcccagt gcctggtttg cgtgccttgg  180
gatgccggc cgcctcccgc cgctcctagc ttccggcagg tgtcctgcct gaaagaactg   240
gttgctagag tgctgcaaag actgtgcgag cgtgtgccca agaacgtgct ggccttcgga  300
tttgccctgc tggacggcgc cagaggtgga ccacccgagg ccttcacgac tagtgtccgt  360
agttacctgc caaacaccgt gacagacgcc ctgagaggct ctggcgcctg gggcctgctg   420
cttcggagag tgggcgacga tgtgctcgtt cacctgctgg cgaggtgtgc cctgttcgtg  480
ctggtgccc cttcttgtgc ttaccaggtg tgcggccctc ctctgtacca gctgggcgt   540
gcaacccagg ccagaccccc gccccacgcg agcggcccta ggcgccgcct aggttgtgaa   600
agagcatgga accacagtgt gagagaagcc ggagtgcctc tggggctgcc cgcacctggc   660
gccagaagac ggggcggctc cgcttctaga tctctgcctc tgcccaagag acctagacg   720
ggggctgctc ctgagcctga gagaactcca gtgggccagg gctcttgggc ccacccggc   780
cggaccagag gcccctctga ccggggcttc tgcgttgtga gccccgctag accagccag   840
gaggccacat ctctggaggg cgcgctaagc ggaaccagac acagccaccc ctctgtgggc  900
agacagcacc atgccggccc tccatccacc agcagacctc ccagaccttg ggacaccccg   960
tgcccccccg tgtacgccga aaccaagcac ttcctgtaca gcagcggcga taaggaacag  1020
ctgaggccta ccttcctgct gagcagctg cggcccagcc tgaccggcgc ccggagactc  1080
gttgaaacaa tcttcctggg atctagacct tggatgcccg gcaccccag acggctgcct  1140
cggctgcccc agagatactg gcagatgcgg cctctgttcc tggaactgct gggcaaccac  1200
gcccagtgtc cttacggcgt gctgctgaaa acccactgcc ctctgagagc cgccgtgaca  1260
cctgccgccg gcgtgtgcgc ccgggagaaa cctcagggca gcgtggccgc ccctgaggaa  1320
gaagacacag atcctcggag actcgtgcag ctgctgcgcg agcattccag cccttggcag  1380
gtctatggct ttgtgagagc ttgtctgcgg aggctggtgc cccctggcct gtggggaagc  1440
```

-continued

```
agacacaacg agcggagatt cctgagaaac accaagaagt tcatcagcct gggaaaacac    1500
gccaagctgt ccctgcaaga gctgacctgg aagatgtcag tgcgggactg tgcttggctg    1560
aggagaagcc ctggcgtggg atgtgtccct gccgccgaac accggctgag agaagaaatc    1620
ctggcgaaat tcctgcactg gctgatgtct gtgtacgtgg tcgagctgct gagatctttt    1680
ttctacgtga ccgagaccac ctttcagaaa aacagactgt ttttctaccg gaagagcgtg    1740
tggagcaagc tgcagtctat cggcatcaga cagcacctga agagagtgca actgagagag    1800
ctgagcgagg ccgaggtgcg gcagcaccga gaggccagac ccgccctgct gaccagcaga    1860
ctgcggttca tccctaagcc cgacggcttg cggccaatcg tgaacatgga ctacgtggtg    1920
ggcgctagaa cctttaggag agaaaagcgg gccgagagac tgacgagccg ggttaaggcc    1980
ctgttcagcg tccttaacta cgagagagcc agaagacccg gcctgctggg agcgagcgtg    2040
ctgggtttgg acgacatcca cagagcctgg agaaccttcg ttctgagagt gagagcccag    2100
gatcctcccc ccgagctgta cttcgtgaag gtggacgtga ccggcgctta cgacacaatc    2160
cctcaggaca gactgaccga ggtgatcgcc tctatcatca agcctcagaa cacatattgc    2220
gtgcggcggt acgccgtggt gcagaaggcc gcccacggcc acgtgagaaa agcctttaag    2280
agccatgtgt ccaccctcac tgatctgcaa ccctacatga gacagttcgt ggcccatctc    2340
caggagacaa gcccactgcg ggatgccgtt gtcatcgagc agagctccag ccttaatgag    2400
gcttcctctg gcctgttcga cgtgttccta cggttcatgt gccaccacgc cgtgagaatc    2460
agaggaaagt cttacgtgca gtgccagggc atcccccagg acgcatcct gagcacactg     2520
ctgtgcagcc tgtgttacgg cgacatggaa aacaagctgt tcgccggcat cagacgggat    2580
ggcctgcttc tgagattggt ggacgacttc ctgctggtga cacctcacct gacacacgct    2640
aagaccttcc tgagaacact ggtgagaggc gtgcctgagt acggctgtgt ggtgaacctg    2700
cggaagaccg tggtgaattt ccctgtggaa gacgaggccc tgggcggcac cgcctttgtg    2760
cagatgcctg cgcatggcct gttccctctg tgcggcctgc tgctggacac cagaaccctg    2820
gaagtgcaaa gcgactacag ctcttatgcc agaacctcca ttagagcctc actcacattt    2880
aaccggggct tcaaggccgg ccggaatatg agaagaaagc tgttcggcgt gctgagatta    2940
aagtgccaca gcctgttcct ggatctgcaa gtcaacagcc tgcagacagt gtgcaccaac    3000
atttacaaga ttctgctgct gcaggcttat agattccacg cctgcgtgct gcagctgccc    3060
ttccaccagc aggtctggaa aaaccccacc ttcttcctga gagtgatcag cgataccgcc    3120
agcctgtgct acagcatcct gaaggccaaa aacgccggaa tgagcctggg cgctaagggc    3180
gcagctggtc ccctgcccag cgaggccgtg cagtggctgt gccaccaggc cttcctgctt    3240
aaactgacca gacatagagt gacctacgtg ccactcctgg gaagcctccg gaccgcccaa    3300
acacagctca gccggaagct gcctggcacc acactgacag ccctggaagc cgccgctaat    3360
cctgccctgc ctagcgattt caagaccatc ctggactga                          3399
```

```
SEQ ID NO: 14            moltype = DNA  length = 2208
FEATURE                  Location/Qualifiers
source                   1..2208
                         mol_type = other DNA
                         organism = synthetic construct
SEQUENCE: 14
atggctgccg atggttatct tccagattgg ctcgaggaca acctctctga gggcattcgc    60
gagtggtggg acttgaaacc tggagccccg aaacccaaag ccaaccagca aaagcaggac   120
gacggccggg gtctggtgct tcctggctac aagtacctcg gaccctcaa cggactcgac    180
aagggggagc ccgtcaacgc ggcggatgca gcggccctcg agcacgacaa ggcctacgac    240
cagcagctca aagcgggtga caatccgtac ctgcggtata accacgccga cgccgagttt    300
caggagcgtc tgcaagaaga tacgtctttt ggggcaacc tcgggcgagc agtcttccag    360
gccaagaaga gggttctcga acctcttggt ctggttgagg aaggtgctaa gacggctcct    420
ggaaagaaac gtccggtaga gcagtcgcca caagagccag actcctcctc gggcattggc    480
aagacaggcc agcagcccgc taaaaagaga ctcaattttg gtcagactgg cgactcagag   540
tcagtccccg acccacaacc tctcggagaa cctccagcaa cccccgctgc tgtgggacct    600
actacaatgg cttcaggcgg tggcgcacca atggcagaca ataacgaagg cgccgacgga    660
gtgggtaatg cctcaggaaa ttggcattgc gattccacat ggctgggcga cagagtcatc    720
accaccagca cccgaacatg ggccttgccc acctataaca accacctcta caagcaaatc    780
tccagtgctt caacggggc cagcaacgac aaccactact tcggctacag cacccctgg     840
gggtattttg atttcaacag attccactgc catttctcac cacgtgactg gcagcgactc    900
atcaacaaca attggggat ccggcccaag agactcaact tcaagctctt caacatccaa    960
gtcaaggagg tcacgacgaa tgatggcgtc acgaccatcg ctaataacct taccagcacg   1020
gttcaagtct tctcggactc ggagtaccag ttgccgtacg tcctcggctc tgcgcaccag   1080
ggctgcctcc ctccgttccc ggcggacgtg ttcatgattc cgcagtacgg ctacctaacg   1140
ctcaacaatg gcagccaggc agtgggacgg tcatcctttt actgcctgga atatttccca    1200
tcgcagatgc tgagaacggg caataacttt accttcagct acaccttcga ggacgtgcct   1260
ttccacagca gctacgcgca cagccagagc ctggaccggc tgatgaatcc tctcatcgac   1320
cagtacctgt attacctgaa cagaactcag aatcagtccg gaagtgccca aaacaaggac   1380
ttgctgttta gccggggtc tccagctggc atgtctgttc cgctccaaaa ctggctacct    1440
ggaccctgtt accggcagca gcgcgtttct aaaacaaaaa cagacaacaa caacagcaac    1500
tttacctgga ctggtgcttc aaaatataac cttaatgggc gtgaatctat aatcaaccct    1560
ggcactgcta tggcctcaca caaagacgac aaagacaagt tctttcccat gagcggtgtc    1620
atgatttttg gaaaggagag cgccggagct tcaaacactg cattggacaa tgtcatgatc    1680
acagacgaag aggaaatcaa agccactaac cccgtggcaa ccgaaagatt tgggactgtg    1740
gcagtcaatc tccagagcag cagcacagac cctgcgaccg gagatgtgca tgttatggga    1800
gccttacctg gaatggtgtg gcaagacaga gactatacc tgcagggtcc tatttgggcc    1860
aaaattcctc acacggatgg acactttcac ccgtctcctc tcatgggcgg ctttggactt    1920
aagcacccgc ctcctcagat cctcatcaaa aacacgcctg ttcctgcgaa tcctccggca   1980
gagtttggac ctacaaagtt tgcttcattc atcacccagt attccacagg acaagtgagc    2040
gtggagattg aatgggagct gcagaaagaa aacagcaaac gctggaatcc cgaagtgcag    2100
tatacatcta actatgcaaa atctgccaac gttgatttca ctgtggacaa caatggactt    2160
tatactgagc ctcgccccat tggcacccgt acctcaccc gtcccctg                 2208
```

```
SEQ ID NO: 15            moltype = AA  length = 736
```

-continued

```
FEATURE                 Location/Qualifiers
source                  1..736
                        mol_type = protein
                        organism = synthetic construct
SEQUENCE: 15
MAADGYLPDW LEDNLSEGIR EWWDLKPGAP KPKANQQKQD DGRGLVLPGY KYLGPFNGLD    60
KGEPVNAADA AALEHDKAYD QQLKAGDNPY LRYNHADAEF QERLQEDTSF GGNLGRAVFQ   120
AKKRVLEPLG LVEEGAKTAP GKKRPVEQSP QEPDSSSGIG KTGQQPAKKR LNFGQTGDSE   180
SVPDPQPLGE PPATPAAVGP TTMASGGGAP MADNNEGADG VGNASGNWHC DSTWLGDRVI   240
TTSTRTWALP TYNNHLYKQI SSASTGASND NHYFGYSTPW GYFDFNRFHC HFSPRDWQRL   300
INNNWGFRPK RLNFKLFNIQ VKEVTTNDGV TTIANNLTST VQVFSDSEYQ LPYVLGSAHQ   360
GCLPPFPADV FMIPQYGYLT LNNGSQAVGR SSFYCLEYFP SQMLRTGNNF TFSYTFEDVP   420
FHSSYAHSQS LDRLMNPLID QYLYYLNRTQ NQSGSAQNKD LLFSRGSPAG MSVQPKNWLP   480
GPCYRQQRVS KTKTDNNNSN FTWTGASKYN LNGRESIINP GTAMASHKDD KDKFFPMSGV   540
MIFGKESAGA SNTALDNVMI TDEEEIKATN PVATERFGTV AVNLQSSSTD PATGDVHVMG   600
ALPGMVWQDR DVYLQGPIWA KIPHTDGHFH PSPLMGGFGL KHPPPQILIK NTPVPANPPA   660
EFSATKFASF ITQYSTGQVS VEIEWELQKE NSKRWNPEVQ YTSNYAKSAN VDFTVDNNGL   720
YTEPRPIGTR YLTRPL                                                   736

SEQ ID NO: 16           moltype = DNA   length = 17
FEATURE                 Location/Qualifiers
source                  1..17
                        mol_type = other DNA
                        organism = synthetic construct
SEQUENCE: 16
gctataaggg gccatgc                                                   17
```